United States Patent
Kraus et al.

(10) Patent No.: US 7,087,047 B2
(45) Date of Patent: Aug. 8, 2006

(54) PREDONATION BLOOD SAMPLING APPARATUS

(75) Inventors: Menachem Kraus, Rehovet (IL); Eli Shemesh, Ashdod (IL)

(73) Assignee: Teva Medical Ltd., Ashdod (IL)

( * ) Notice: Subject to any disclaimer, the term of this patent is extended or adjusted under 35 U.S.C. 154(b) by 424 days.

(21) Appl. No.: 10/203,771

(22) PCT Filed: Feb. 13, 2001

(86) PCT No.: PCT/IL01/00138

§ 371 (c)(1),
(2), (4) Date: Jan. 13, 2003

(87) PCT Pub. No.: WO01/58507

PCT Pub. Date: Aug. 16, 2001

(65) Prior Publication Data

US 2003/0208151 A1  Nov. 6, 2003

(30) Foreign Application Priority Data

Feb. 14, 2000  (IL) .................................. 134528

(51) Int. Cl.
- A61B 19/00  (2006.01)
- A61B 5/00   (2006.01)
- A61M 37/00  (2006.01)
- A61M 1/00   (2006.01)

(52) U.S. Cl. ............... 604/408; 604/6.15; 604/6.16; 604/905; 604/403; 604/34; 600/576; 600/578

(58) Field of Classification Search ........ 604/403–416, 604/905, 6.16, 4.01, 6.15, 211, 283, 30, 32, 604/506, 507, 513, 187, 191, 218, 200–206, 604/232, 264, 533–539, 288.02, 290, 540–544, 604/317, 319, 34, 35, 36; 600/576–578

See application file for complete search history.

(56) References Cited

U.S. PATENT DOCUMENTS

| 3,344,785 A | 10/1967 | Hamilton ................... 128/214 |
| 3,467,095 A | 9/1969 | Ross ....................... 128/214.2 |
| 3,654,924 A | 4/1972 | Wilson et al. .......... 128/214 D |
| 3,877,465 A | 4/1975 | Miyake ..................... 128/2 F |
| 4,219,021 A | 8/1980 | Fink ........................ 128/214 B |

(Continued)

FOREIGN PATENT DOCUMENTS

IL  101680  8/1995

(Continued)

OTHER PUBLICATIONS

Japanese Patent Public Disclosure No. HEI 2-297342.

(Continued)

Primary Examiner—Patricia Bianco
(74) Attorney, Agent, or Firm—Ladas and Parry LLP

(57) ABSTRACT

This invention discloses a donor blood donation and sampling system including a donor needle adapted for drawing blood from a body, a blood collection bag coupled to a blood collection conduit which is coupled to the donor needle, a blood sampling conduit also coupled to the donor needle, and a sampling tube assembly arranged for selectable fluid engagement with the blood sampling conduit and for selectable clamping engagement with at least said blood collection conduit. A donor blood donation and sampling method is also disclosed.

22 Claims, 61 Drawing Sheets

U.S. PATENT DOCUMENTS

| | | | |
|---|---|---|---|
| 4,774,964 A | 10/1988 | Bonaldo | 128/763 |
| 5,084,034 A * | 1/1992 | Zanotti | 604/319 |
| 5,217,025 A | 6/1993 | Okamura | |
| 5,328,473 A | 7/1994 | Fayngold et al. | |
| 5,360,012 A | 11/1994 | Ebara et al. | |
| 5,372,143 A | 12/1994 | Bernes et al. | 128/762 |
| 5,456,678 A | 10/1995 | Nicoletti | |
| 5,620,008 A * | 4/1997 | Shinar et al. | 600/576 |
| 5,702,383 A | 12/1997 | Giesler et al. | 604/409 |
| 5,810,775 A | 9/1998 | Shaw | |
| 5,928,166 A * | 7/1999 | Shemesh et al. | 600/576 |
| 6,126,618 A * | 10/2000 | Bischof | 600/576 |
| 6,193,675 B1 | 2/2001 | Kraus et al. | 600/576 |
| 6,387,086 B1 * | 5/2002 | Mathias et al. | 604/409 |
| 6,626,884 B1 * | 9/2003 | Dillon et al. | 604/409 |
| 6,692,479 B1 * | 2/2004 | Kraus et al. | 604/410 |
| 2004/0260265 A1 * | 12/2004 | Goudaliez et al. | 604/410 |

FOREIGN PATENT DOCUMENTS

| | | |
|---|---|---|
| WO | WO 91/00115 | 1/1991 |
| WO | WO 93/21821 | 11/1993 |
| WO | WO 97/45714 | 12/1997 |
| WO | WO 00/24313 | 5/2000 |

OTHER PUBLICATIONS

Samplink™, TEVA Medical Ltd., Product Information, pp. 1-2, 2001.

Maco Pharma, Exhibitor List, http://www.aabb.org/professionals, San Antonio, Texas, Oct. 2001, p. 1.

Becton Dickson—Vacutainer—Venous Blood Collection, "BD Pronto™ Needle Holder", www. bd.com/ca/vacutainer, pp. 1-2, 1997.

* cited by examiner

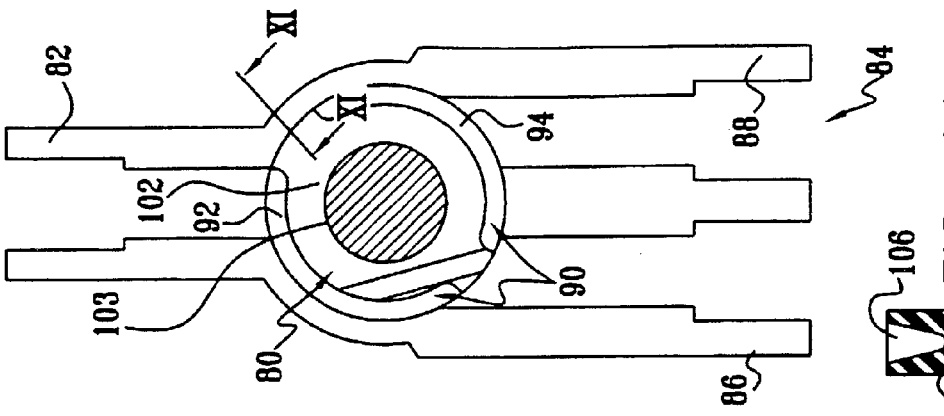
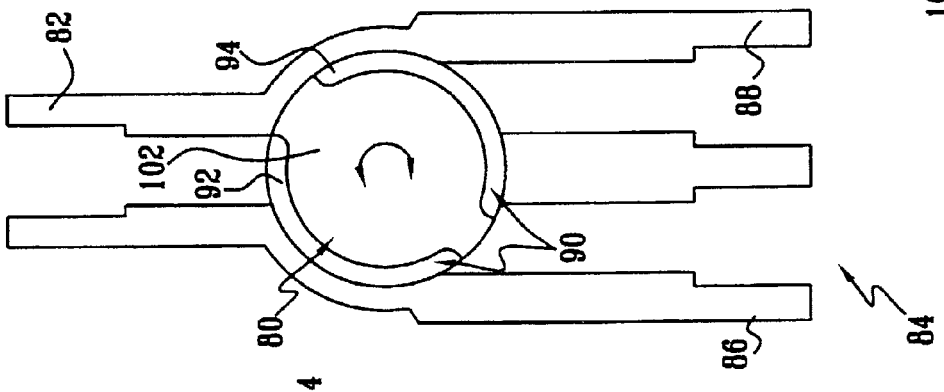
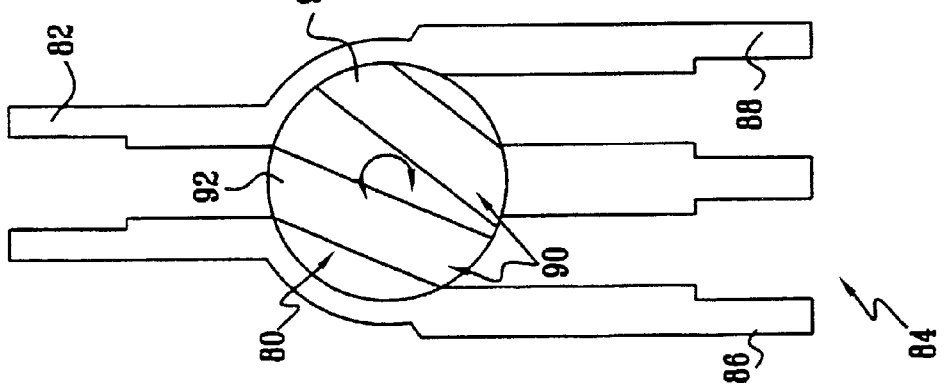
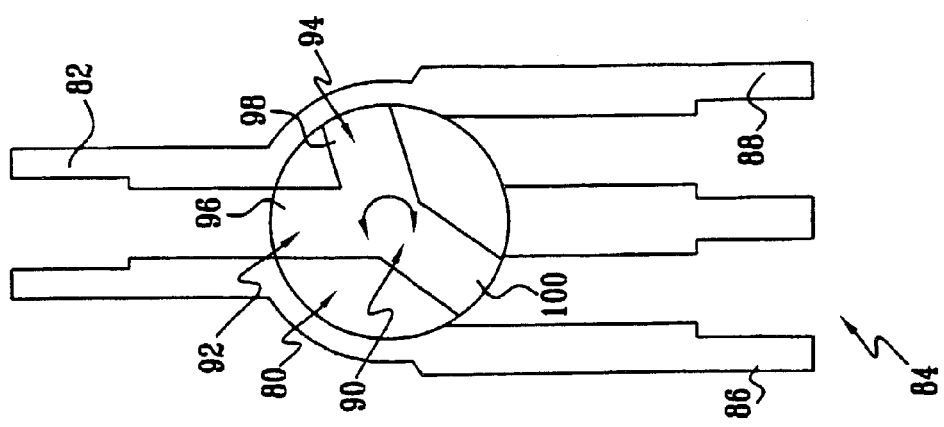
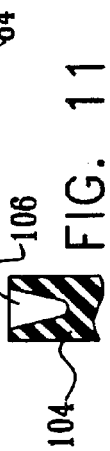

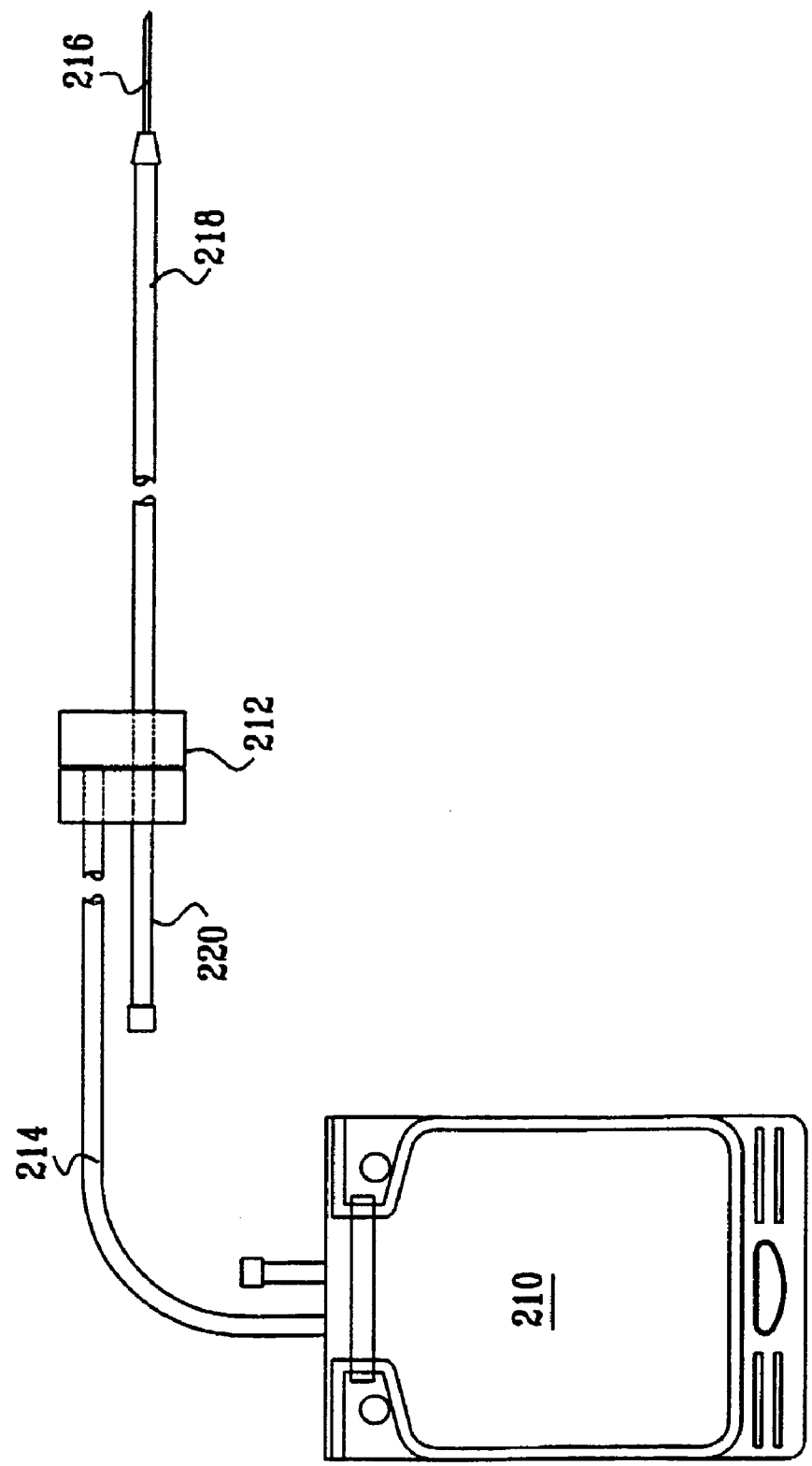

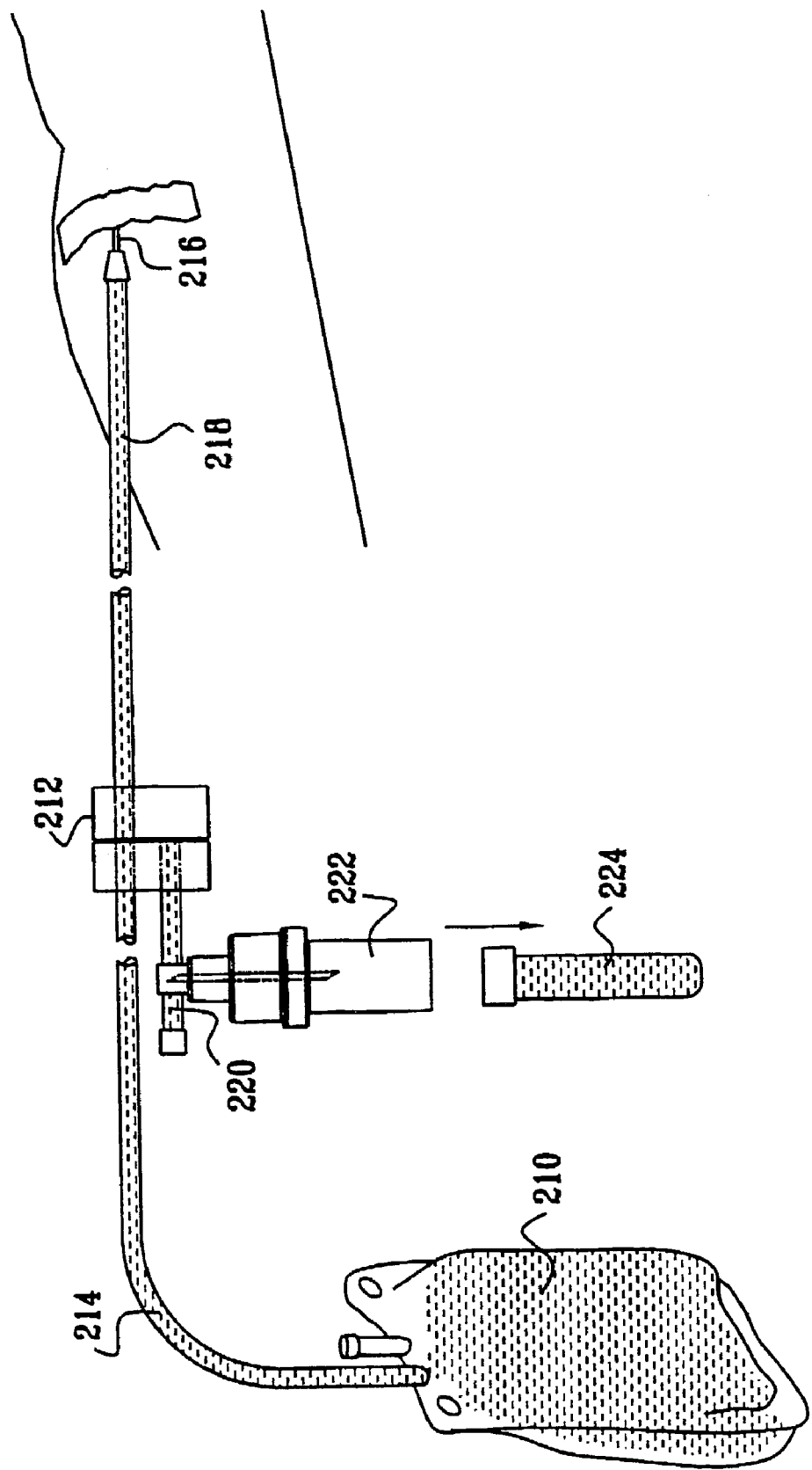

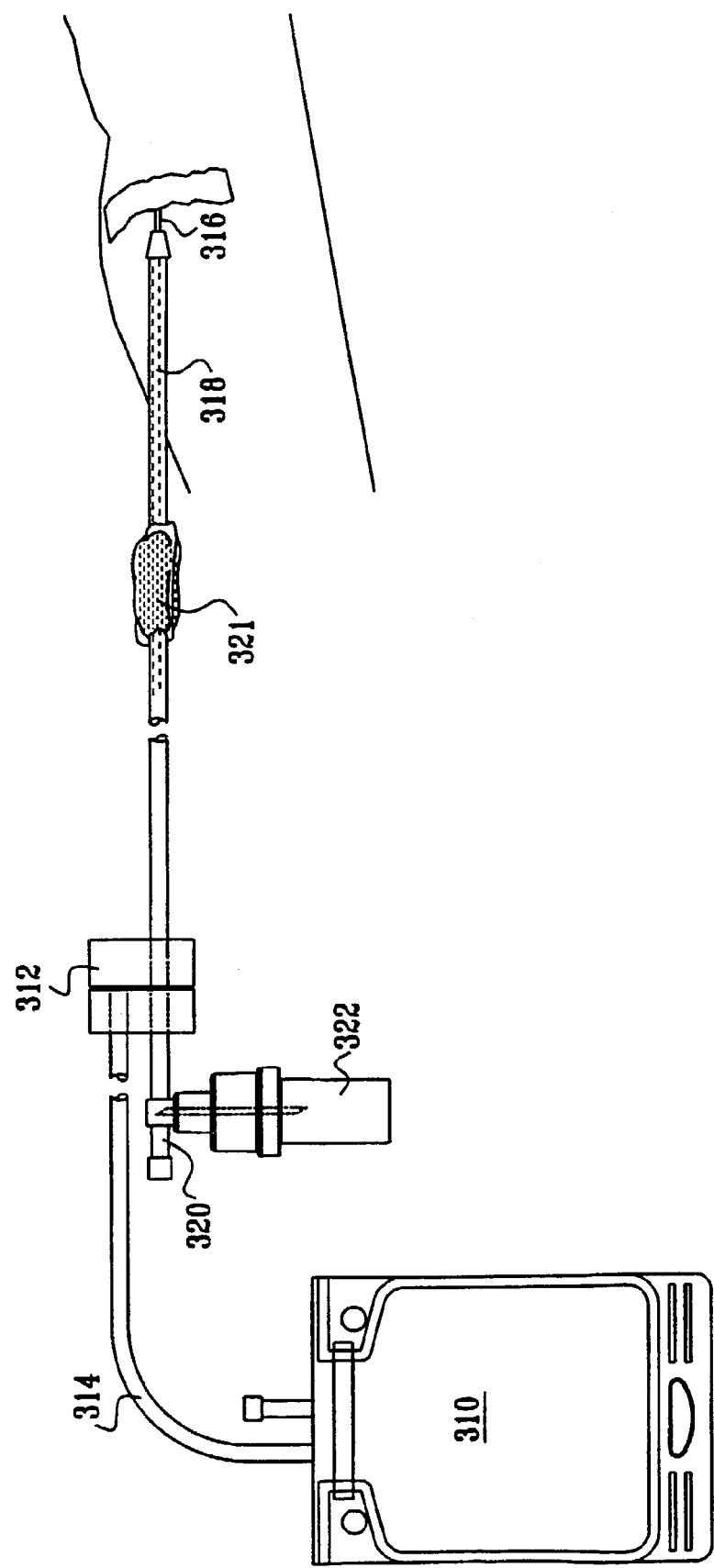

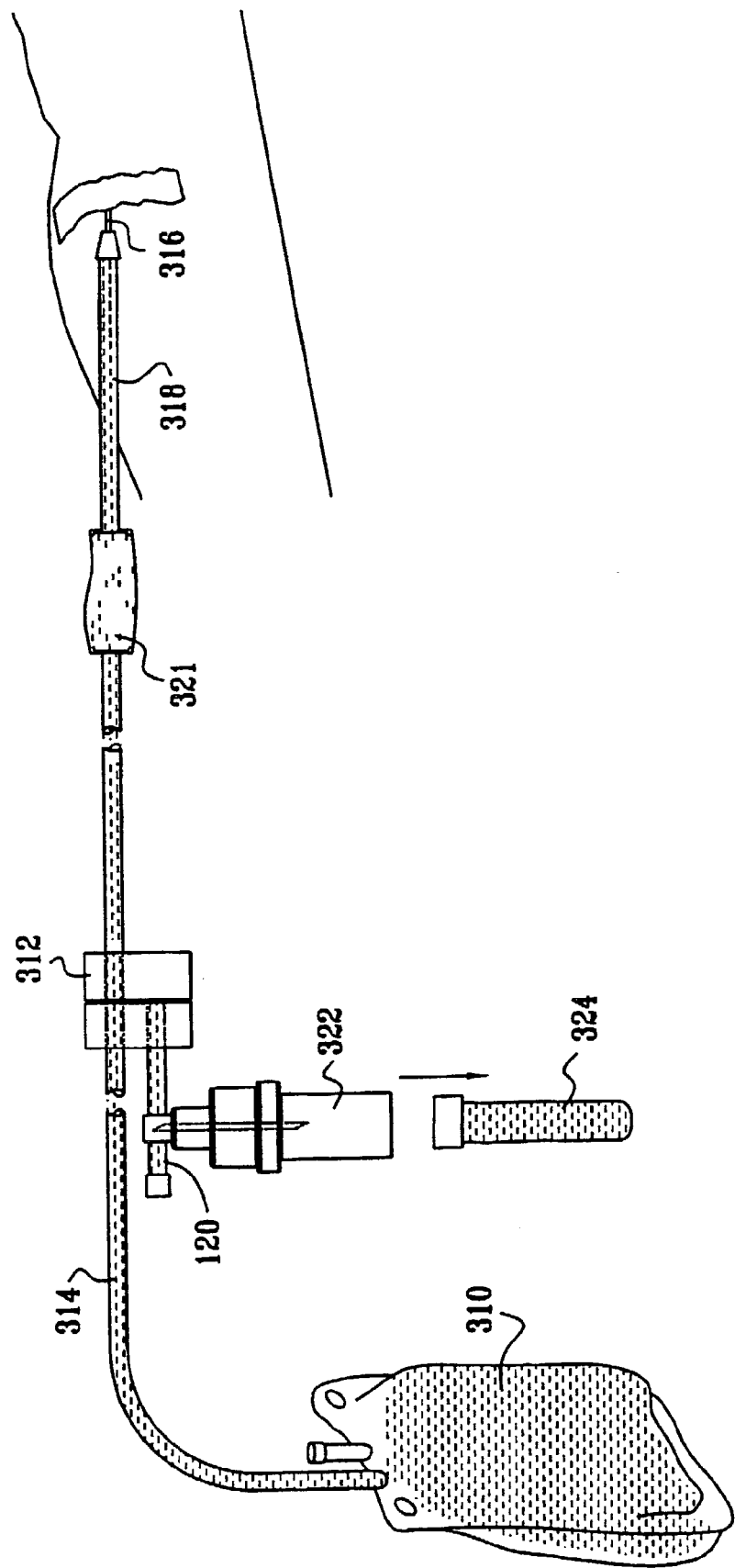

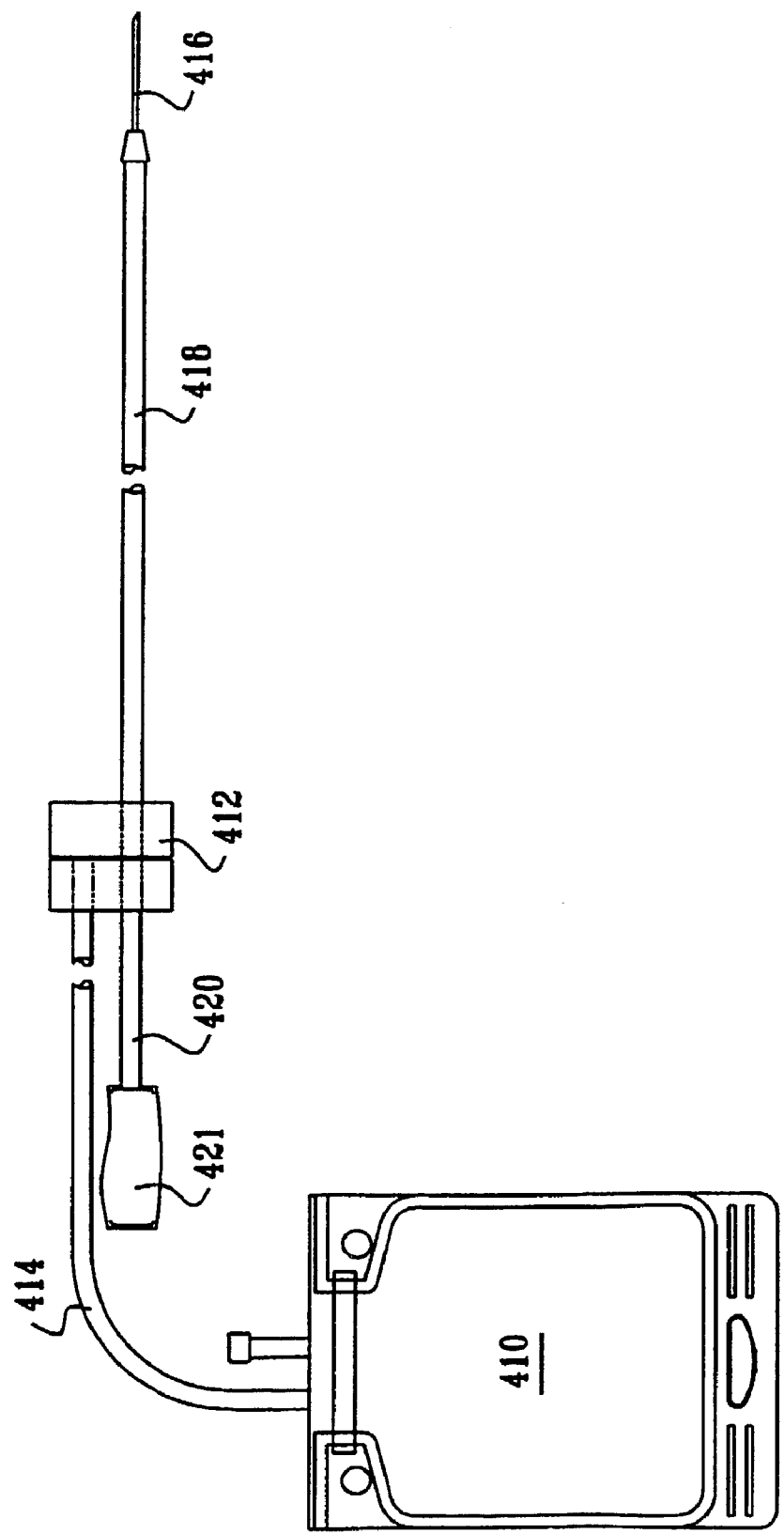

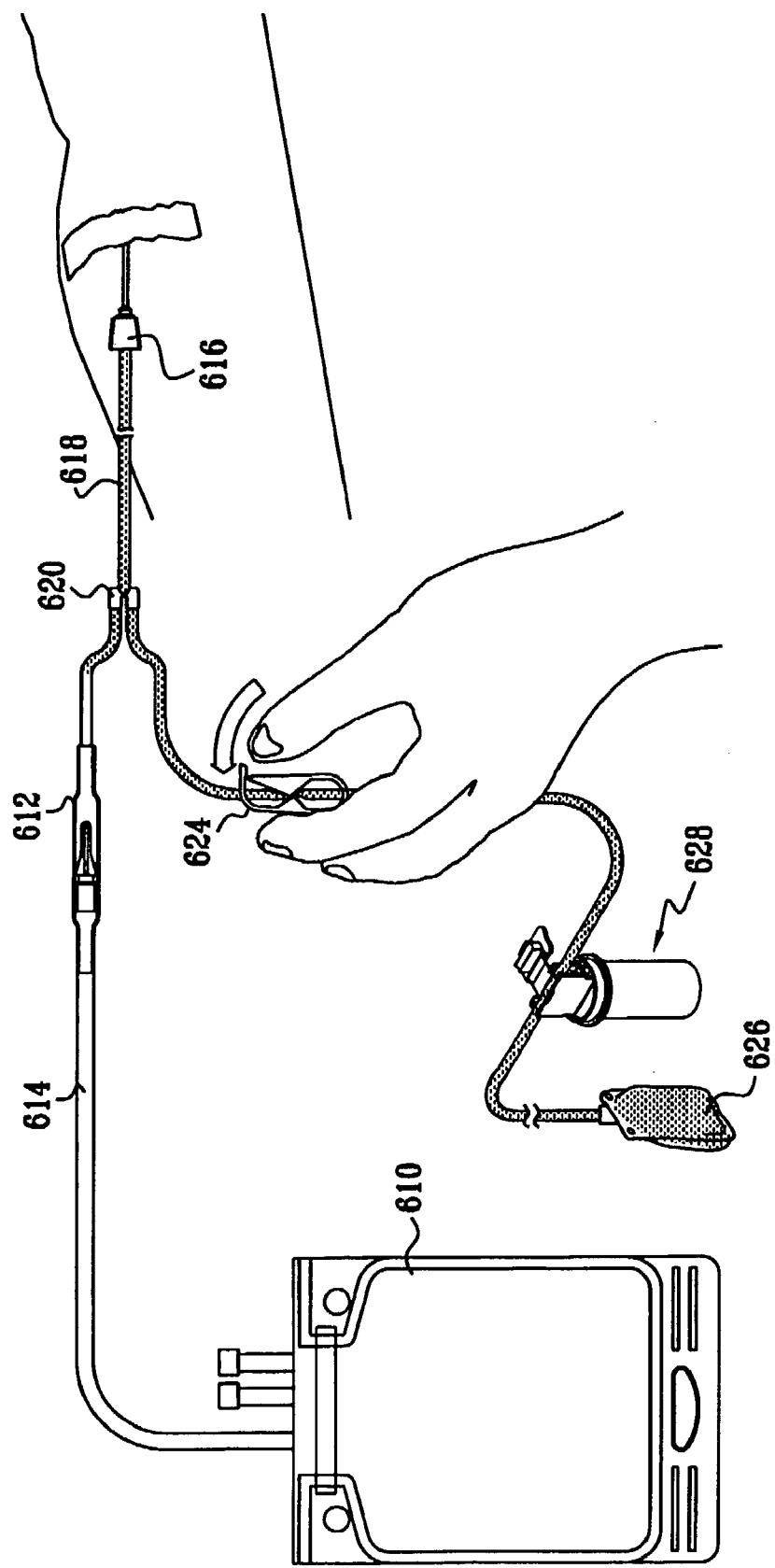

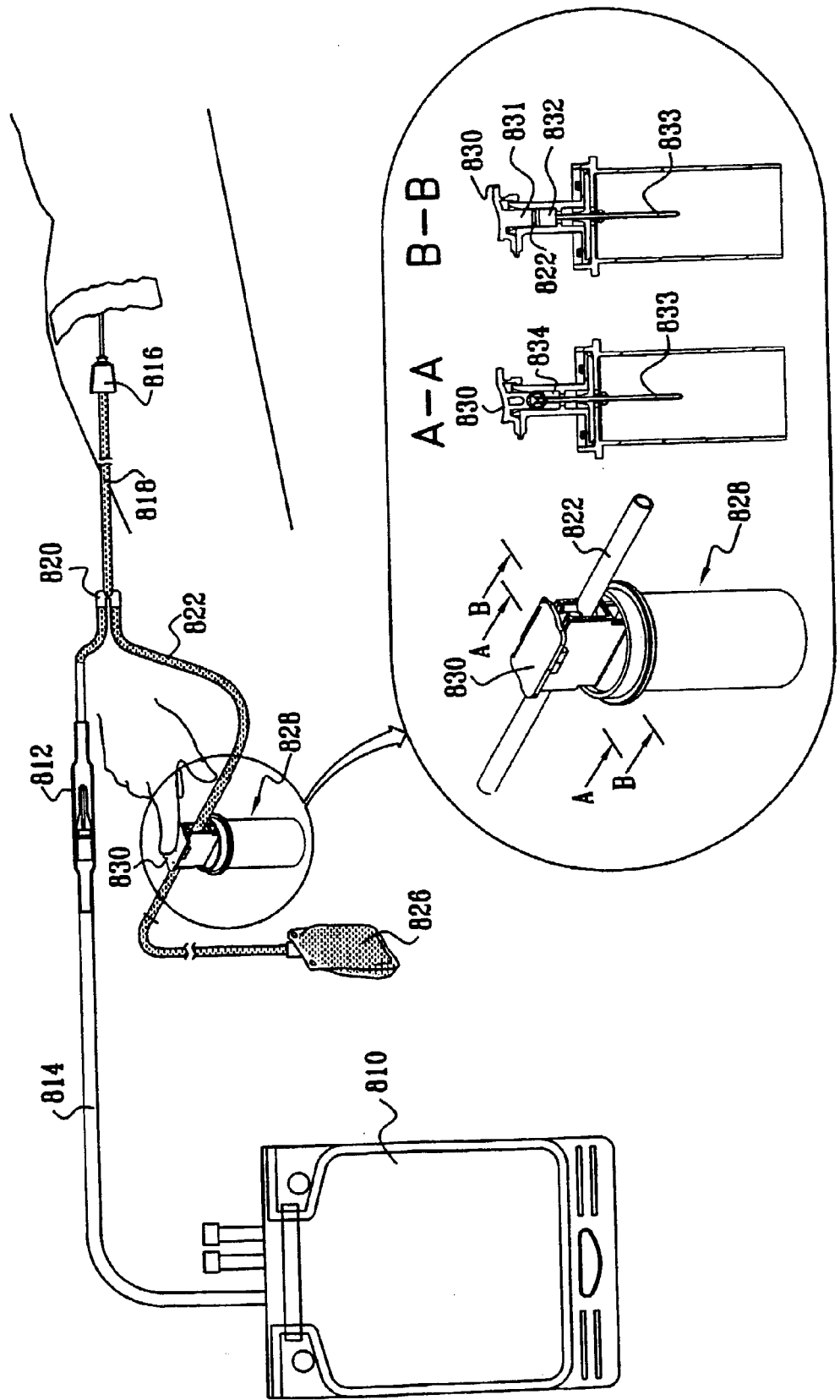

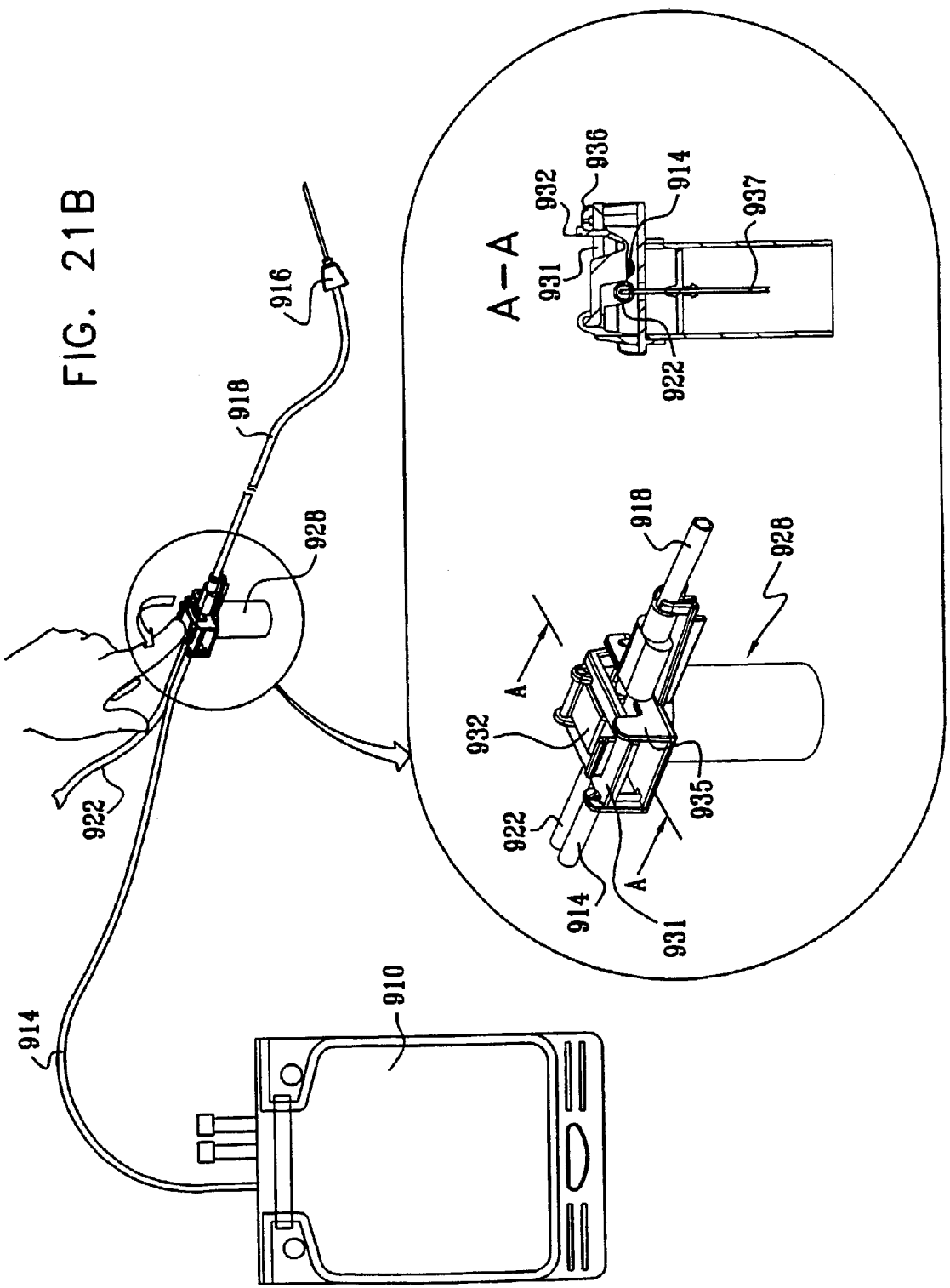

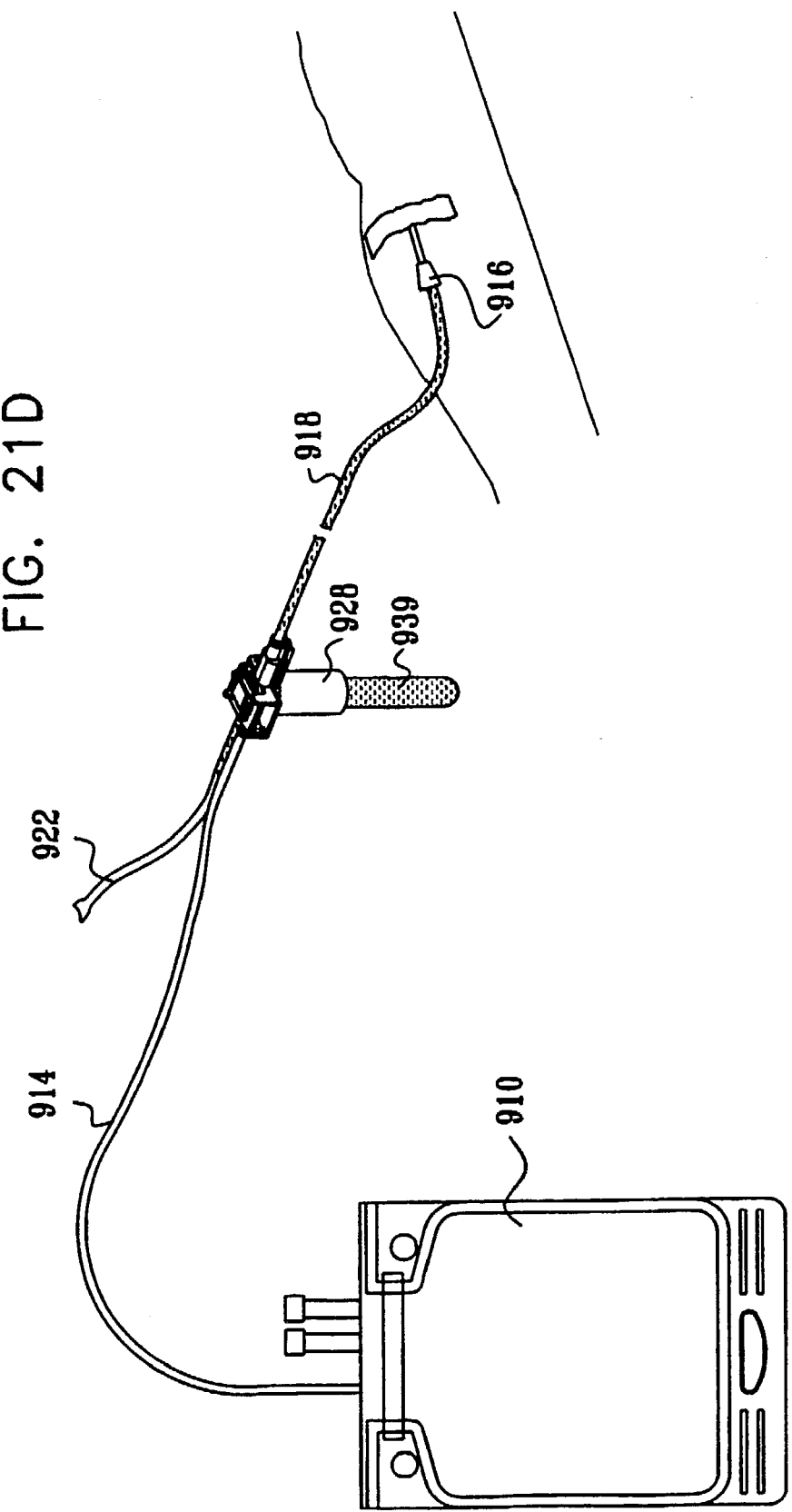

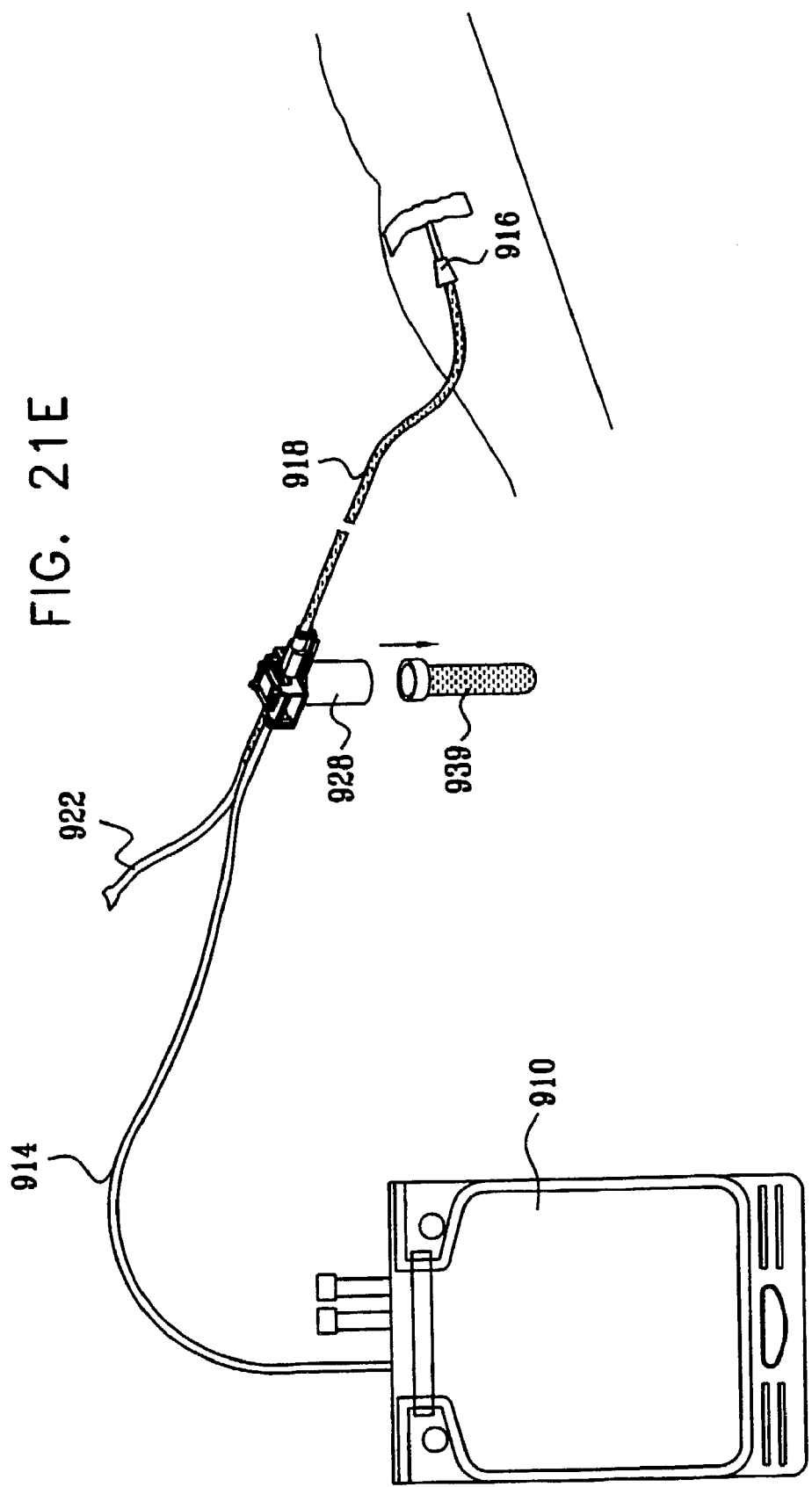

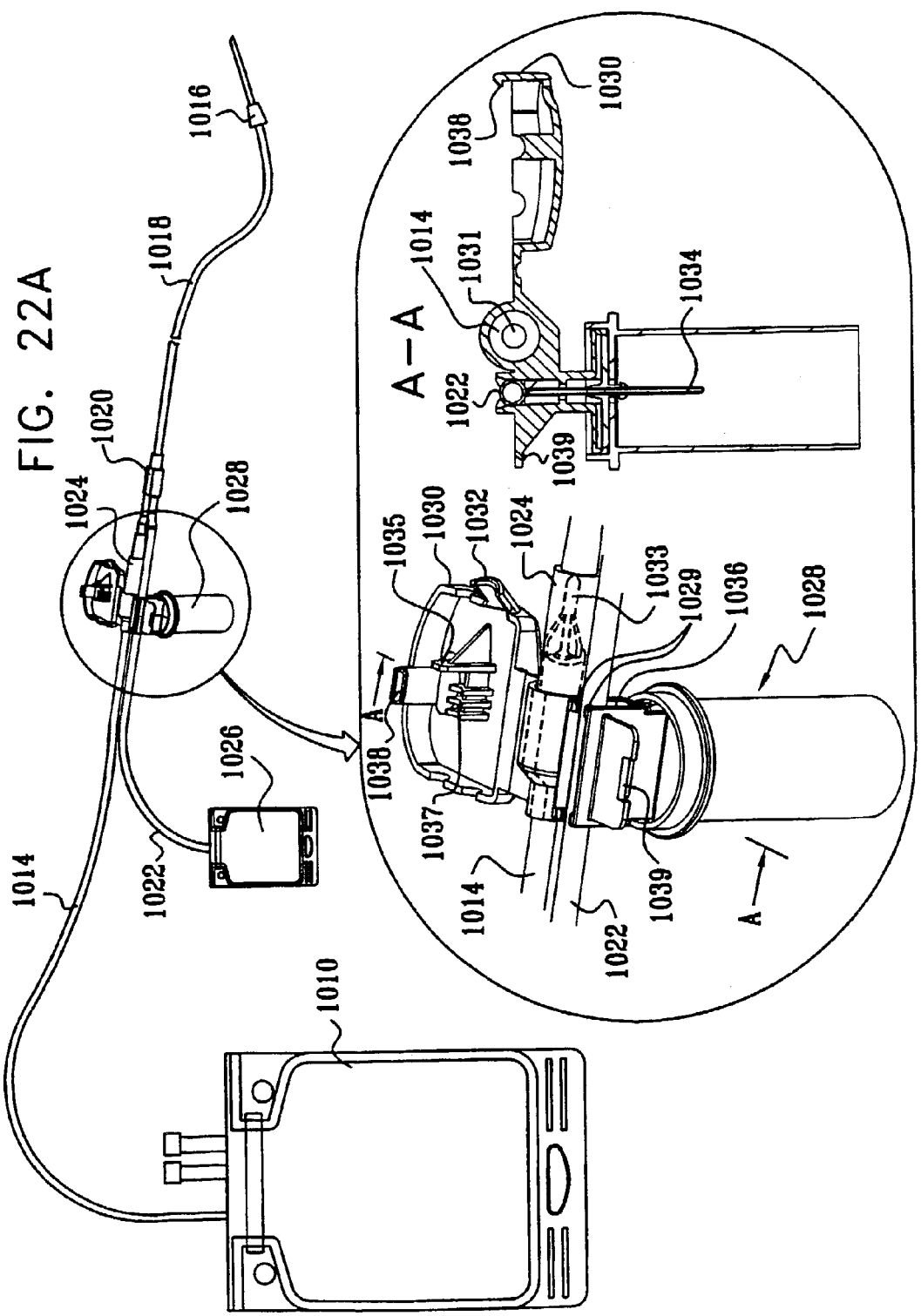

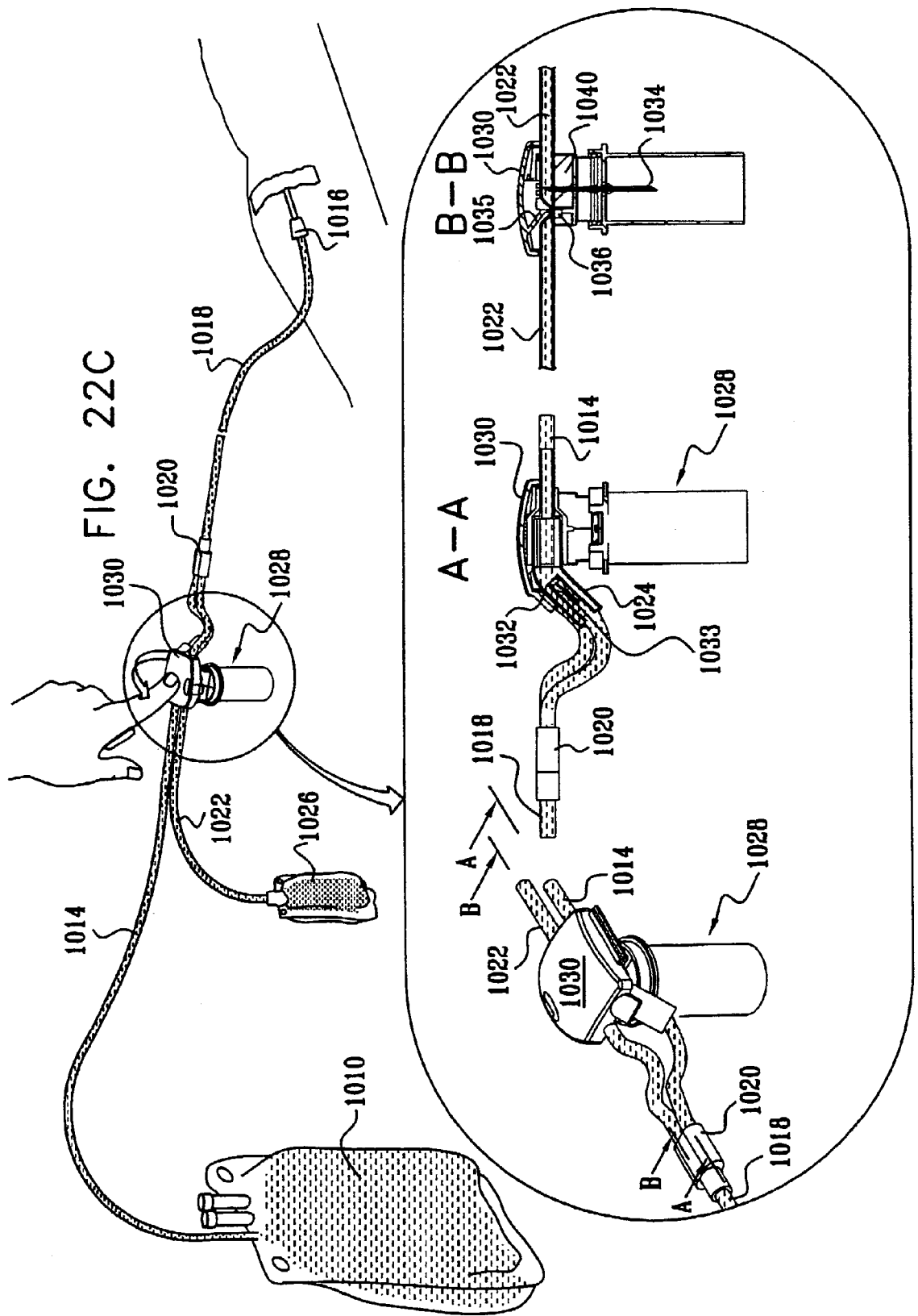

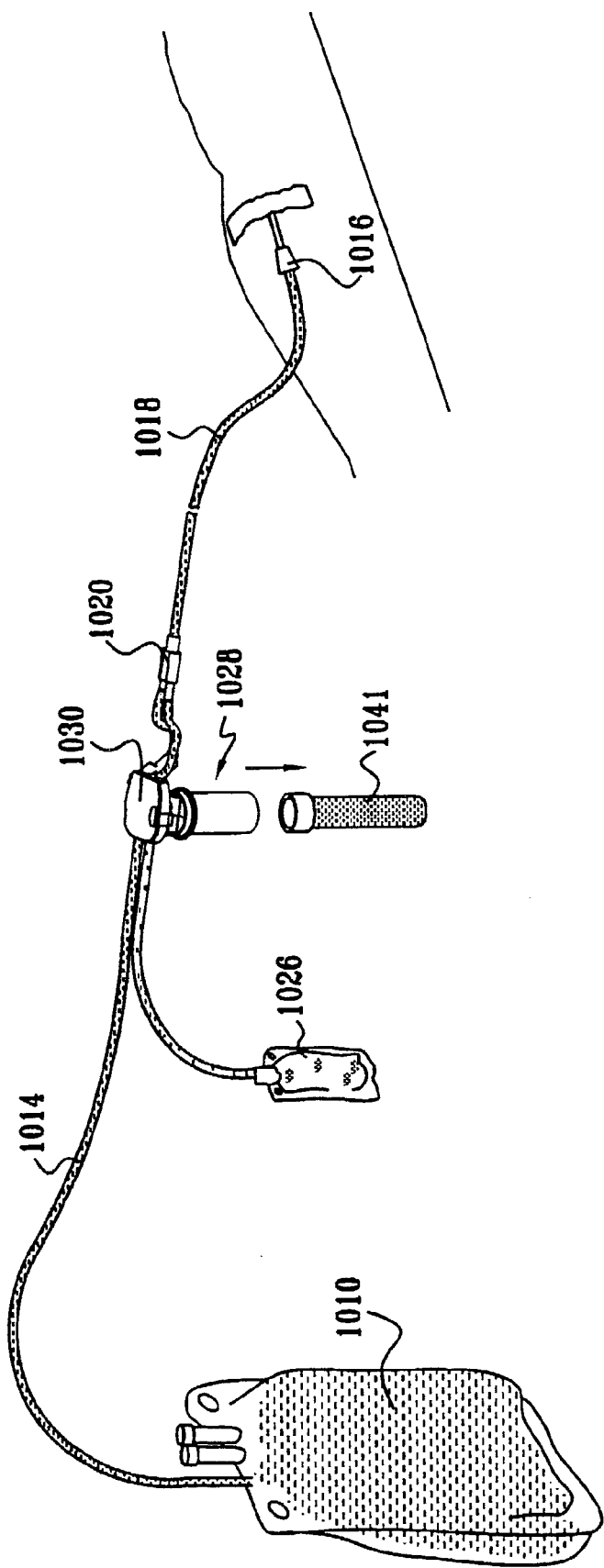

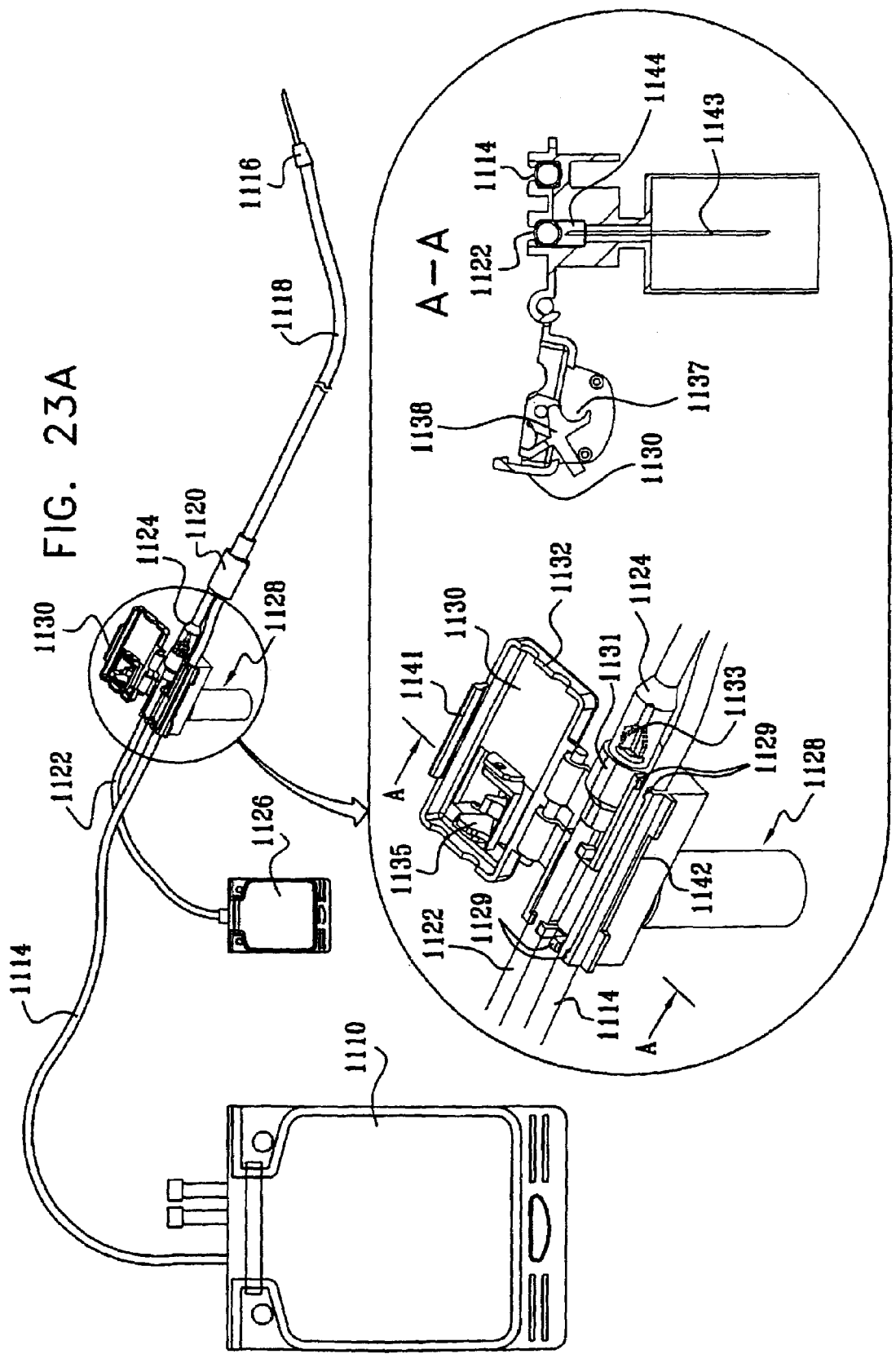

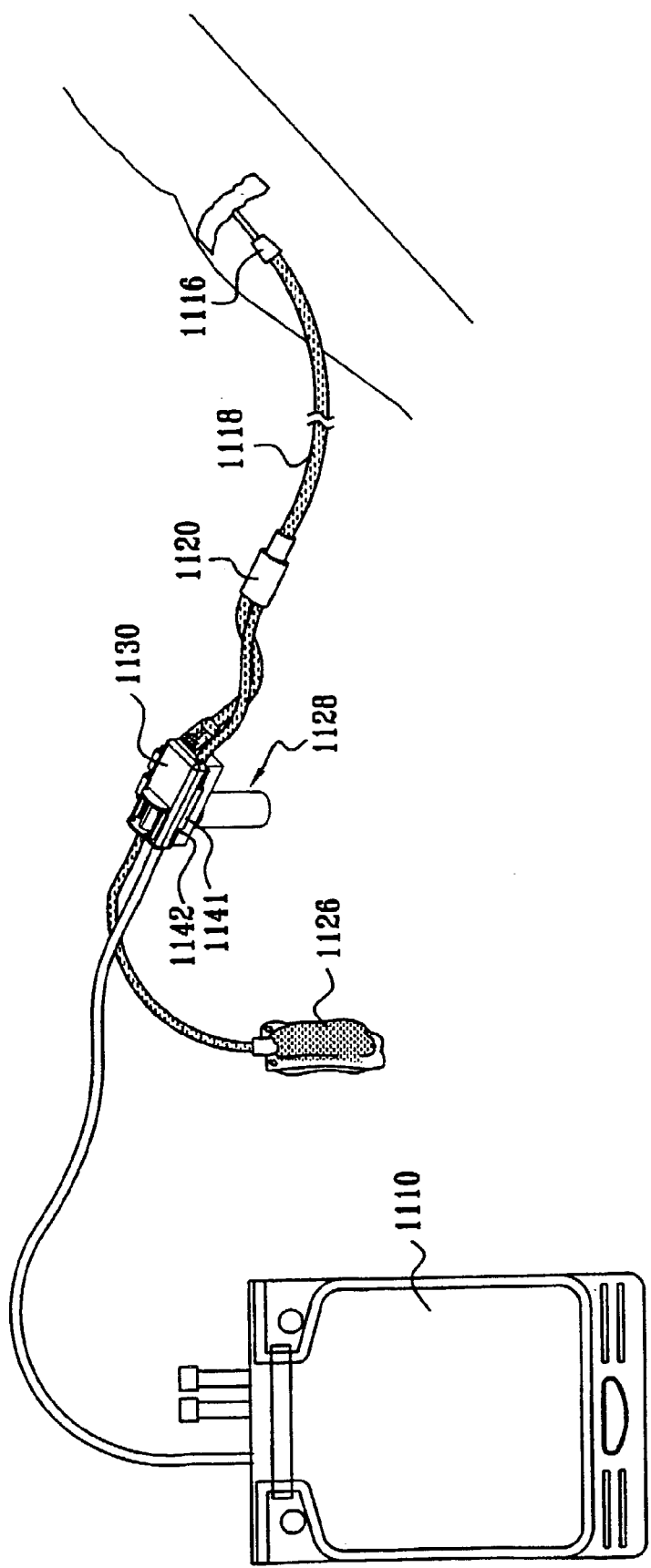

PREDONATION BLOOD SAMPLING APPARATUS

FIELD OF THE INVENTION

The present invention relates generally to a donor blood sampling system and to apparatus and methodologies for blood collection.

BACKGROUND OF THE INVENTION

It is know that approximately 0.1–0.3% of donated blood units are bacterially contaminated. Although this percentage is much higher than blood contaminated by viruses, such as HIV, nevertheless no routine test is currently performed to detect bacterial contamination. This poses a serious problem because a severely contaminated blood unit can cause sepsis in a recipient.

In general, blood is sampled from the vein for viral contamination-testing and typing after completion of donation. However, it is generally believed that the bacterial contamination stems from skin-embedded bacteria inaccessible to the sanitizing agents normally used before venipuncture. Therefore, systems have already been proposed in the prior art wherein a first volume of blood, typically in the order of 25–50 ml, is sampled to determine blood type and to detect for the presence of viruses. The sampling volume washes away most of the bacterial contamination before the blood is collected in the donor bag.

Such a system should satisfy the following criteria:
1. The sampled blood should not be anticoagulated
2. The collected blood must be anticoagulated.
3. Neither the donor nor collected blood should be exposed to the atmosphere during sampling.
4. The system should be simple and user friendly.

FIG. 1 illustrates a prior art predonation system, commercially available from NPBI, Netherlands. This system includes a small sampling bag 10 (with a volume of 30–50 ml) attached to a tubing branch 12 connected via a Y-connector 14 between a donor needle 16, attached to an upstream tube 32, and a main collection bag 18. Satellite bags 17 and 19 may be connected to bag 18 for processing the blood after collection. A needle 20 is attached to the distal side of sampling bag 10 through which blood is withdrawn while the rest of the system is isolated therefrom by means of external clamps 22 on tubing branch 12 and a donor tube 24 leading to main collection bag 18.

As stated above, the sampled blood should not be anticoagulated, whereas the collected blood must be anticoagulated. Accordingly, an anticoagulant used in collection bag 18 must be prevented from entering sampling bag 10. This means that tubing branch 12 must be sealed at all times before donation. This is achieved by means of a breakaway cannula 26 which is an externally openable closure in tubing branch 12 leading to sampling bag 10.

In the prior art system, the following steps are performed:
1. Clamp donor tube 24.
2. Break breakaway cannula 26.
3. Perform venipuncture and collect first blood in sampling bag 10.
4. Clamp tubing branch 12.
5. Open donor tube clamp 22.
6. Collect blood in main bag 18.
7. Connect a vacuum tube holder to needle 20.
8. Sample blood from sampling bag 10.

Another prior art system that operates in a similar manner is commercially available from Macopharma, France. Although the prior art systems approximately satisfy the four criteria mentioned hereinabove, nevertheless, they are labor intensive and cumbersome.

Various types of apparatus and techniques for blood collection and sampling are known in the art and in the patent literature.

The following patents are believed to represent the current state of the art:

U.S. Pat. Nos. 5,928,166; 5,702,383; 5,620,008; 4,774,964; 3,877,465; and Israel Patent No. 101,680.

The following PCT publications are also believed to represent the current state of the art:

Published PCT Patent Application Nos. WO 91/00115; WO 97/45714.

The following products were known prior to the date of the present invention:

Teva Medical SampLink™ System; Beckton Dickinson Vacutainer™.

SUMMARY OF THE INVENTION

The present invention seeks to provide a simple, inexpensive and very easy-to-use donor blood sampling system which solves the abovementioned problems of the prior art and also to provide improved apparatus and methodology for blood collection.

In contrast to the prior art, in a preferred embodiment of the present invention, the donor tube and tubing branch are preferably connected to the tube leading to the donor needle via a unique flow controller. The flow controller provides simple, straightforward blood flow control. The flow controller has only two operating positions. In a first position, this being the position in which the system is provided to the end-user, blood can flow to the sampling bag via the tubing branch, and the donor tube is substantially sealed from blood flowing therein. A user can place the flow controller into a second position, wherein blood can flow to the main collection bag via the donor tube, and the tubing branch is substantially sealed from blood flowing therein. In the present invention, no sampled blood flows towards the collection bag and no anticoagulant agent can contaminate the sampling bag. Neither the donor nor collected blood is ever exposed to the atmosphere during sampling. The system is very simple and user friendly.

There is thus provided in accordance with a preferred embodiment of the present invention a donor blood sampling system including sampling apparatus attached to a tubing branch, a donor needle attached to an upstream tube, the donor needle being adapted for drawing blood from a body, and a main collection bag attached to a donor tube, characterized by a flow controller including an inlet flow member including an inlet port connected to the upstream tube, and an outlet flow member connected to the inlet flow member and including a first outlet port connected to the tubing branch, and a second outlet port connected to the donor tube, the flow controller having a first position and a second position, wherein in the first position, blood can flow to the sampling apparatus via the first outlet port and the tubing branch, the second outlet port and the donor tube being substantially sealed from blood flowing therein, and wherein in the second position, blood can flow to the main collection bag via the second outlet port and the donor tube, the first outlet port and the tubing branch being substantially sealed from blood flowing therein.

In accordance with a preferred embodiment of the present invention a seal is positioned between the inlet flow and outlet flow members that substantially seals the outlet ports from each other.

In accordance with a preferred embodiment of the present invention the outlet flow member is arranged for rotation with respect to the inlet flow member between the first and second positions.

Further in accordance with a preferred embodiment of the present invention the inlet flow member includes a rim that extends from the inlet flow member, the rim defining a receiving volume inwards of a perimeter of the rim, and the outlet flow member sealingly and rotatingly sits in the receiving volume.

Still further in accordance with a preferred embodiment of the present invention the outlet ports are positioned generally symmetrically about a central axis of the flow controller and the inlet port is positioned offset from the central axis.

Additionally in accordance with a preferred embodiment of the present invention, the seal includes an inner seal connected to an outer seal, wherein a central axis of the inner seal is offset from a central axis of the outer seal.

Still further in accordance with a preferred embodiment of the present invention the seal sits in a groove formed in the inlet flow member.

In accordance with a preferred embodiment of the present invention the seal is formed with a channel having two branches arranged for fluid communication with the inlet port and the outlet ports, wherein when one of the branches is in fluid communication with the inlet port and one of the outlet ports, the other branch is not in fluid communication with the other outlet port, thereby substantially preventing fluid flow to the other outlet port.

Further in accordance with a preferred embodiment of the present invention a volume-limiting clamp is clamped to the sampling bag.

In accordance with a preferred embodiment of the present invention the sampling apparatus includes a sampling bag.

In accordance with another preferred embodiment of the present invention the sampling apparatus includes a sampling device that clamps on the tubing branch and is operative to divert blood into a collection tube.

Further in accordance with a preferred embodiment of the present invention the flow controller includes a base formed with a pivot edge and pockets for receiving therein the tubing branch and the donor tube, and a lever pivotedly attached to the base about the pivot edge, the lever including a pair of protrusions that are arranged to press against and substantially seal one of the tubing branch and the donor tube.

Still further in accordance with a preferred embodiment of the present invention the lever includes a pair of lips adapted to fixedly snap onto ridges protruding from the base.

There is also provided in accordance with another preferred embodiment of the present invention a donor blood donation and sampling system a donor needle adapted for drawing blood from a body, a blood collection bag coupled to a blood collection conduit which is coupled to the donor needle, a blood sampling conduit also coupled to the donor needle and a sampling tube assembly arranged for selectable fluid engagement with the blood sampling conduit and for selectable clamping engagement with at least the blood collection conduit.

There is further provided in accordance with yet another preferred embodiment of the present invention a donor blood donation and sampling method. The method includes drawing blood from a body, providing a blood collection bag which is coupled to a blood collection conduit which is, in turn, coupled to the donor needle, coupling a blood sampling conduit to the donor needle and arranging a sampling tube assembly in selectable fluid engagement with the blood sampling conduit for selectable clamping engagement with at least the blood collection conduit, thereby providing blood to the sampling tube assembly prior to providing blood to the blood collection bag.

Further in accordance with a preferred embodiment of the present invention the donor blood donation and sampling system also includes a blood supply conduit coupled to the donor needle and wherein the blood collection conduit and the blood sampling conduit are each coupled to the blood supply conduit.

Still further in accordance with a preferred embodiment of the present invention the donor blood donation and sampling further includes a connector coupling the blood collection conduit and the blood sampling conduit to the blood supply conduit.

Additionally in accordance with a preferred embodiment of the present invention the sampling tube assembly is arranged to receive pre-donation blood directly from the donor needle via the a blood sampling conduit.

Preferably the donor blood donation and sampling system also includes an expansion container connected to at least one of the blood sampling conduit and a supply conduit leading to the blood sampling conduit and the blood collection conduit, the expansion container being operative to enable an initial blood flow from the needle at least toward the expansion container, thereby enabling an operator to readily sense successful communication of the donor needle with blood in the vein of a donor.

Moreover in accordance with a preferred embodiment of the present invention the expansion container is located between the needle and the sampling tube assembly.

Alternatively the expansion container is located downstream of the sampling tube assembly.

Further in accordance with a preferred embodiment of the present invention the donor blood donation and sampling system also includes a breakaway cannula located on the blood collection conduit.

Still further in accordance with a preferred embodiment of the present invention the sampling tube assembly includes a needle having first and second sharpened points at its opposite ends, a clamping assembly for selectable clamping engagement of a blood sampling conduit in fluid engagement with the needle, the clamping engagement causes piercing of the blood sampling conduit by the first sharpened point of the needle, a vacuum sampling tube receiving socket for removably receiving a vacuum sampling tube in fluid engagement with the needle at the second sharped point, thereby providing fluid communication between blood in the blood sampling conduit and the interior of the vacuum sampling tube and resilient material disposed about the first sharpened point for preventing inadvertent piercing of the blood sampling conduit by the needle prior to clamping engagement therewith.

Further in accordance with a preferred embodiment of the present invention the resilient material includes a sealing material, which operates in association with the blood sampling conduit and the needle for preventing leakage of blood from the blood sampling conduit after piercing thereof by the needle. Preferably the resilient material includes a foam material.

Additionally in accordance with a preferred embodiment of the present invention the sampling tube assembly further includes a needle having first and second sharpened points at its opposite ends, a clamping assembly for selectable clamping engagement of a blood sampling conduit in fluid engagement with the needle, the clamping engagement causes piercing of the blood sampling conduit by the first sharpened point of the needle, a vacuum sampling tube receiving socket for removably receiving a vacuum sampling tube in fluid engagement with the needle at the second sharped point, thereby providing fluid communication between blood in the blood sampling conduit and the interior of the vacuum sampling tube. Sealing material is also disposed about the first sharpened point and operates in association with the blood sampling conduit and the needle for preventing leakage of blood from the blood sampling conduit after piercing thereof by the needle.

Still further in accordance with a preferred embodiment of the present invention the sampling tube assembly includes a needle having first and second sharpened points at its opposite ends, a clamping assembly for selectable clamping engagement with a blood sampling conduit in fluid engagement with the needle, the clamping engagement causes piercing of the blood sampling conduit by the first sharpened point of the needle, a vacuum sampling tube receiving socket for removably receiving a vacuum sampling tube in fluid engagement with the needle at the second sharped point, thereby providing fluid communication between blood in the blood sampling conduit and the interior of the vacuum sampling tube. The clamping assembly operates, upon selectable clamping engagement of a blood sampling conduit, to simultaneously block at least one of the blood sampling conduit and a blood collection conduit engaged thereby.

Additionally the sampling tube assembly operates, upon selectable clamping engagement with the blood sampling conduit, to simultaneously block and pierce the blood sampling conduit. Alternatively, the sampling tube assembly operates, upon selectable clamping engagement with the blood sampling conduit and a blood collection conduit, to simultaneously pierce the blood sampling conduit and block the blood collection conduit.

Further in accordance with a preferred embodiment of the present invention the sampling tube assembly includes a needle having first and second sharpened points at its opposite ends, a clamping assembly for selectable clamping engagement with a blood sampling conduit in fluid engagement with the needle, the clamping engagement causes piercing of the blood sampling conduit by the first sharpened point of the needle, a vacuum sampling tube receiving socket for removably receiving a vacuum sampling tube in fluid engagement with the needle at the second sharped point, thereby providing fluid communication between blood in the blood sampling conduit and the interior of the vacuum sampling tube. The assembly also includes a retaining assembly for retaining the sampling tube assembly in engagement with at least the blood sampling conduit prior to clamping engagement therewith.

Still further in accordance with a preferred embodiment of the present invention the retaining, assembly is operative for retaining the blood sampling conduit and the blood collection conduit.

Preferably the blood collection conduit includes a breakaway cannula. Additionally the retaining assembly also retains the breakaway cannula.

Further in accordance with a preferred embodiment of the present invention the clamping assembly is also operative upon selectable clamping engagement with the blood sampling conduit to block the blood collection conduit.

Additionally or alternatively the clamping assembly also operates, upon selectable clamping engagement with the blood sampling conduit, to break the breakaway cannula, thereby permitting blood flow therethrough to the blood collection bag.

Preferably the clamping assembly is also operative upon selectable clamping engagement with the blood sampling conduit to break the breakaway cannula, thereby permitting blood flow therethrough.

Further in accordance with a preferred embodiment of the present invention the sampling tube assembly includes a plurality of retaining protrusions which serve to retain the sampling tube assembly in engagement with the blood collection conduit and with the blood sampling conduit, even before closure of a clamping assembly of the sampling tube assembly.

Still further in accordance with a preferred embodiment of the present invention the sampling tube assembly includes a clamping assembly which operatively engages both the sampling conduit and the collection conduit, the clamping assembly having first and second separately hinged clamping elements. The first clamping element includes engagement protrusions which, when closed, engage the sampling conduit and produce piercing thereof the second clamping element including a protrusion which, when the clamping element is closed, produces blocking of the collection conduit.

Additionally in accordance with a preferred embodiment of the present invention the closing and locking of the first clamping element automatically produces closing and locking of the second clamping element.

Preferably the first and second clamping elements are provided in locked together mutual engagement.

Additionally the second clamping element is unlocked from the first clamping element and opened, thus enabling blood to flow from the needle via the collection conduit to the collection bag. Preferably the second clamping element is unlocked from the first clamping element. The first clamping element remains in operative engagement with the sampling conduit such that the sampling tube assembly remains in piercing engagement therewith, thus preventing leakage of blood therefrom.

Further in accordance with a preferred embodiment of the present invention the clamping assembly is operative to have the following functionalities: breaking of the breakaway cannula to enable blood flow therethrough from the supply conduit to the collection conduit, blocking of the sampling conduit upstream of a piercing needle of the sampling tube assembly and piercing of the sampling conduit.

Additionally in accordance with a preferred embodiment of the present invention the clamping assembly is operative to have the following functionalities: breaking of the breakaway cannula to enable blood flow therethrough from the supply conduit to the sampling conduit and blocking of the collection conduit.

Preferably the breaking of the breakaway cannula is effected by engagement of a protruding breaking tooth formed on the clamping assembly with a portion of the breakaway cannula.

Further in accordance with a preferred embodiment of the present invention the blocking is effected by cooperation of first and second protrusions and isolates the collection bag from a remainder of the system.

Still further in accordance with a preferred embodiment of the present invention the clamping assembly is also operative to have the following functionality: following filling of the sampling bag, by manipulating a clamping element with respect to a remainder of the clamping assembly and causing the piercing and blocking of the sampling conduit as well as simultaneously unblocking the collection conduit.

There is also provided in accordance with another preferred embodiment of the present invention a sampling tube assembly for use in a donor blood sampling system and being arranged for selectable fluid engagement with a blood sampling conduit. The sampling tube assembly includes a needle having first and second sharpened points at its opposite ends, a clamping assembly for selectable clamping engagement of a blood sampling conduit in fluid engagement with the needle, the clamping engagement causes piercing of the blood sampling conduit by the first sharpened point of the needle, a vacuum sampling tube receiving socket for removably receiving a vacuum sampling tube in fluid engagement with the needle at the second sharped point, thereby providing fluid communication between blood in the blood sampling conduit and the interior of the vacuum sampling tube. The sampling tube assembly also includes resilient material disposed about the first sharpened point for preventing inadvertent piercing of the blood sampling conduit by the needle prior to clamping engagement therewith.

There is further provided in accordance with yet another preferred embodiment of the present invention a donor blood sampling method for selectable fluid engagement with a blood sampling conduit. The method includes providing a sampling tube assembly, providing a needle having first and second sharpened points at its opposite ends, employing a clamping assembly for selectable clamping engagement of the blood sampling conduit in fluid engagement with the needle, the clamping engagement causing piercing of the blood sampling conduit by the first sharpened point of the needle, operating a vacuum sampling tube receiving socket for removably receiving a vacuum sampling tube in fluid engagement with the needle at the second sharped point, thereby providing fluid communication between blood in the blood sampling conduit and the interior of the vacuum sampling tube and providing resilient material disposed about the first sharpened point for preventing inadvertent piercing of the blood sampling conduit by the needle prior to clamping engagement therewith.

Further in accordance with a preferred embodiment of the present invention the resilient material includes a sealing material operative in association with the blood sampling conduit and the needle for preventing leakage of blood from the blood sampling conduit after piercing thereof by the needle. Preferably the resilient material includes a foam material.

There is provided in accordance with a preferred embodiment of the present invention a sampling tube assembly for use in a donor blood sampling system. The assembly is arranged for selectable fluid engagement with a blood sampling conduit and includes a needle having first and second sharpened points at its opposite ends, a clamping assembly for selectable clamping engagement of a blood sampling conduit in fluid engagement with the needle, the clamping engagement causes piercing of the blood sampling conduit by the first sharpened point of the needle, a vacuum sampling tube receiving socket for removably receiving a vacuum sampling tube in fluid engagement with the needle at the second sharped point, thereby providing fluid communication between blood in the blood sampling conduit and the interior of the vacuum sampling tube and sealing material disposed about the first sharpened point and being operative in association with the blood sampling conduit and the needle for preventing leakage of blood from the blood sampling conduit after piercing thereof by the needle.

There is also provided in accordance with another preferred embodiment of the present invention a donor blood donation and sampling method for selectable fluid engagement with a blood sampling conduit. The method includes providing a sampling tube assembly, providing a needle having first and second sharpened points at its opposite ends, employing a clamping assembly for selectable clamping engagement of a blood sampling conduit in fluid engagement with the needle, the clamping engagement causes piercing of the blood sampling conduit by the first sharpened point of the needle, operating a vacuum sampling tube receiving socket for removably receiving a vacuum sampling tube in fluid engagement with the needle at the second sharped point, thereby providing fluid communication between blood in the blood sampling conduit and the interior of the vacuum sampling tube and providing sealing material disposed about the first sharpened point and being operative in association with the blood sampling conduit and the needle for preventing leakage of blood from the blood sampling conduit after piercing thereof by the needle.

Preferably the resilient material includes a foam material.

There is further provided in accordance with yet another preferred embodiment of the present invention a sampling tube assembly for use in a donor blood sampling system and being arranged for selectable fluid engagement with a blood sampling conduit. The sampling tube assembly includes a needle having first and second sharpened points at its opposite ends, a clamping assembly for selectable clamping engagement with a blood sampling conduit in fluid engagement with the needle, the clamping engagement causes piercing of the blood sampling conduit by the first sharpened point of the needle, a vacuum sampling tube receiving socket for removably receiving a vacuum sampling tube in fluid engagement with the needle at the second sharped point, thereof providing fluid communication between blood in the blood sampling conduit and the interior of the vacuum sampling tube. The clamping assembly is operative upon selectable clamping engagement of a blood sampling conduit to simultaneously block at least one of the blood sampling conduit and a blood collection conduit engaged thereby.

There is also provided in accordance with another preferred embodiment of the present invention a donor blood sampling method for selectable fluid engagement with a blood sampling conduit. The method includes providing a needle having first and second sharpened points at its opposite ends, employing a clamping assembly for selectable clamping engagement with a blood sampling conduit in fluid engagement with the needle, the clamping engagement causes piercing of the blood sampling conduit by the first sharpened point of the needle, operating a vacuum sampling tube receiving socket for removably receiving a vacuum sampling tube in fluid engagement with the needle at the second sharped point, thereof providing fluid communication between blood in the blood sampling conduit and the interior of the vacuum sampling tube and operating the clamping assembly to selectably engage a blood sampling conduit to simultaneously block at least one of the blood sampling conduit and a blood collection conduit engaged thereby.

Further in accordance with a preferred embodiment of the present invention the clamping assembly is operative upon selectable clamping engagement with the blood sampling conduit to simultaneously block and pierce the blood sampling conduit.

Alternatively the clamping assembly is operative upon selectable clamping engagement with the blood sampling conduit and a blood collection conduit to simultaneously pierce the blood sampling conduit and block the blood collection conduit.

There is further provided in accordance with yet another preferred embodiment of the present invention a sampling tube assembly for use in a donor blood sampling system. The assembly is arranged for selectable fluid engagement with a blood sampling conduit and wherein the sampling tube assembly includes a needle having first and second sharpened points at its opposite ends, a clamping assembly for selectable clamping engagement with a blood sampling conduit in fluid engagement with the needle, the clamping engagement causes piercing of the blood sampling conduit by the first sharpened point of the needle, a vacuum sampling tube receiving socket for removably receiving a vacuum sampling tube in fluid engagement with the needle at the second sharped point, thereby providing fluid communication between blood in the blood sampling conduit and the interior of the vacuum sampling tube and a retaining assembly for retaining the sampling tube assembly in engagement with at least the blood sampling conduit prior to clamping engagement therewith.

There is provided in accordance with yet another preferred embodiment of the present invention a donor blood sampling method for selectable fluid engagement with a blood sampling conduit. The method includes providing a needle having first and second sharpened points at its opposite ends, operating a clamping assembly for selectable clamping engagement with a blood sampling conduit in fluid engagement with the needle, the clamping engagement causes piercing of the blood sampling conduit by the first sharpened point of the needle, operating a vacuum sampling tube receiving socket for removably receiving a vacuum sampling tube in fluid engagement with the needle at the second sharped point, thereby providing fluid communication between blood in the blood sampling conduit and the interior of the vacuum sampling tube and employing a retaining assembly for retaining the sampling tube assembly in engagement with at least the blood sampling conduit prior to clamping engagement therewith.

Further in accordance with a preferred embodiment of the present invention the retaining assembly is operative for retaining the blood sampling conduit and the blood collection conduit.

Still further in accordance with a preferred embodiment of the present invention the blood collection conduit includes a breakaway cannula and wherein the retaining assembly also retains the breakaway cannula. Preferably, the clamping assembly is also operative upon selectable clamping engagement with the blood sampling conduit to block the blood collection conduit.

Additionally in accordance with a preferred embodiment of the present invention the clamping assembly is also operative upon selectable clamping engagement with the blood sampling conduit to break the breakaway cannula., thereby permitting blood flow therethrough.

Preferably the clamping assembly is also operative upon selectable clamping engagement with the blood sampling conduit to break the breakaway cannula, thereby permitting blood flow therethrough.

Moreover in accordance with a preferred embodiment of the present invention the sampling tube assembly also includes a needle having first and second sharpened points at its opposite ends, a clamping assembly for selectable clamping engagement of a blood sampling conduit in fluid engagement with the needle, the clamping engagement causes piercing of the blood sampling conduit by the first sharpened point of the needle, a vacuum sampling tube receiving socket for removably receiving a vacuum sampling tube in fluid engagement with the needle at the second sharped point, thereby providing fluid communication between blood in the blood sampling conduit and the interior of the vacuum sampling tube and resilient material disposed about the first sharpened point for preventing inadvertent piercing of the blood sampling conduit by the needle prior to clamping engagement therewith.

Further in accordance with a preferred embodiment of the present invention the resilient material includes a sealing material operative in association with the blood sampling conduit and the needle, for preventing leakage of blood from the blood sampling conduit after piercing thereof by the needle. Preferably the resilient material includes a foam material.

Still further in accordance with a preferred embodiment of the present invention the sampling tube assembly further includes a needle having first and second sharpened points at its opposite ends, a clamping assembly for selectable clamping engagement of a blood sampling conduit in fluid engagement with the needle, the clamping engagement causes piercing of the blood sampling conduit by the first sharpened point of the needle, a vacuum sampling tube receiving socket for removably receiving a vacuum sampling tube in fluid engagement with the needle at the second sharped point, thereby providing fluid communication between blood in the blood sampling conduit and the interior of the vacuum sampling tube and sealing material disposed about the first sharpened point and being operative in association with the blood sampling conduit and the needle for preventing leakage of blood from the blood sampling conduit after piercing thereof by the needle.

Further in accordance with a preferred embodiment of the present invention the sampling tube assembly also includes a needle having first and second sharpened points at its opposite ends, a clamping assembly for selectable clamping engagement with a blood sampling conduit in fluid engagement with the needle, the clamping engagement causing piercing of the blood sampling conduit by the first sharpened point of the needle, a vacuum sampling tube receiving socket for removably receiving a vacuum sampling tube in fluid engagement with the needle at the second sharped point, thereby providing fluid communication between blood in the blood sampling conduit and the interior of the vacuum sampling tube. The clamping assembly being operative upon selectable clamping engagement of a blood sampling conduit to simultaneously block at least one of the blood sampling conduit and a blood collection conduit engaged thereby.

Further in accordance with a preferred embodiment of the present invention the sampling tube assembly is operative upon selectable clamping engagement with the blood sampling conduit to simultaneously block and pierce the blood sampling conduit.

Still further in accordance with a preferred embodiment of the present invention the sampling tube assembly is operative upon selectable clamping engagement with the blood sampling conduit and a blood collection conduit to simultaneously pierce the blood sampling conduit and block the blood collection conduit.

Additionally in accordance with a preferred embodiment of the present invention the sampling tube assembly includes a needle having first and second sharpened points at its opposite ends, a clamping assembly for selectable clamping engagement with a blood sampling conduit in fluid engagement with the needle, the clamping engagement causing piercing of the blood sampling conduit by the first sharpened point of the needle, a vacuum sampling tube receiving socket for removably receiving a vacuum sampling tube in fluid engagement with the needle at the second sharped point, thereby providing fluid communication between blood in the blood sampling conduit and the interior of the vacuum sampling tube and a retaining assembly for retaining the sampling tube assembly in engagement with at least the blood sampling conduit prior to clamping engagement therewith.

Further in accordance with a preferred embodiment of the present invention the retaining assembly is operative for retaining the blood sampling conduit and the blood collection conduit.

Additionally in accordance with a preferred embodiment of the present invention the blood collection conduit includes a breakaway cannula. Preferably the retaining assembly also retains the breakaway cannula.

Still further in accordance with a preferred embodiment of the present invention the clamping assembly is also operative upon selectable clamping engagement with the blood sampling conduit to block the blood collection conduit.

Additionally in accordance with a preferred embodiment of the present invention the clamping assembly is also operative upon selectable clamping engagement with the blood sampling conduit to break the breakaway cannula, thereby permitting blood flow therethrough to the blood collection bag.

Preferably the clamping assembly is also operative upon selectable clamping engagement with the blood sampling conduit to break the breakaway cannula, thereby permitting blood flow therethrough.

Moreover in accordance with a preferred embodiment of the present invention the sampling tube assembly includes a plurality of retaining protrusions which serve to retain the sampling tube assembly in engagement with the blood collection conduit and with the blood sampling conduit, even before closure of a clamping assembly of the sampling tube assembly.

Additionally in accordance with a preferred embodiment of the present invention the sampling tube assembly includes a clamping assembly which operatively engages both the sampling conduit and the collection conduit, the clamping assembly having first and second separately hinged clamping elements, the first clamping element including engagement protrusions which, when closed, engage the sampling conduit and produce piercing thereof, the second clamping element including a protrusion which, when the clamping element is closed, produces blocking of the collection conduit. Preferably the first clamping element automatically produces closure and locking of the second clamping element.

Additionally the first and second clamping elements are provided in locked together mutual engagement.

Alternatively the second clamping element may be unlocked from the first clamping element and opened, thus enabling blood to flow from the needle via the collection conduit to the collection bag.

Still further in accordance with a preferred embodiment of the present invention the second clamping element is unlocked from the first clamping element, the first clamping element remains in operative engagement with the sampling conduit such that the sampling tube assembly remains in piercing engagement therewith, thus preventing leakage of blood therefrom.

Further in accordance with a preferred embodiment of the present invention the clamping assembly is operative to have the following functionalities: breaking of the breakaway cannula to enable blood flow therethrough from the supply conduit to the collection conduit, blocking of the sampling conduit upstream of a piercing needle of the sampling tube assembly and piercing of the sampling conduit.

Still further in accordance with a preferred embodiment of the present invention the clamping assembly is operative to have the following functionalities: breaking of the breakaway cannula to enable blood flow therethrough from the supply conduit to the sampling conduit and blocking of the collection conduit. Preferably, breaking of the breakaway cannula is effected by engagement of a protruding breaking tooth formed on the clamping assembly with a portion of the breakaway cannula.

Additionally or alternatively the blocking is effected by cooperation of first and second protrusions and isolates the collection bag from a remainder of the system.

Moreover in accordance with a preferred embodiment of the present invention the clamping assembly is also operative to have the following functionality, following filling of the sampling bag: by manipulating a clamping element with respect to a remainder of the clamping assembly, causing piercing and blocking of the sampling conduit as well as simultaneously unblocking collection conduit.

There is also provided in accordance with yet another preferred embodiment of the present invention a donor blood donation and sampling system including a donor needle adapted for drawing blood from a body, a blood collection bag coupled to a blood collection conduit which is coupled to the donor needle, a breakaway cannula located on the blood collection conduit and a blood sampling conduit also coupled to the donor needle.

There is further provided in accordance with a preferred embodiment of the present invention a donor blood donation and sampling method. The method includes providing a donor needle adapted for drawing blood from a body, coupling a blood collection bag to a blood collection conduit which is coupled to the donor needle, locating a breakaway cannula on the blood collection conduit and coupling a blood sampling conduit to the donor needle.

There is also provided in accordance with another preferred embodiment of the present invention a blood donor donation and sampling system. The system includes sampling apparatus attached to a tubing branch, a donor needle attached to an upstream tube, the donor needle being adapted for drawing blood from a body and a main collection bag attached to a donor tube. Preferably, the blood donor donation and sampling system is characterized by a flow controller including an inlet flow member including an inlet port connected to the upstream tube and an outlet flow member connected to the inlet flow member and including a first outlet port connected to the tubing branch, and a second outlet port connected to the donor tube, the flow controller having a first position and a second position, wherein in the first position, blood can flow to the sampling apparatus via the first outlet port and the tubing branch, the second outlet port and the donor tube being substantially sealed from blood flowing therein, and wherein in the second position, blood can flow to the main collection bag via the second outlet port and the donor tube, the first outlet port and the tubing branch being substantially sealed from blood flowing therein.

There is also provided in accordance with a preferred embodiment of the present invention a blood donor donation and sampling method. The method includes providing sampling apparatus attached to a tubing branch, attaching a donor needle to an upstream tube, the donor needle being adapted for drawing blood from a body and attaching a main collection bag to a donor tube. Preferably, the method further includes providing a flow controller and providing an outlet flow member connected to the inlet flow member and comprising a first outlet port connected to the tubing branch, and a second outlet port connected to the donor tube, the flow controller having a first position and a second position, wherein in the first position, blood can flow to the sampling apparatus via the first outlet port and the tubing branch, the second outlet port and the donor tube being substantially sealed from blood flowing therein, and wherein in the second position, blood can flow to the main collection bag via the second outlet port and the donor tube, the first outlet port and the tubing branch being substantially sealed from blood flowing therein. The flow controller includes an inlet flow member including an inlet port connected to the upstream tube.

Further in accordance with a preferred embodiment of the present invention the sampling system further includes a seal positioned between the inlet flow and outlet flow members that substantially seals the outlet ports from each other.

Preferably the outlet flow member is arranged for rotation with respect to the inlet flow member between the first and second positions.

Still further in accordance with a preferred embodiment of the present invention the inlet flow member includes a rim that extends from the inlet flow member, the rim defining a receiving volume inwards of a perimeter of the rim, and the outlet flow member sealingly and rotatingly sits in the receiving volume.

Additionally in accordance with a preferred embodiment of the present invention the outlet ports are positioned generally symmetrically about a central axis of the flow controller and the inlet port is positioned offset from the central axis.

Moreover in accordance with a preferred embodiment of the present invention the seal includes an inner seal connected to an outer seal, wherein a central axis of the inner seal is offset from a central axis of the outer seal.

Preferably the seal sits in a groove formed in the inlet flow member.

Further in accordance with a preferred embodiment of the present invention the seal is formed with a channel having two branches arranged for fluid communication with the inlet port and the outlet ports, wherein when one of the branches is in fluid communication with the inlet port and one of the outlet ports, the other branch is not in fluid communication with the other outlet port, thereby substantially preventing fluid flow to the other outlet port.

Still further in accordance with a preferred embodiment of the present invention the sampling system further includes a volume-limiting clamp clamped to the sampling bag.

Preferably the sampling apparatus includes a sampling bag.

Further in accordance with a preferred embodiment of the present invention the sampling apparatus includes a sampling device that clamps on the tubing branch and is operative to divert blood into a collection tube.

Additionally in accordance with a preferred embodiment of the present invention the flow controller includes a base formed with a pivot edge and pockets for receiving therein the tubing branch and the donor tube and a lever pivotedly attached to the base about the pivot edge, the lever including a pair of protrusions that are arranged to press against and substantially seal one of the tubing branch and the donor tube.

Preferably, the lever includes a pair of lips adapted to fixedly snap onto ridges protruding from the base.

BRIEF DESCRIPTION OF THE DRAWINGS

The present invention will be understood and appreciated more fully from the following detailed description, taken in conjunction with the drawings in which:

FIGS. 7, 8, 9 and 10 are simplified pictorial illustrations of flow controllers useful in the system of FIG. 2, constructed and operative in accordance with four different preferred embodiments of the present invention, wherein a seal is arranged for rotation with respect to inlet and outlet flow members of a flow controller between first and second positions;

FIG. 11 is a simplified sectional illustration of a portion of the seal of the embodiment of FIG. 10, taken along lines XI—XI in FIG. 10;

FIGS. 14A, 14B, 14C, 14D and 14E are simplified illustrations of apparatus and a methodology for blood collection and sampling in accordance with yet another preferred embodiment of the present invention;

FIGS. 15A, 15B, 15C, 15D and 15E are simplified illustrations of apparatus and a methodology for blood collection and sampling in accordance with another further preferred embodiment of the present invention;

FIGS. 16A, 16B, 16C, 16D and 16E are simplified illustrations of apparatus and a methodology for blood collection and sampling in accordance with yet another preferred embodiment of the present invention;

FIGS. 18A, 18B, 18C, 18D, 18E and 18F are simplified illustrations of apparatus and a methodology for blood collection and sampling in accordance with yet another preferred embodiment of the present invention;

FIGS. 20A, 20B, 20C, 20D and 20E are simplified illustrations of apparatus and a methodology for blood collection and sampling in accordance with yet another preferred embodiment of the present invention;

FIGS. 21A, 21B, 21C, 21D, 21E and 21F are simplified illustrations of apparatus and a methodology for blood collection and sampling in accordance with still another preferred embodiment of the present invention;

FIGS. 22A, 22B, 22C, 22D and 22E are simplified illustrations of apparatus and a methodology for blood collection and sampling in accordance with yet another preferred embodiment of the present invention; and FIGS. 23A, 23B, 23C, 23D, 23E and 23F are simplified illustrations of apparatus and a methodology for blood collection and sampling in accordance with another preferred embodiment of the present invention.

DETAILED DESCRIPTION OF A PREFERRED EMBODIMENT

Figure 1:
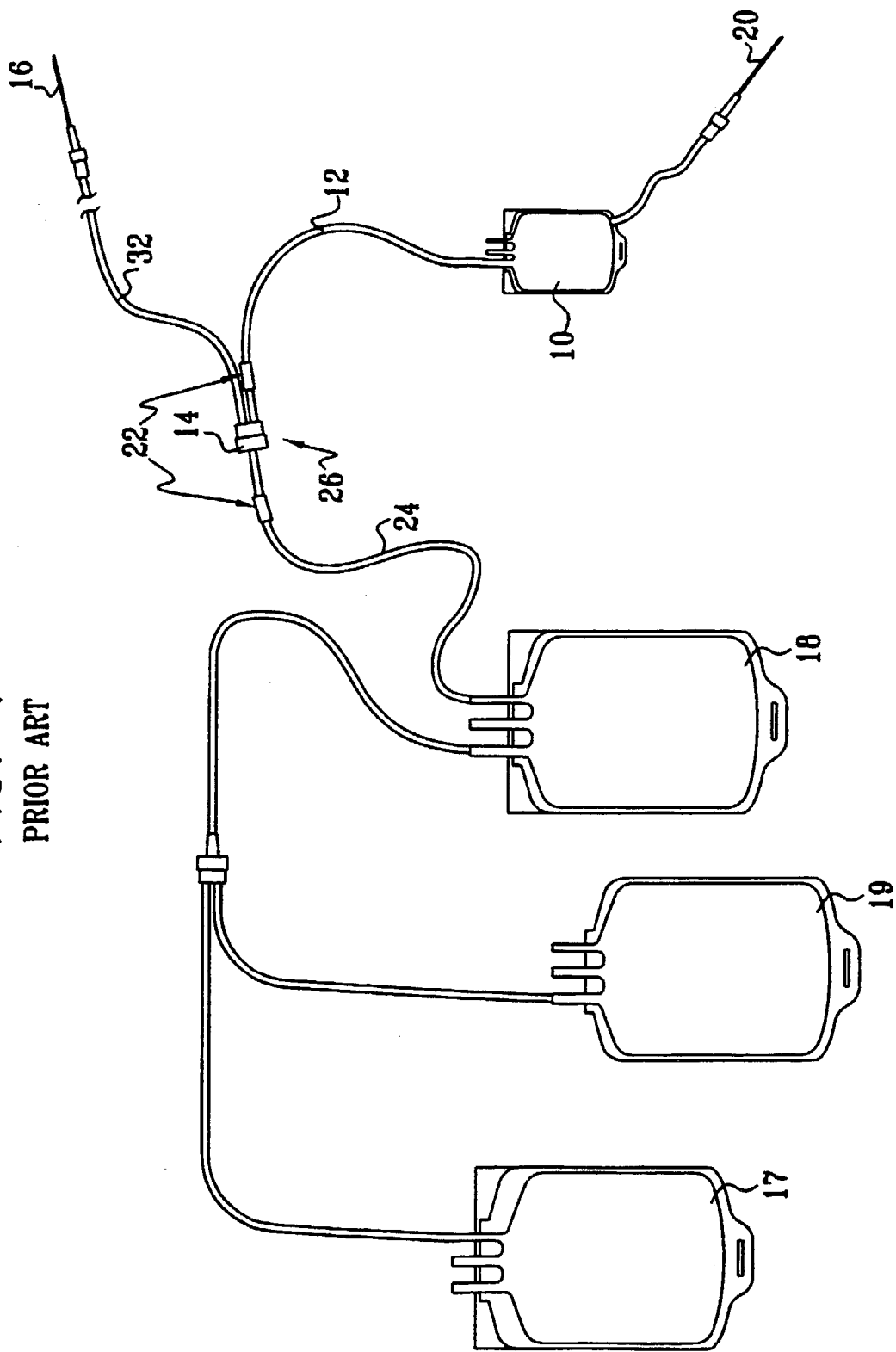
FIG. 1 is a simplified pictorial illustration of a donor blood sampling system of the prior art.
Figure 2:
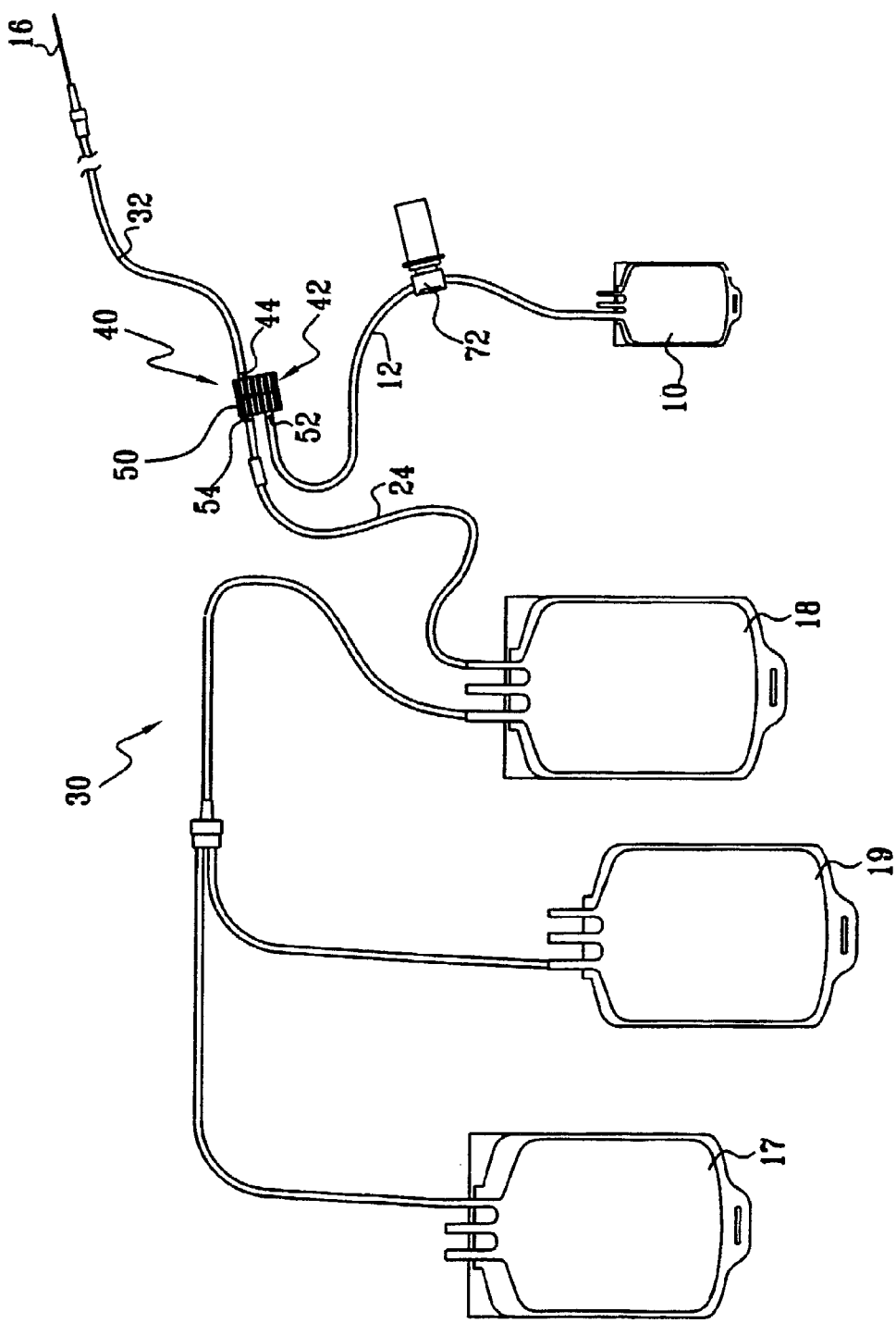
FIG. 2 is a simplified pictorial illustration of a donor blood sampling system constructed and operative in accordance with a preferred embodiment of the present invention.

Reference is now made to FIG. 2 which illustrates a donor blood sampling system 30 constructed and operative in accordance with a preferred embodiment of the present invention. As in the prior art system described hereinabove, system 30 preferably includes a small sampling bag 10 attached to a tubing branch 12, a donor needle 16 attached to an upstream tube 32, and a main collection bag 18 attached to a donor tube 24. Satellite bags 17 and 19 may also be provided.

In contrast to the prior art, in system 30, donor tube 24 aid tubing branch 12 are preferably connected to tube 32 via a flow-controller 40. Flow controller 40 provides simple, straightforward blood flow control. Flow controller 40 has only two operating positions. In a first position, this being the position in which system 30 is provided to the end-user, blood can flow to sampling bag 10 via tubing branch 12, and donor tube 24 is substantially sealed from blood flowing therein. A user can place flow controller 40 into a second position, wherein blood can flow to bag 18 via donor tube 24, and tubing branch 12 is substantially sealed from blood flowing therein, as described in detail hereinbelow.

Figure 4:
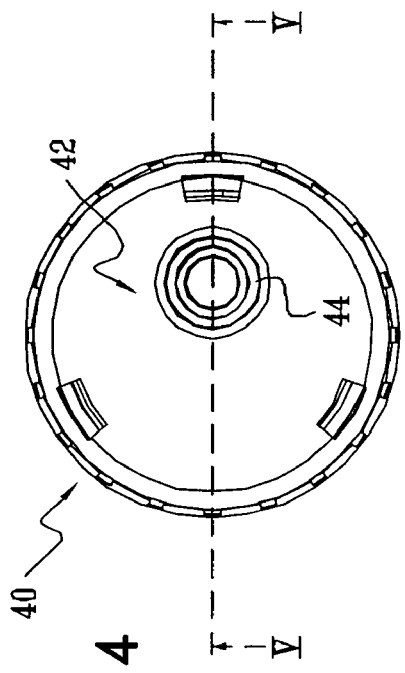
FIGS. 4 and 5 are simplified top-view and sectional illustrations, respectively, of the flow controller of FIG. 3, FIG. 5 being taken along lines V—V in FIG. 4.
Figure 5:
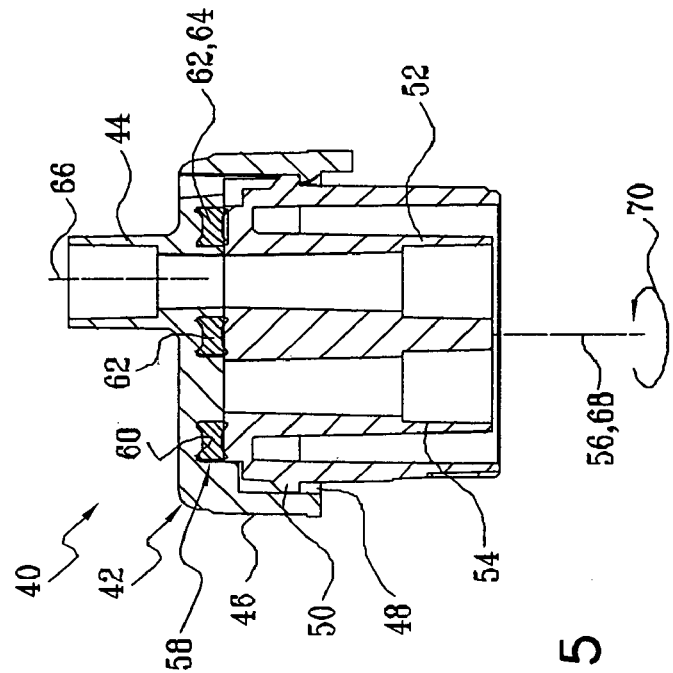
Figure 3:
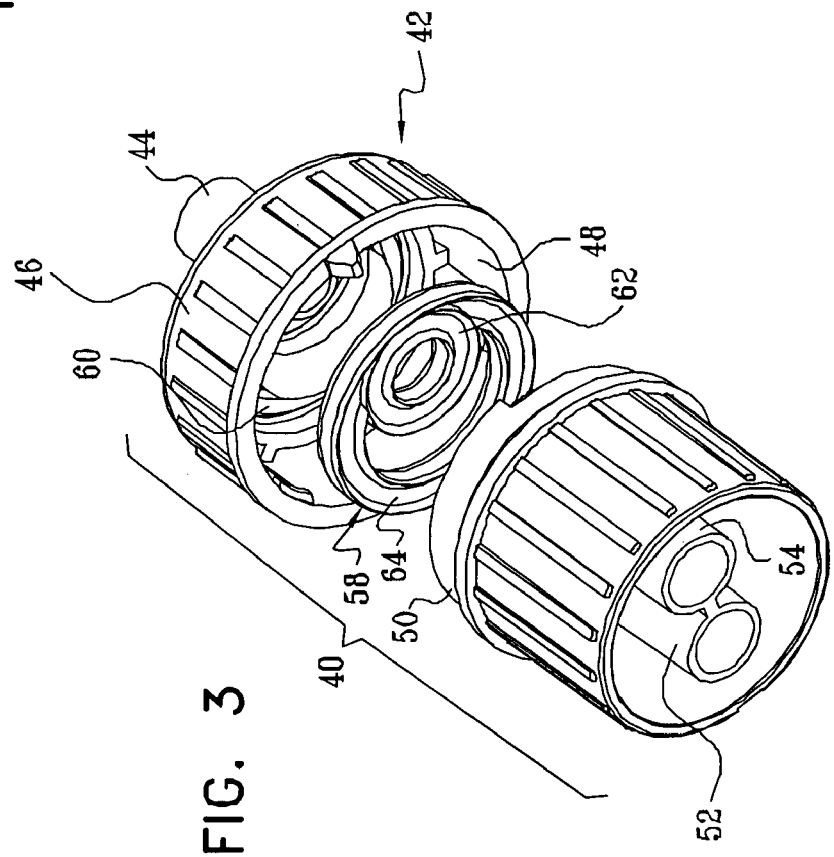
FIG. 3 is a simplified pictorial, exploded illustration of a flow controller useful in the donor blood sampling system of FIG. 2, constructed and operative in accordance with a preferred embodiment of the present invention.

Reference is now made to FIGS. 3–5 which illustrate flow controller 40, constructed and operative in accordance with a preferred embodiment of the present invention. Flow controller 40 preferably includes an inlet flow member 42 with an inlet port 44 connected to upstream tube 32 (FIG. 2). Inlet flow member 42 preferably includes a rim 46 that extends therefrom in a direction generally opposite to inlet port 44. A receiving volume 48 is defined inwards of a perimeter of rim 46, in which sealingly and rotatingly sits an outlet flow member 50.

Outlet flow member 50 preferably includes a first outlet port 52 connected to tubing branch 12 (FIG. 2), and a second outlet port 54 connected to donor tube 24 (FIG. 2). Outlet ports 52 and 54 are preferably positioned generally symmetrically about a central axis 56 (FIG. 5) of flow controller 40 and inlet port 44 is preferably positioned offset from the central axis 56. A seal 58 is preferably positioned between inlet and outlet flow members 42 and 50 that substantially seals outlet ports 52 and 54 from each other. In a preferred embodiment, seal 58 sits in a groove 60 formed in inlet flow member 42, and includes an inner seal 62 connected to an outer seal 64. A central axis 66 of inner seal 62 is preferably offset from a central axis 68 of outer seal 64 (FIG. 5), generally the same amount of offset as the offset arrangement of inlet port 44 with respect to axis 56.

Outlet flow member 50 is arranged for rotation about axis 56 with respect to inlet flow member 42 between first and second positions. In the first position, shown in FIG. 5, blood can flow to sampling bag 10 via first outlet port 52 and tubing branch 12, second outlet port 54 and donor tube 24 being substantially sealed from blood flowing therein. Inlet flow member 42 can be rotated about axis 56 with respect to outlet flow member 50, generally in the direction of an arrow 70 (FIG. 5) to a second position. In this position, blood can flow to main collection bag 18 via second outlet port 54 and donor tube 24, first outlet port 52 and tubing branch 12 being substantially sealed from blood flowing therein.

Thus, in the present invention, the steps for sampling and collecting blood are reduced and simplified to the following:

1. Perform venipuncture and commence drawing blood with flow controller 40 in first position. (Blood initially flows to sampling bag 10.)
2. After sampling bag 10 has filled, place flow controller 40 into second position.
3. Collect blood in bag 18.
4. During or after donation, sample blood from sampling bag 10, as is now described with reference to FIG. 2.

Referring to FIG. 2, in a most preferred embodiment, a sampling device 72 is attached to tubing branch 12 upstream of sampling bag 10. Sampling device 72 is preferably constructed in accordance with the device described in published PCT patent application WO 97/45714, assigned to the present assignee, the disclosure of which is incorporated herein by reference. Sampling device 72 clamps conveniently and easily on tubing branch 12 and allows sampling blood from tubing branch 12 into a collection tube, e.g., a vacuum tube, such as a familiar VACUTAINER tube. Sampling bag 10 needs no special attachments. It is further noted that sampling device 72 can be used to sample blood without any sampling bag 10, the blood being diverted into the vacuum tube.

Figure 6:
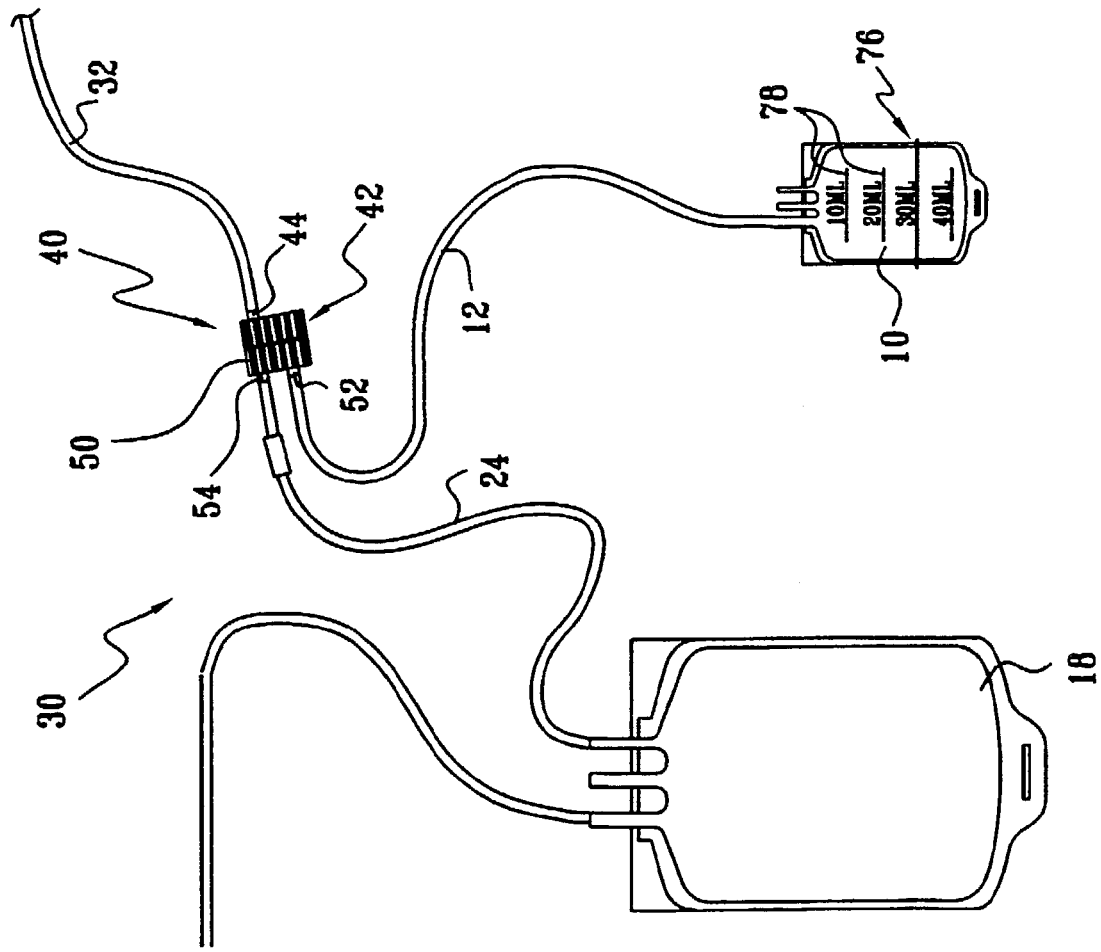
FIG. 6 is a simplified pictorial illustration of the donor blood sampling system of FIG. 2, with a volume-limiting clamp on a sampling bag, in accordance with a preferred embodiment of the present invention.

Referring to FIG. 6, it is seen that sampling bag 10 may be provided with a volume-limiting clamp 76 that limits the amount of blood collected in sampling bag 10. Sampling bag 10 may be provided with graduations 78 to indicate a position for placing clamp 76.

Reference is now made to FIGS. 7, 8, 9 and 10 which are simplified pictorial illustrations of flow controllers, constructed and operative in accordance with four different preferred embodiments of the present invention, wherein a seal 80 is arranged for rotation with respect to inlet and outlet flow members 82 and 84 of a flow controller between first and second positions. Outlet flow member 84 comprises a first outlet port 86 and a second outlet port 88.

Seal 80 is preferably formed with a channel 90 having two branches 92 and 94 arranged for fluid communication with inlet port 82 and outlet ports 86 and 88, wherein when one of the branches is in fluid communication with inlet port 82 and one of the outlet ports (86 or 88), the other branch is not in fluid communication with the other outlet port, thereby substantially preventing fluid flow to the other outlet port, as is now described in more detail.

In the embodiment of FIG. 7, the branches 92 and 94 together form a Y-shaped channel 90, with upper members 96 and 98 each extending into a lower member 100. In other words, branch 92 comprises flow from upper member 96 to lower member 100, and branch 94 comprises flow from upper member 98 to lower member 100.

In the embodiment of FIG. 8, branches 92 and 94 are two separate, generally linear branches.

In the embodiment of FIG. 9, branches 92 and 94 are two separate, generally arcuate branches cut out on the perimeter of a disc 102.

In the embodiment of FIG. 10, which is basically the same as that of FIG. 9, disc 102 is mounted on a central axle 103. Disc 102 is preferably formed with a cross section shaped like a trough 106, as seen in the sectional view of FIG. 11. Disc 102 is preferably formed of an elastomer. In all of the embodiments of FIGS. 7–10, seal 80 rotates generally about its center point.

Figure 12:
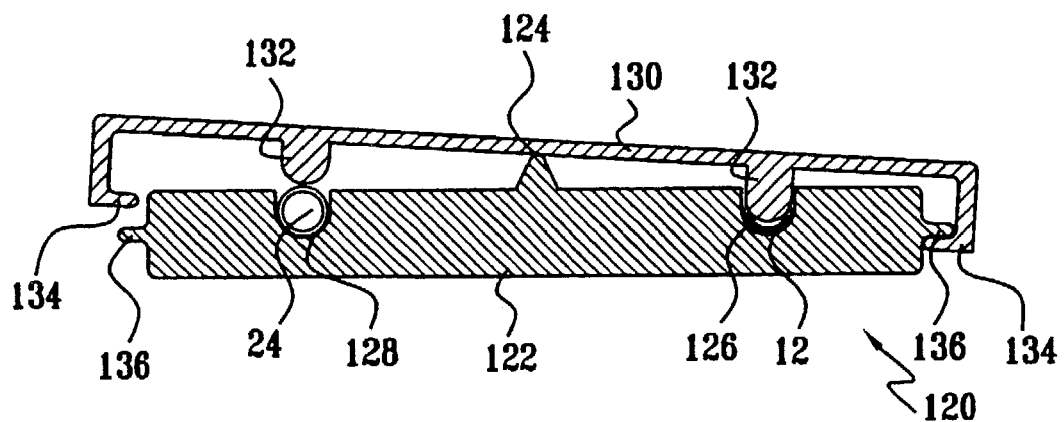
FIGS. 12 and 13 are simplified sectional and top-view illustrations of a flow controller useful in the donor blood sampling system of FIG. 2, constructed and operative in accordance with yet another preferred embodiment of the present invention.
Figure 13:
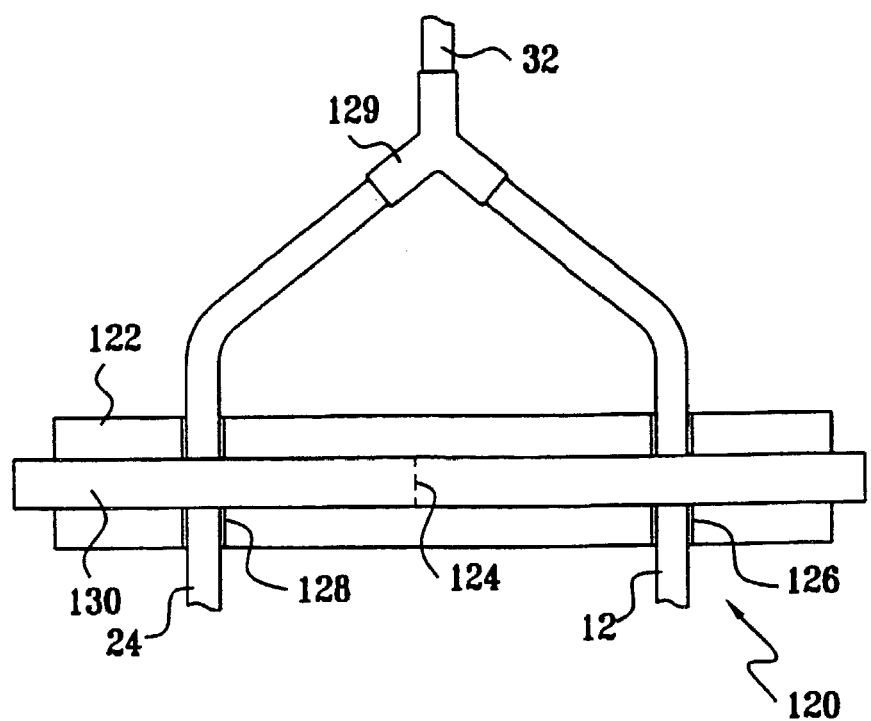

Reference is now made to FIG. 12 which illustrates a flow controller 120 useful in the donor blood sampling system of FIG. 2, constructed and operative in accordance with yet another preferred embodiment of the present invention. Elements common to flow controllers 40 and 120 are designated by the same numerals. Flow controller 120 preferably includes a base 122 formed with a pivot edge 124. Base 122 is preferably formed with pockets 126 and 128 for receiving therein tubing branch 12 and donor tube 24, respectively. A branched connector 129 (FIG. 13) is preferably provided for connecting upstream tube 32 to tubing branch 12 and donor tube 24.

A lever 130 is preferably pivotedly attached to base 122 about pivot edge 124. Lever 130 preferably includes a pair of protrusions 132 that are arranged to press against and substantially seal either tubing branch 12 or donor tube 24. In FIG. 12, it is seen that one of the protrusions 132 presses against and substantially seals tubing branch 12, while the other protrusion 132 does not seal donor tube 24, thereby allowing blood flow through donor tube 24. Lever 130 may be provided with a pair of lips 134 that can fixedly snap onto ridges 136 protruding from base 122, as shown in FIG. 12.

Figure 14B:
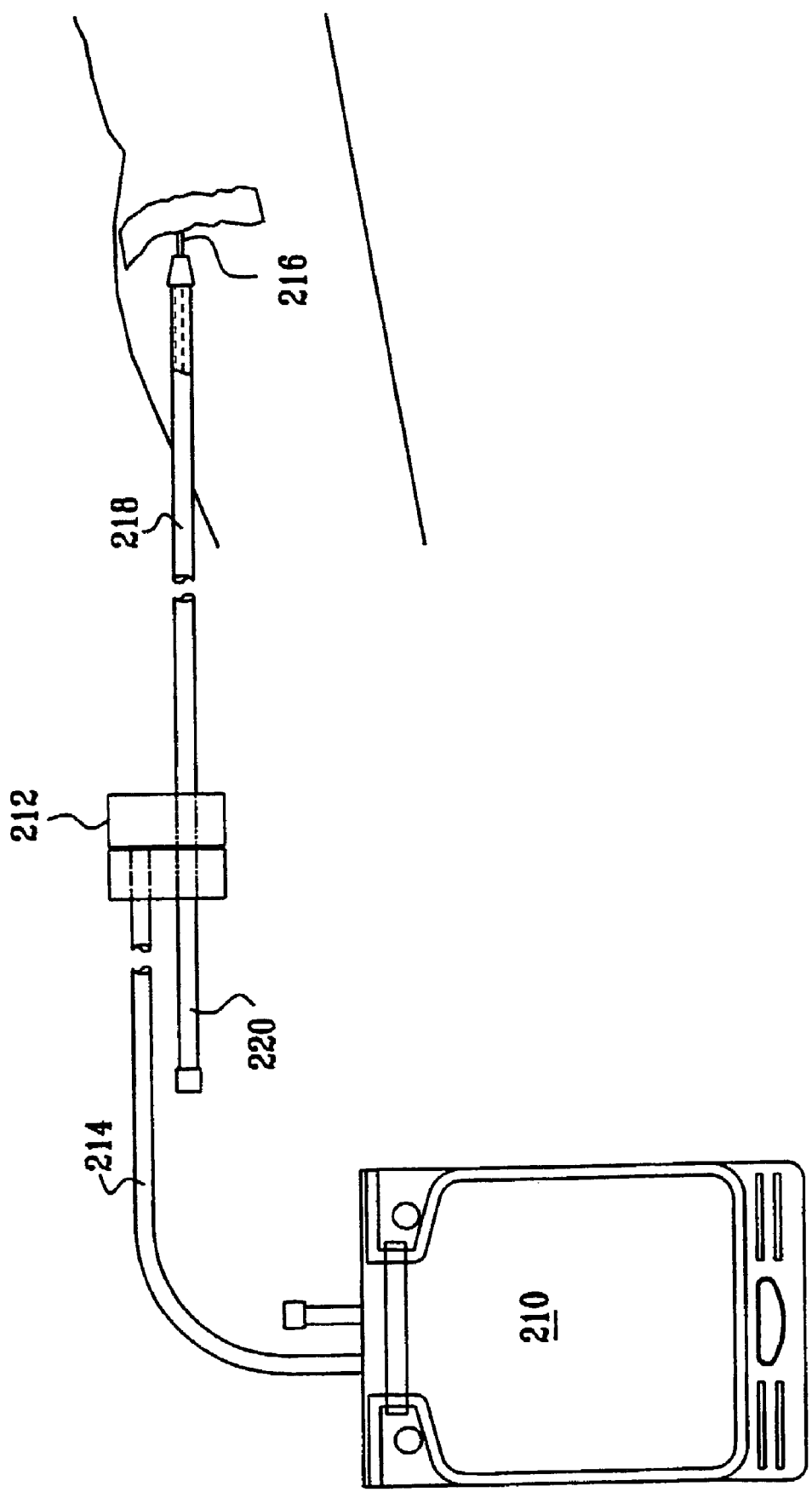

Reference is now made to FIGS. 14A, 14B, 14C, 14D and 14E, which are simplified illustrations of apparatus and a methodology for blood collection and sampling in accordance with one preferred embodiment of the present invention. As seen in FIG. 14A, a collection bag 210, such as a conventional collection bag commercially available from Teva Medical Ltd. of Ashdod, Israel, is connected to a rotatable sampling valve 212 via a collection conduit 214. A collection needle 216 is coupled to sampling valve 212 via a supply conduit 218. A sampling conduit 220 is also coupled to sampling valve 212. Valve 212 is operative to selectably couple the supply conduit 218 to either but not both of collection conduit 214 and sampling conduit 220.

As seen in FIG. 14B, when the needle 216 is initially inserted into a donor's vein, and the valve 212 is initially positioned so as to couple supply conduit 218 to sampling conduit 220 due to air in supply conduit 218, the donor's blood fills only a small portion of supply conduit 218, adjacent needle 216.

Figure 14C:
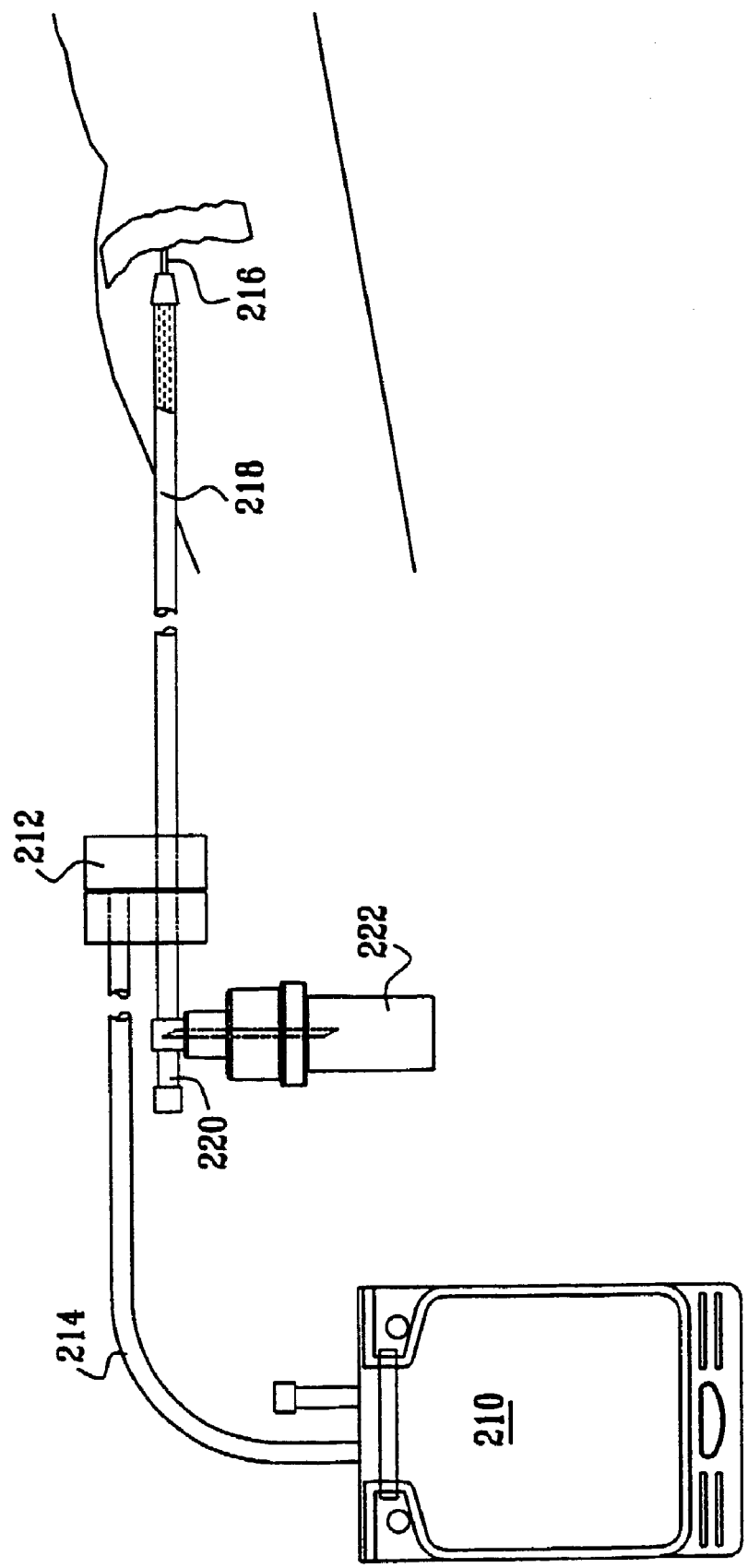
Figure 14D:
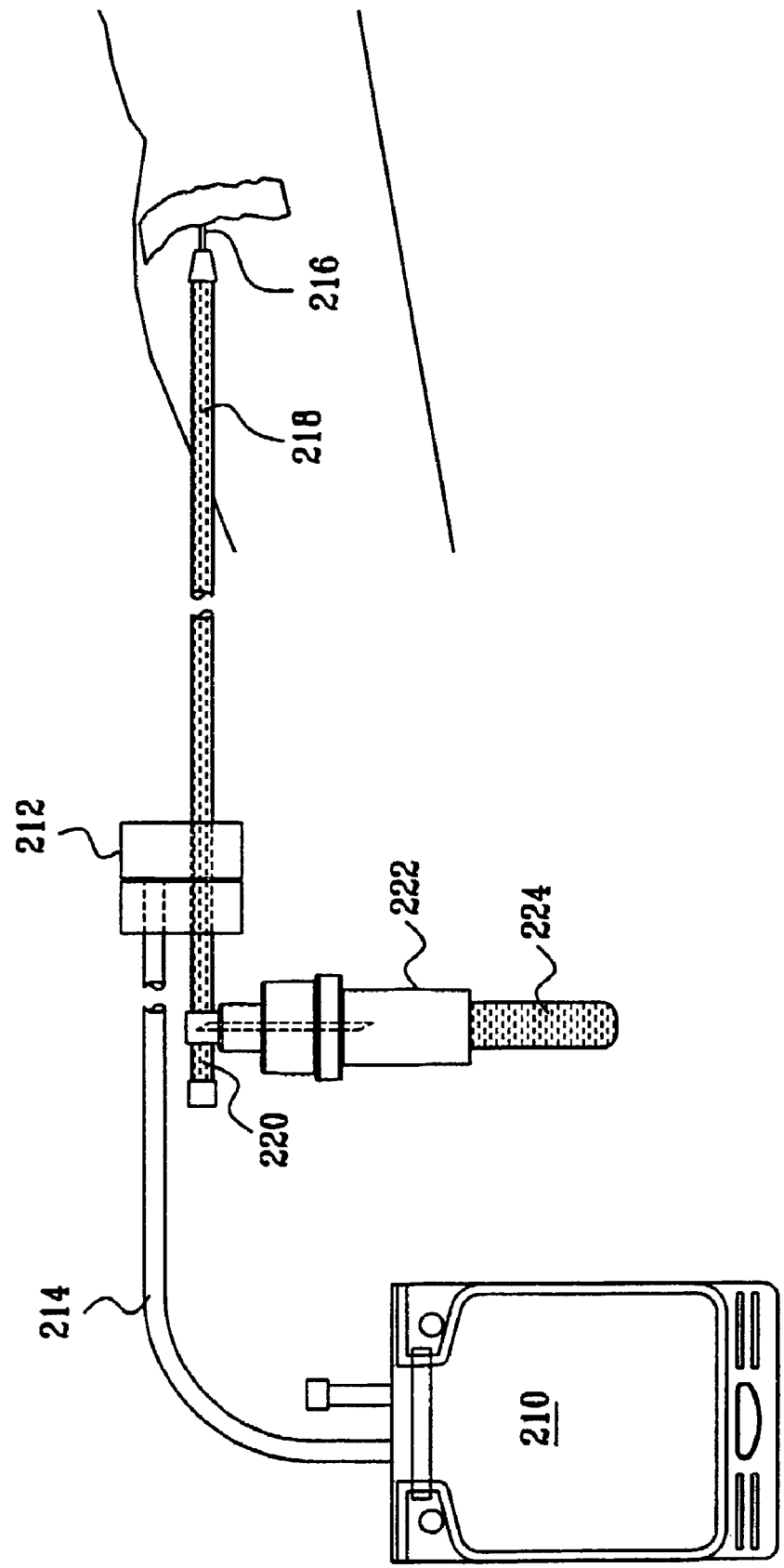

As seen in FIG. 14C, a sampling tube assembly 222, such as a sampling tube assembly described in applicant's Published PCT Patent Application WO 97/45714, the disclosure of which is hereby incorporated by reference, may be attached to sampling conduit 220. When a vacuum sampling tube 224 is operatively engaged with assembly 222, as shown in FIG. 14D, blood from the donor fills the tube 224 as well as sampling conduit 220 and supply conduit 218.

At this stage as shown in FIG. 14E, sampling tube 224 is disengaged from assembly 222 and valve 212 may be operated to decouple supply conduit 218 from sampling conduit 220 and to couple supply conduit 218 to collection conduit 214, for filling collection bag 210.

Figure 15A:
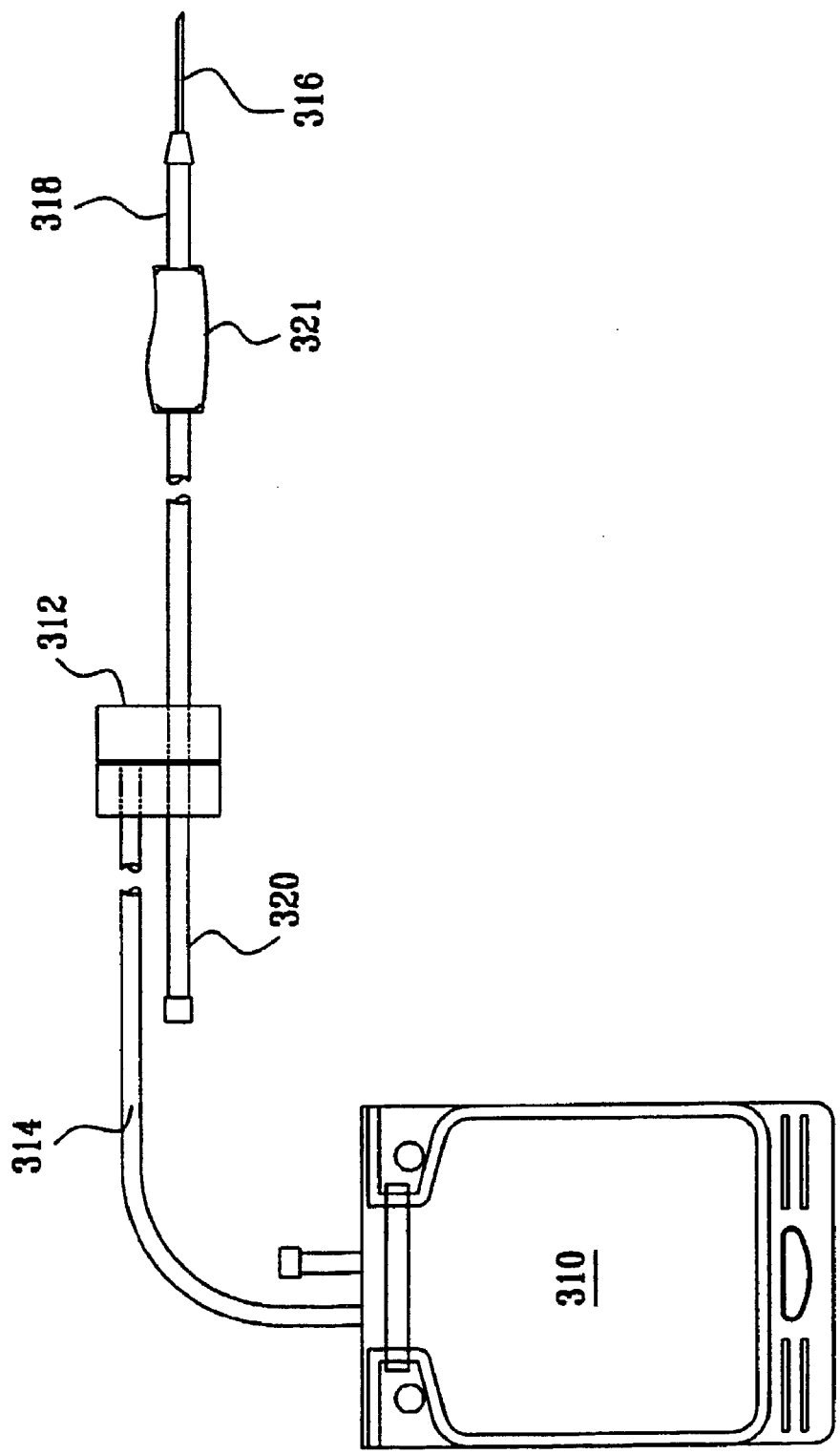

Reference is now made to FIGS. 15A, 15B, 15C, 15D and 15E, which are simplified illustrations of apparatus and a methodology for blood collection and sampling in accordance with another preferred embodiment of the present invention. As seen in FIG. 15A, a collection bag 310, such as a conventional collection bag commercially available from Teva Medical Ltd. of Ashdod, Israel, is connected to a rotatable sampling valve 312 via a collection conduit 314. A collection needle 316 is coupled to sampling valve 312 via a supply conduit 318. A sampling conduit 320 is also coupled to sampling valve 312. Valve 312 is operative to selectably couple the supply conduit 318 to either but not both of collection conduit 314 and sampling conduit 320. As distinct from the embodiment of FIGS. 14A–14E, in the embodiment of FIGS. 15A–15E an expandable element 321 is provided along supply conduit 318. This expandable element 321 is typically a relatively small collapsed plastic bag, which when expanded, can hold 2–3 ml of fluid.

Figure 15B:
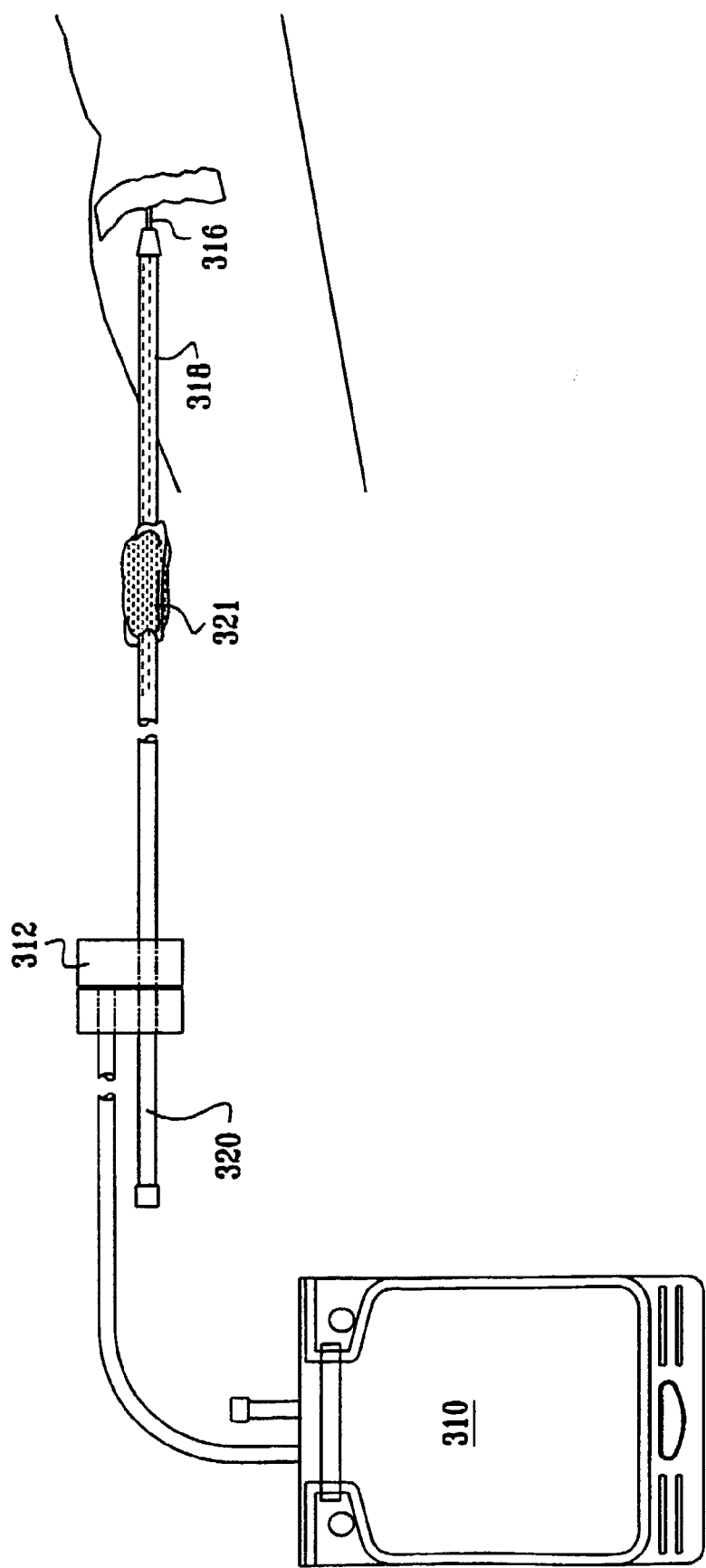

As seen in FIG. 15B, when the needle 316 is initially inserted into a donor's vein, and the valve 312 is initially positioned so as to couple supply conduit 318 to sampling conduit 320, due to provision of the expandable element 321, the donor's blood fills the expandable element 321, the supply conduit 318 upstream thereof and only a small portion of supply conduit 318 downstream thereof.

Figure 15D:
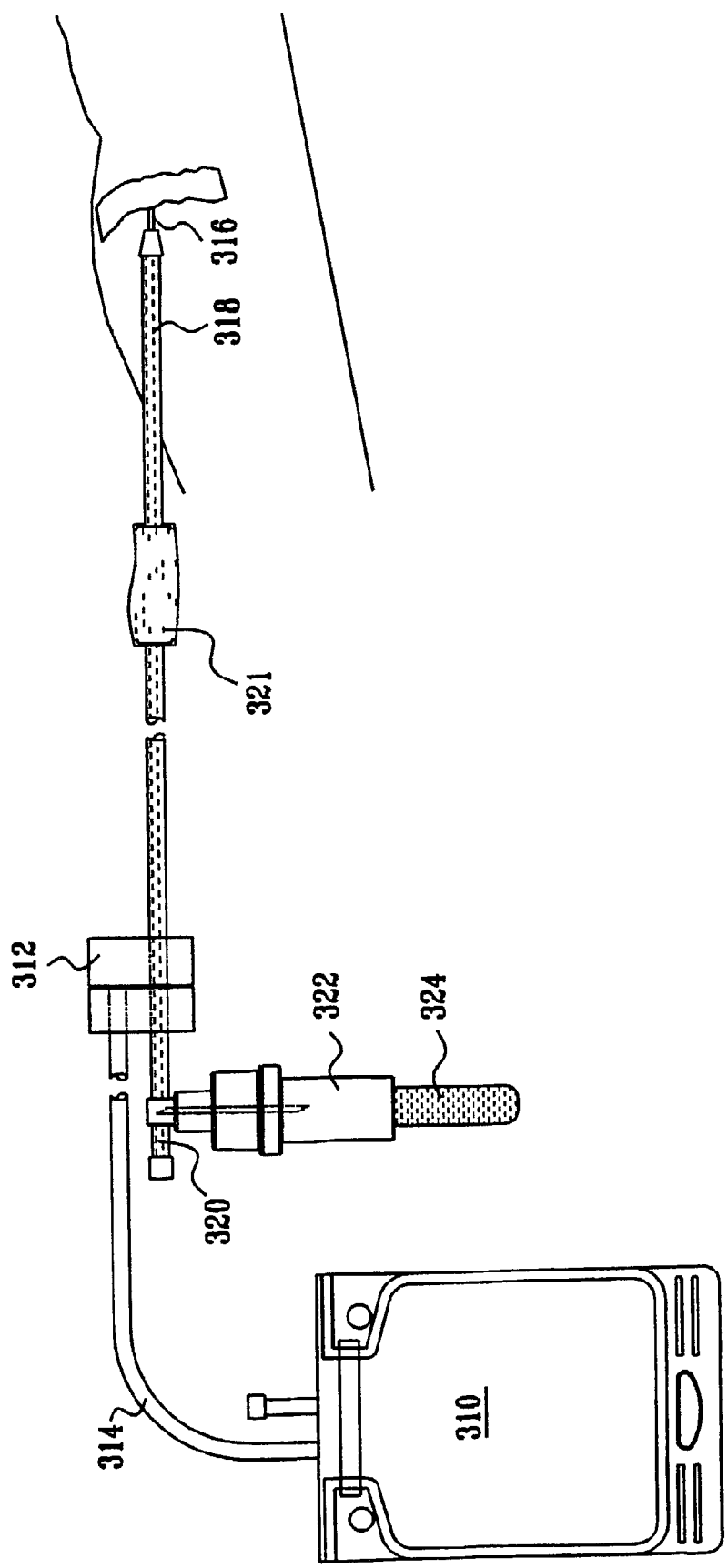

As seen in FIG. 15C, a sampling tube assembly 322, such as a sampling tube assembly described in applicant's Published PCT Patent Application WO 97/45714, the disclosure of which is hereby incorporated by reference, may be attached to sampling conduit 320. When a vacuum sampling tube 324 is operatively engaged with assembly 322, as shown in FIG. 15D, blood from the donor fills the tube 324 as well as sampling conduit 320, the expandable element 321 and the entire supply conduit 318.

At this stage, as shown in FIG. 15E, sampling tube 324 is disengaged from assembly 322 and valve 312 may be operated to decouple supply conduit 318 from sampling conduit 320 and to couple supply conduit 318 to collection conduit 314, for filling collection bag 310. During filling of collection bag 310, expandable element 321 may, contract somewhat.

Figure 16B:
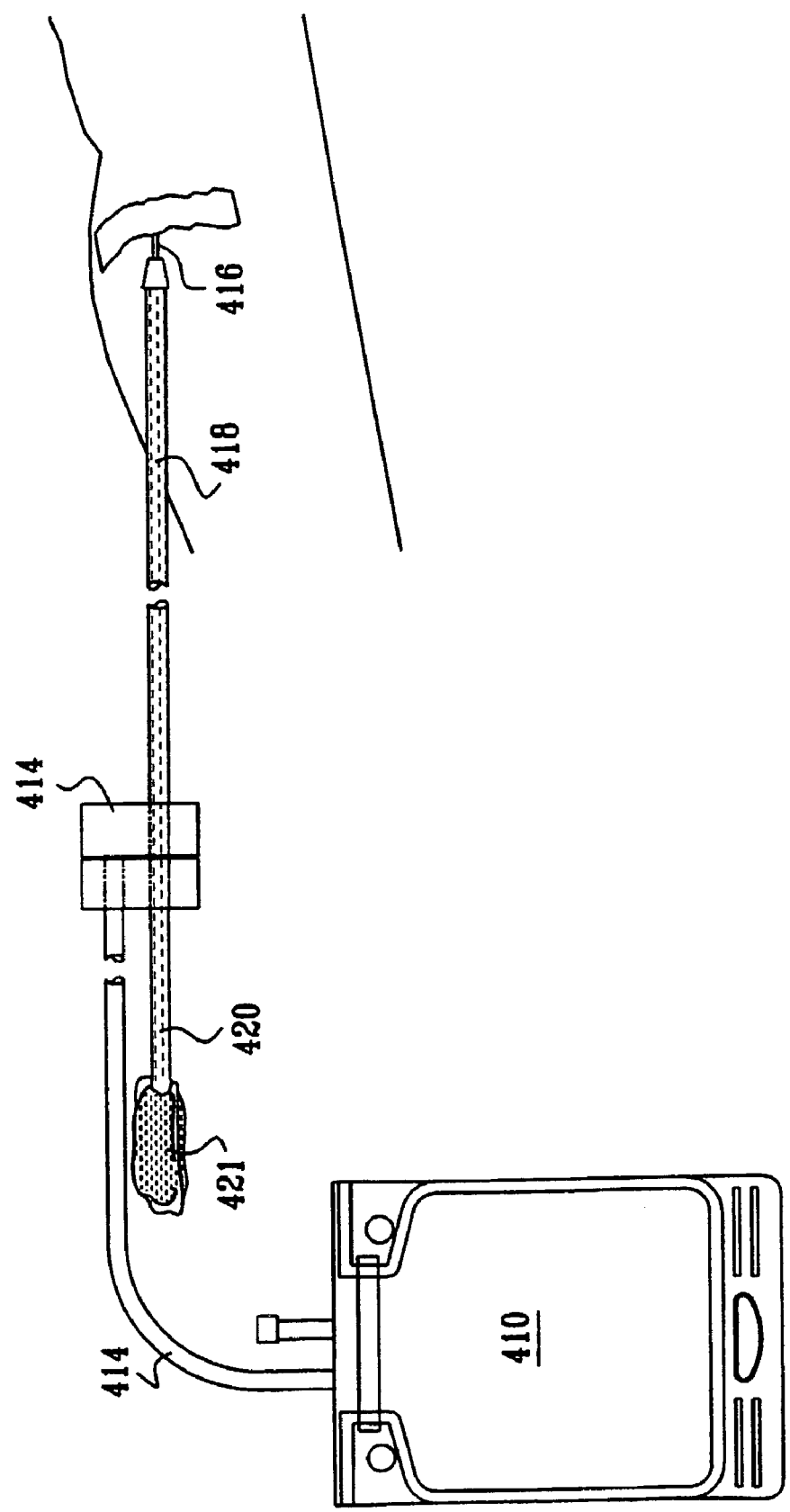

Reference is now made to FIGS. 16A, 16B, 16C, 16D and 16E, which are simplified illustrations of apparatus and a methodology for blood collection and sampling in accordance with yet another preferred embodiment of the present invention. As seen in FIG. 16A, a collection bag 410, such as a conventional collection bag commercially available from Teva Medical Ltd. of Ashdod, Israel, is connected to a rotatable sampling valve 412 via a collection conduit 414. A collection needle 416 is coupled to sampling valve 412 via a supply conduit 418. A sampling conduit 420 is also coupled to sampling valve 412. Valve 412 is operative to selectably couple the supply conduit 418 to either but not both of collection conduit 414 and sampling conduit 420. As distinct from the embodiment of FIGS. 15A–15E, in the embodiment of FIGS. 16A–16E an expandable element 421 is provided at the end of sampling conduit 420. This expandable element 421 is typically a relatively small collapsed plastic bag, which when expanded, can hold 2–3 ml of fluid.

As seen in FIG. 16B, when the needle 416 is initially inserted into a donor's vein, and the valve 412 is initially positioned so as to couple supply conduit 418 to sampling conduit 420, due to provision of the expandable element 421, the donor's blood fills the expandable element 421, sampling conduit 420 and supply conduit 418.

Figure 16C:
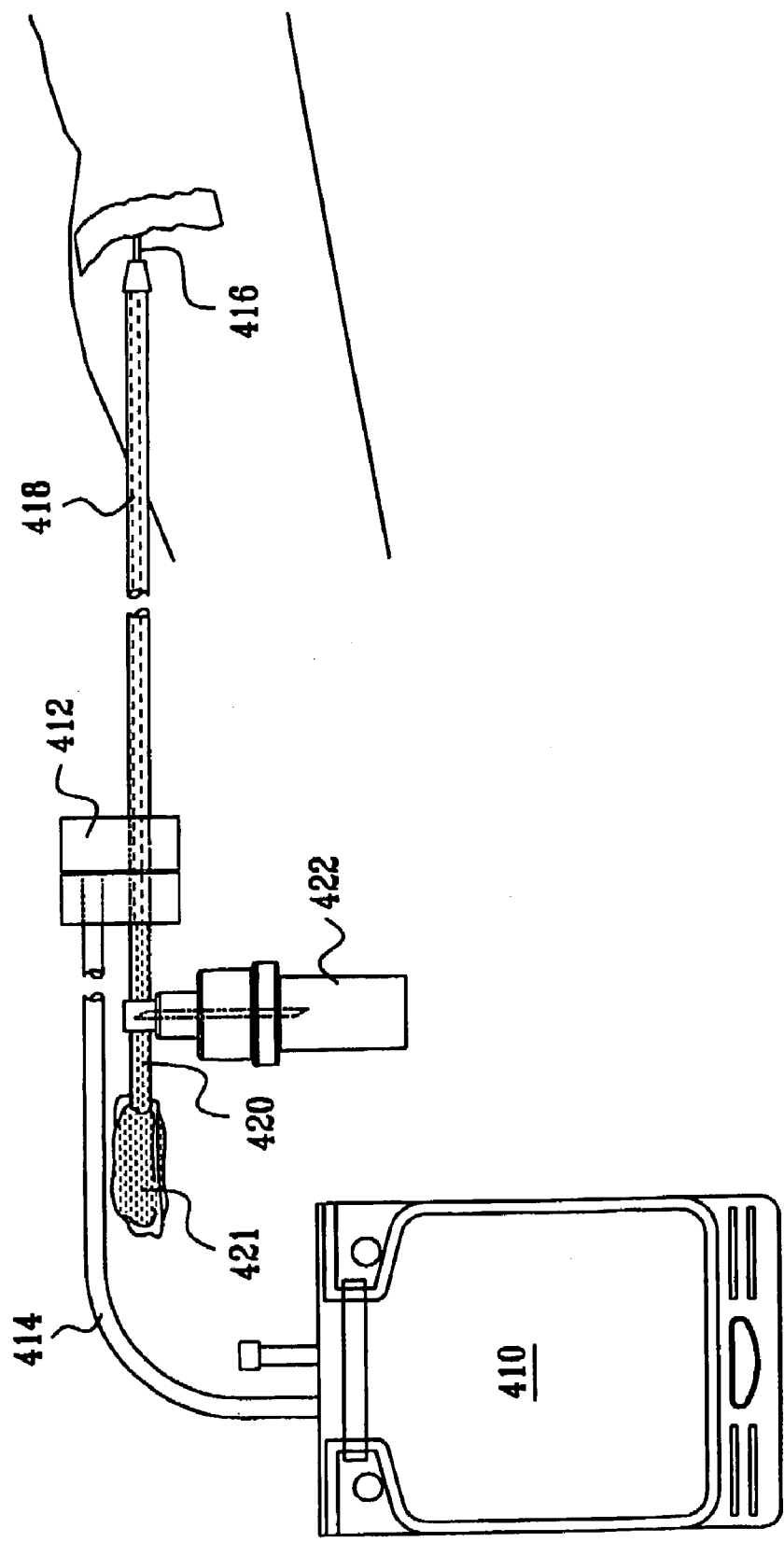
Figure 16D:
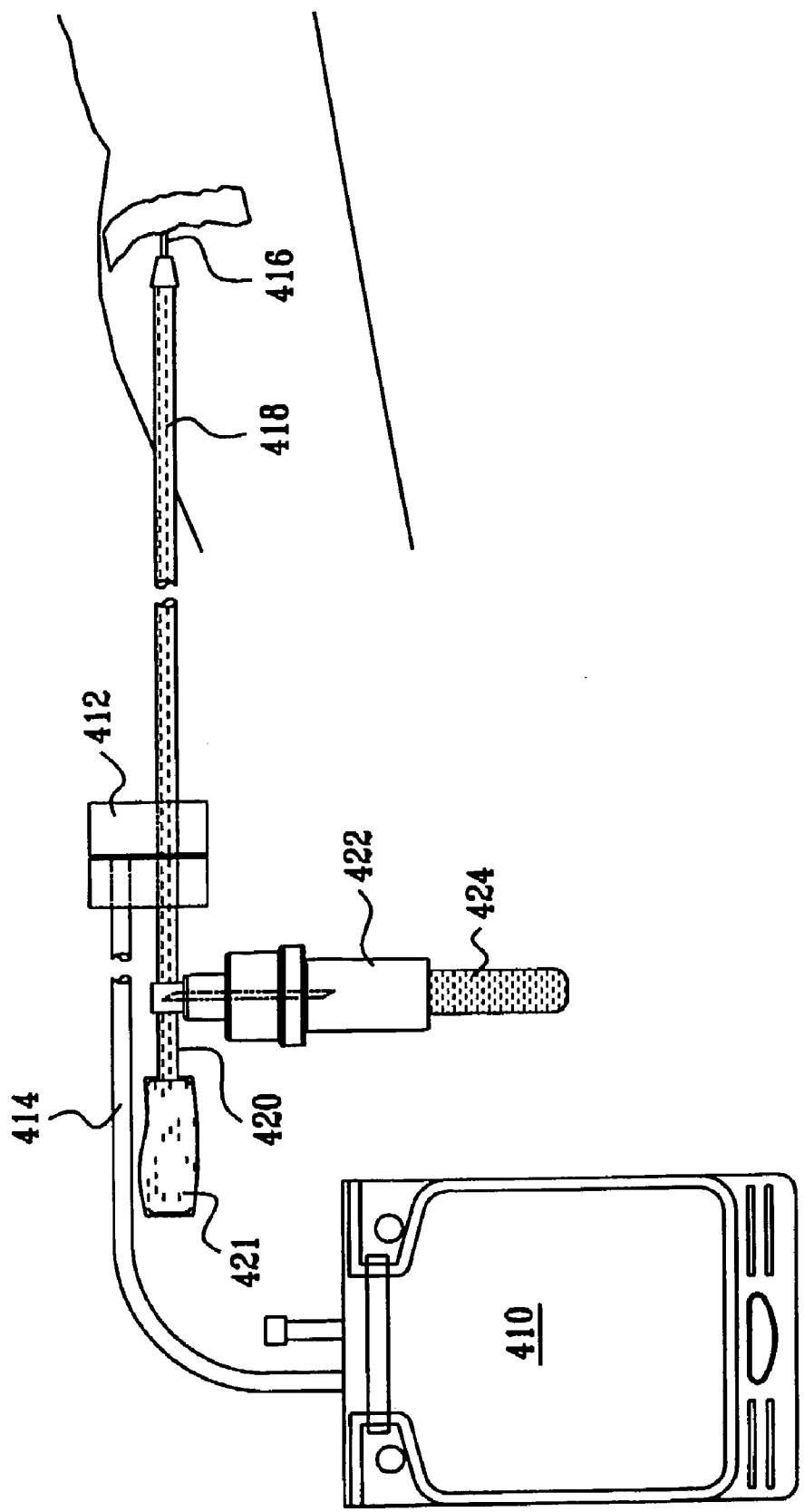

As seen in FIG. 16C, a sampling tube assembly 422, such as a sampling tube assembly described in applicant's Published PCT Patent Application WO 97/45714, the disclosure of which is hereby incorporated by reference, may be attached to sampling conduit 420. When a vacuum sampling tube 424 is operatively engaged with assembly 422, as shown in FIG. 16D, blood from the donor fills the tube 424 as well as sampling conduit 420, the expandable element 421 and supply conduit 418.

Figure 16E:
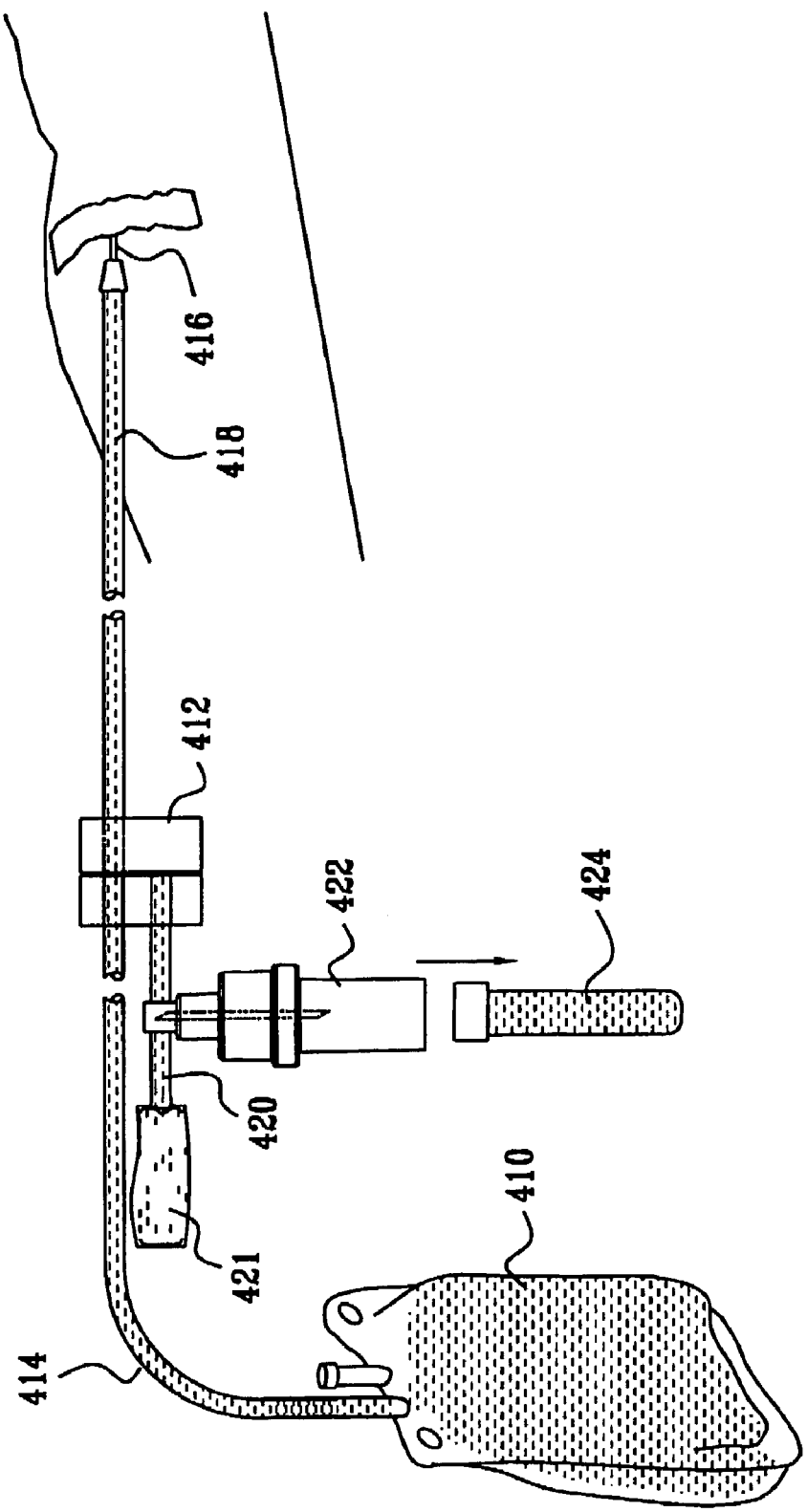

At this stage, as shown in FIG. 16E, sampling tube 424 is disengaged from assembly 422 and valve 412 may be operated to decouple supply conduit 418 from sampling conduit 420 and to couple supply conduit 418 to collection conduit 414, for filling collection bag 410. During filling of collection bag 410, expandable element 421 may contract somewhat.

Figure 17A:
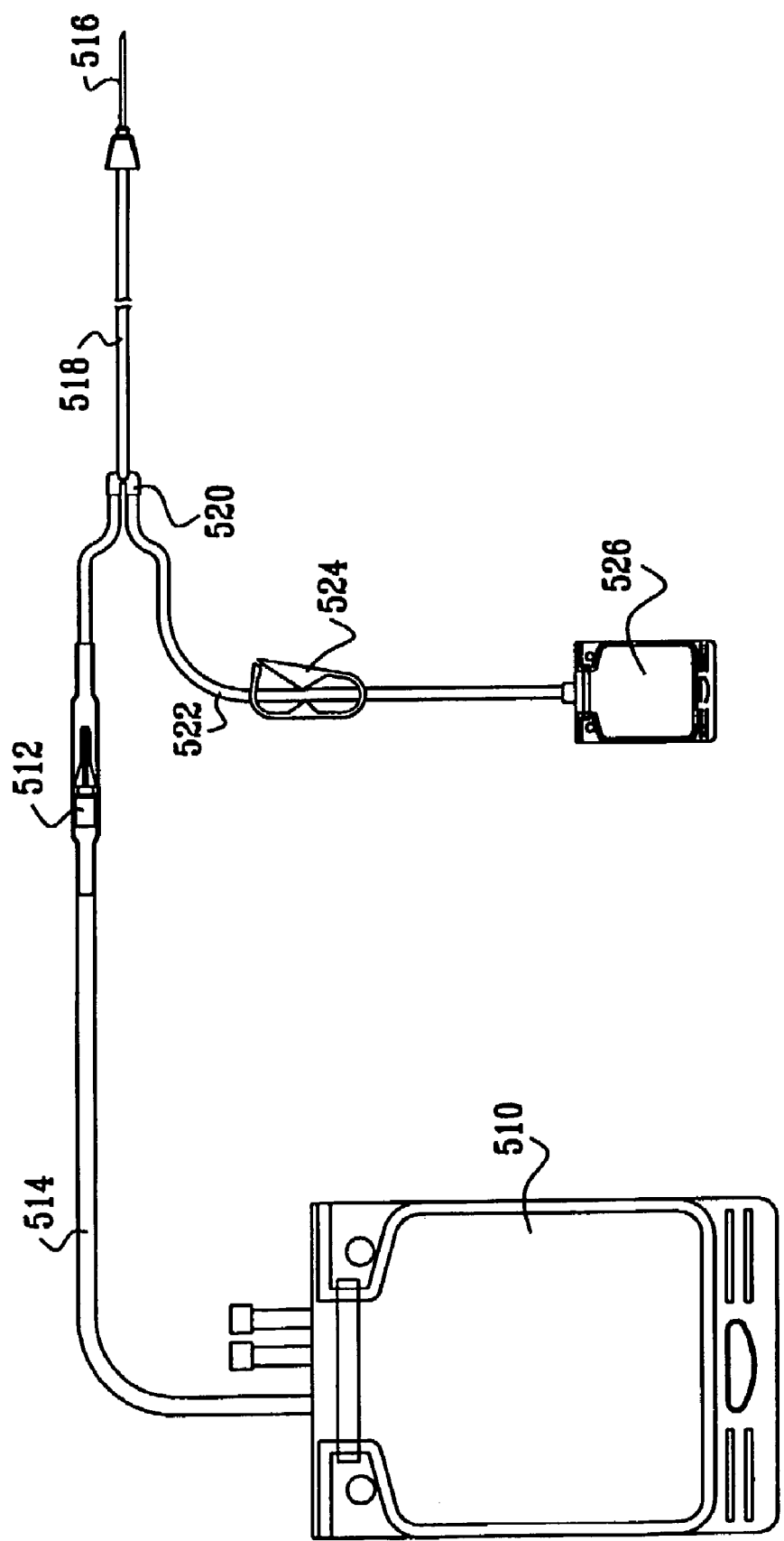
FIGS. 17A, 17B, 17C, 17D, 17E and 17F are simplified illustrations of apparatus and a methodology for blood collection and sampling in accordance with still another preferred embodiment of the present invention.

Reference is now made to FIGS. 17A, 17B, 17C, 17D, 17E and 17F, which are simplified illustrations of apparatus and a methodology for blood collection and sampling in accordance with yet another preferred embodiment of the present invention. As seen in FIG. 17A, a collection bag 510, such as a conventional collection bag commercially available from Teva Medical Ltd. of Ashdod, Israel, is connected to a conventional breakaway cannula 512 via a collection conduit 514. A collection needle 516 is coupled to breakaway cannula 512 via a supply conduit 518 and via a Y-connector 520.

A sampling conduit 522 is also coupled to Y-connector 520 and extends via a clamp 524 to a sampling bag 526. Clamp 524, which is entirely conventional, when opened allows blood to flow from collection needle 516 via Y-connector 520 and sampling conduit 522 to sampling bag 526. When clamp 524 is closed, all fluid communication between the sampling bag 526 and the collection needle 516 is prevented.

Breakaway cannula 512 is operative, when intact, to block fluid communication between Y-connector 520 and collection bag 510 and is operative, when broken, to allow blood from collection needle 516 to flow through collection conduit 514 to collection bag 510.

Figure 17B:
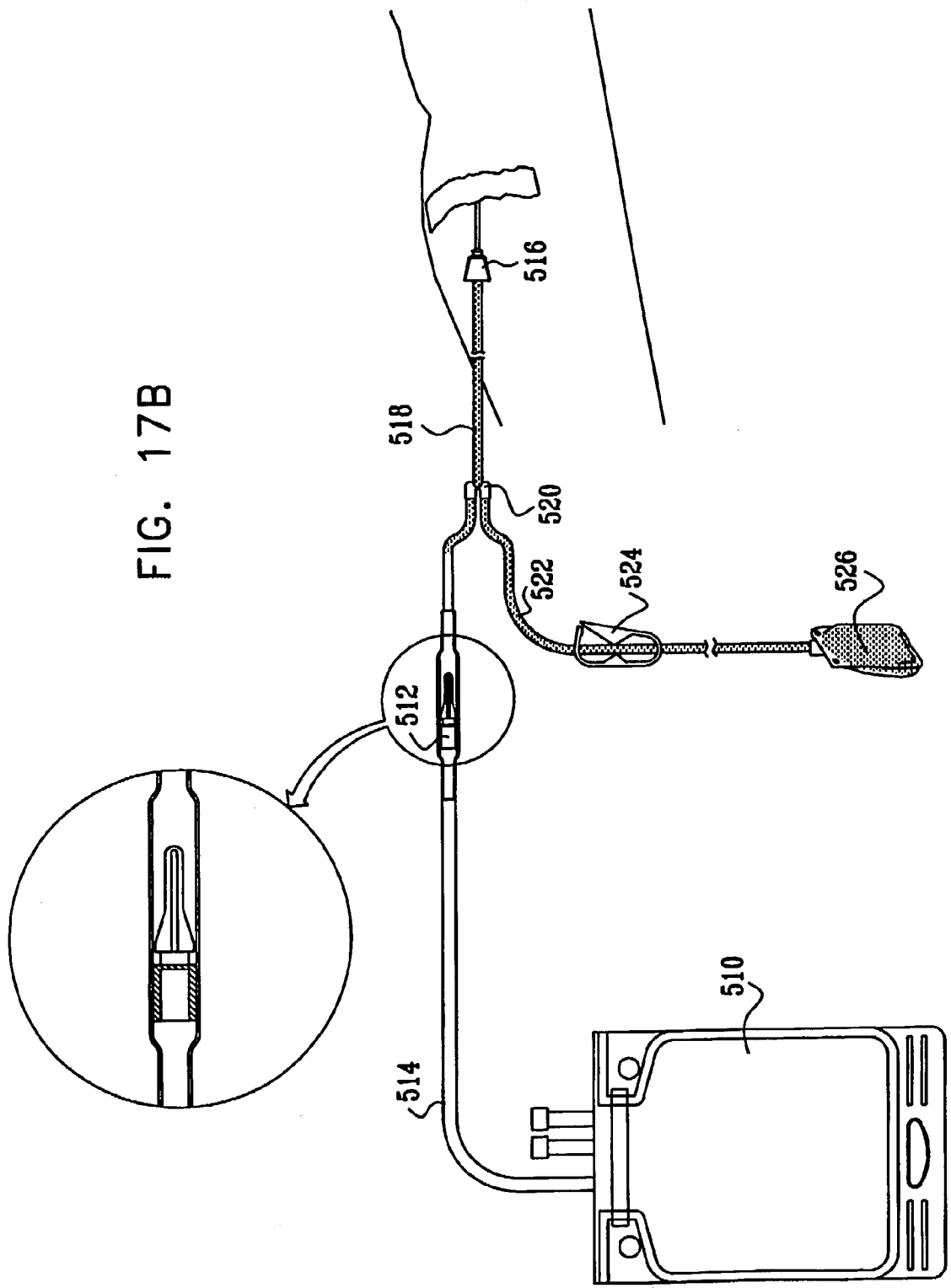

As seen in FIG. 17B, when the needle 516 is initially inserted into a donor's vein, while the breakaway cannula 512 is still intact and clamp 524 is open, the donor's blood fills the sampling bag 526.

Figure 17C:
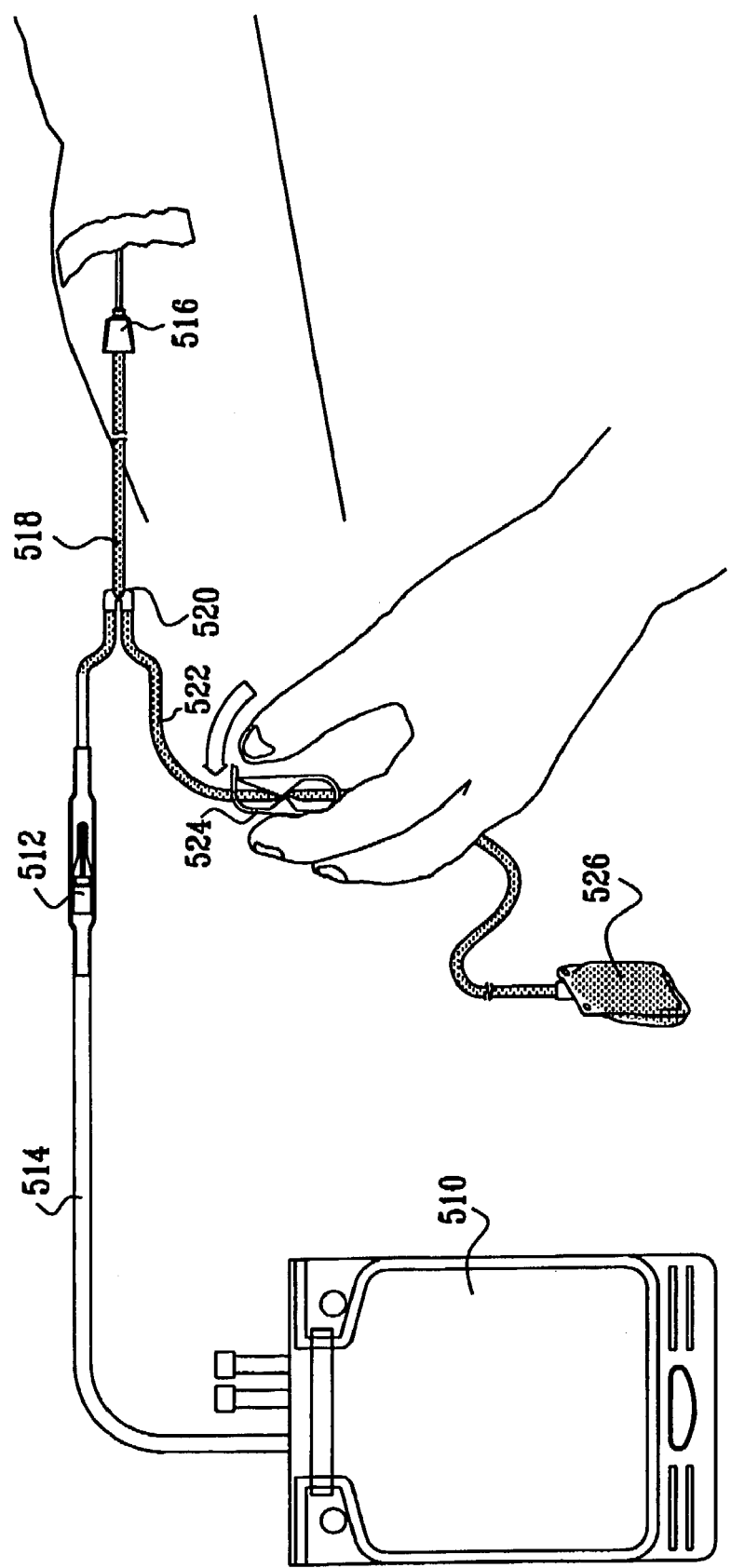

As seen in FIG. 17C, when the sampling bag 526 is filled, the clamp 524 is closed, thus blocking further fluid communication between the sampling bag 526 and the remainder of the apparatus shown in FIG. 17C.

Figure 17D:
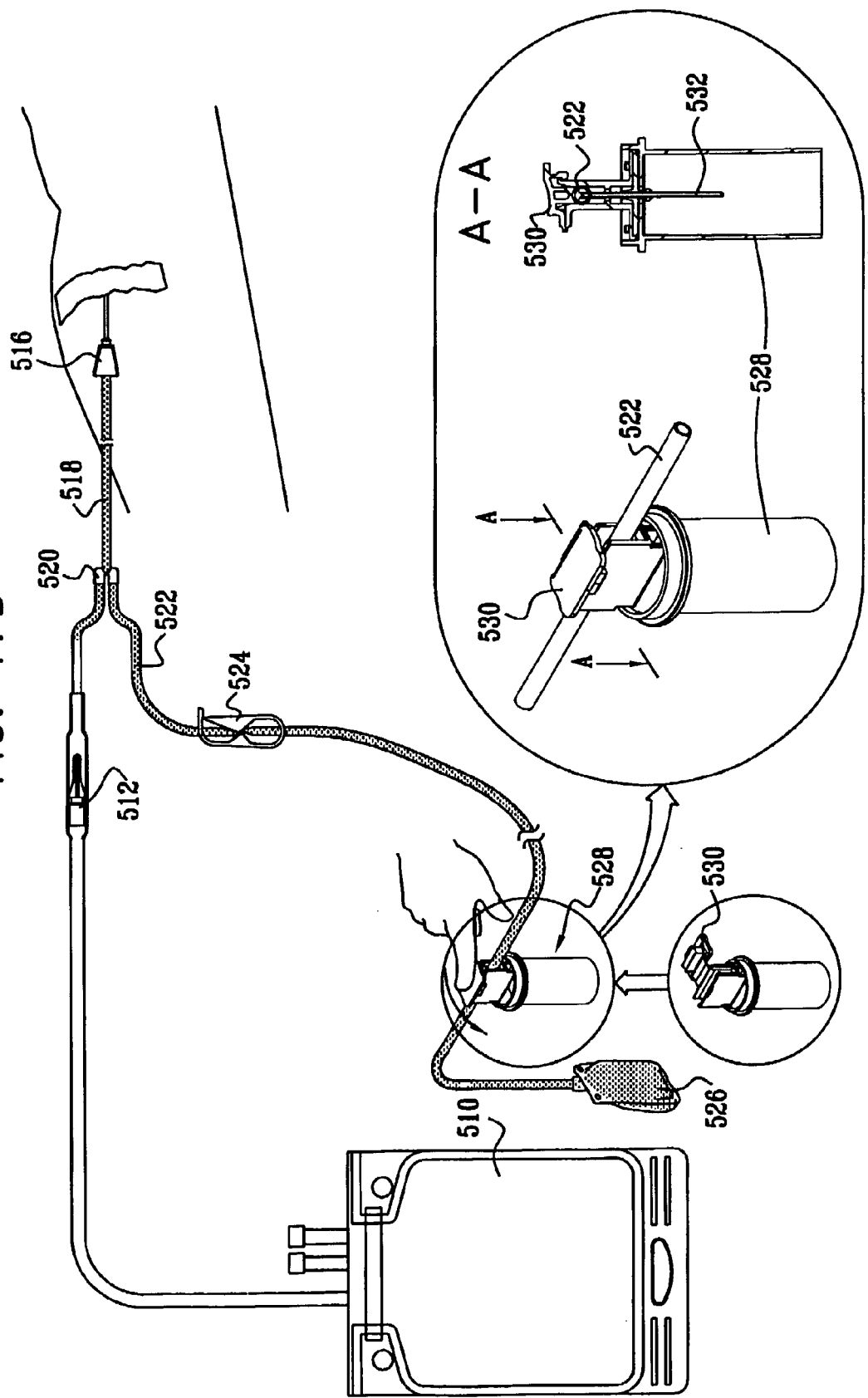

FIG. 17D shows operative engagement of a sampling tube assembly 528 to sampling conduit 522 downstream of clamp 524 and upstream of sampling bag 526. As noted above, the sampling tube assembly 528 is preferably constructed and operative in accordance with teachings contained in applicant's Published PCT Patent Application. WO 97/45714. the disclosure of which is hereby incorporated by reference. Such engagement includes attachment of the sampling tube assembly 528 to sampling conduit 522 as well closure of a clamping element 530, causing piercing of the sampling conduit 522 by a needle 532 in sampling tube assembly 528, thereby providing fluid communication with blood from sampling bag 526 and from conduit 522 downstream of clamp 524 and the interior of the needle 532.

Figure 17E:
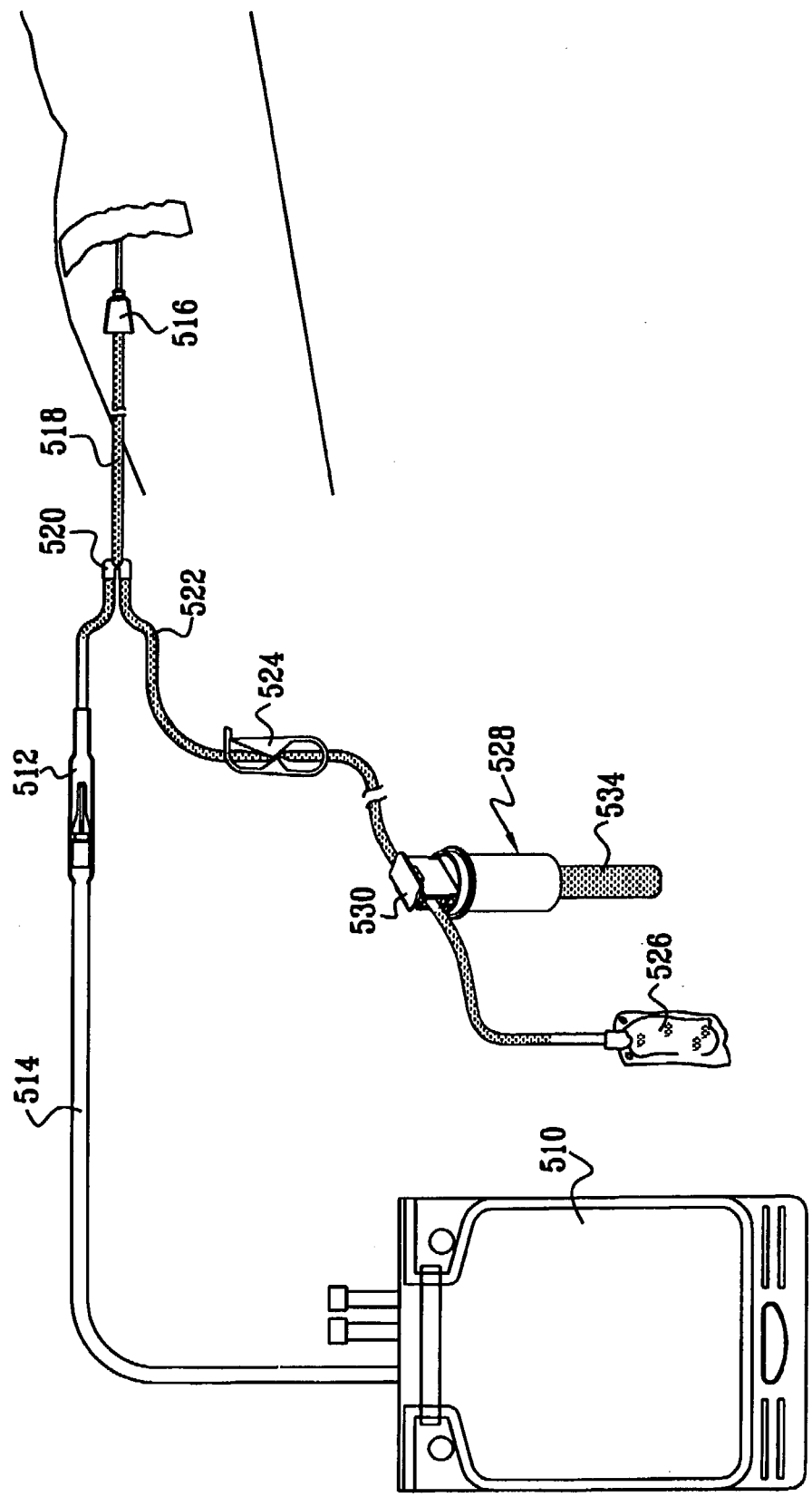

FIG. 17E shows operative engagement of a vacuum sampling tube 534 with sampling tube assembly 528. As a result of this engagement, needle 532 (FIG. 17D) communicates with the interior of the tube 534 and allows blood from sampling bag 526 and from conduit 522 downstream of clamp 524 to fill the tube 534. This at least partially empties sampling bag 526.

Figure 17F:
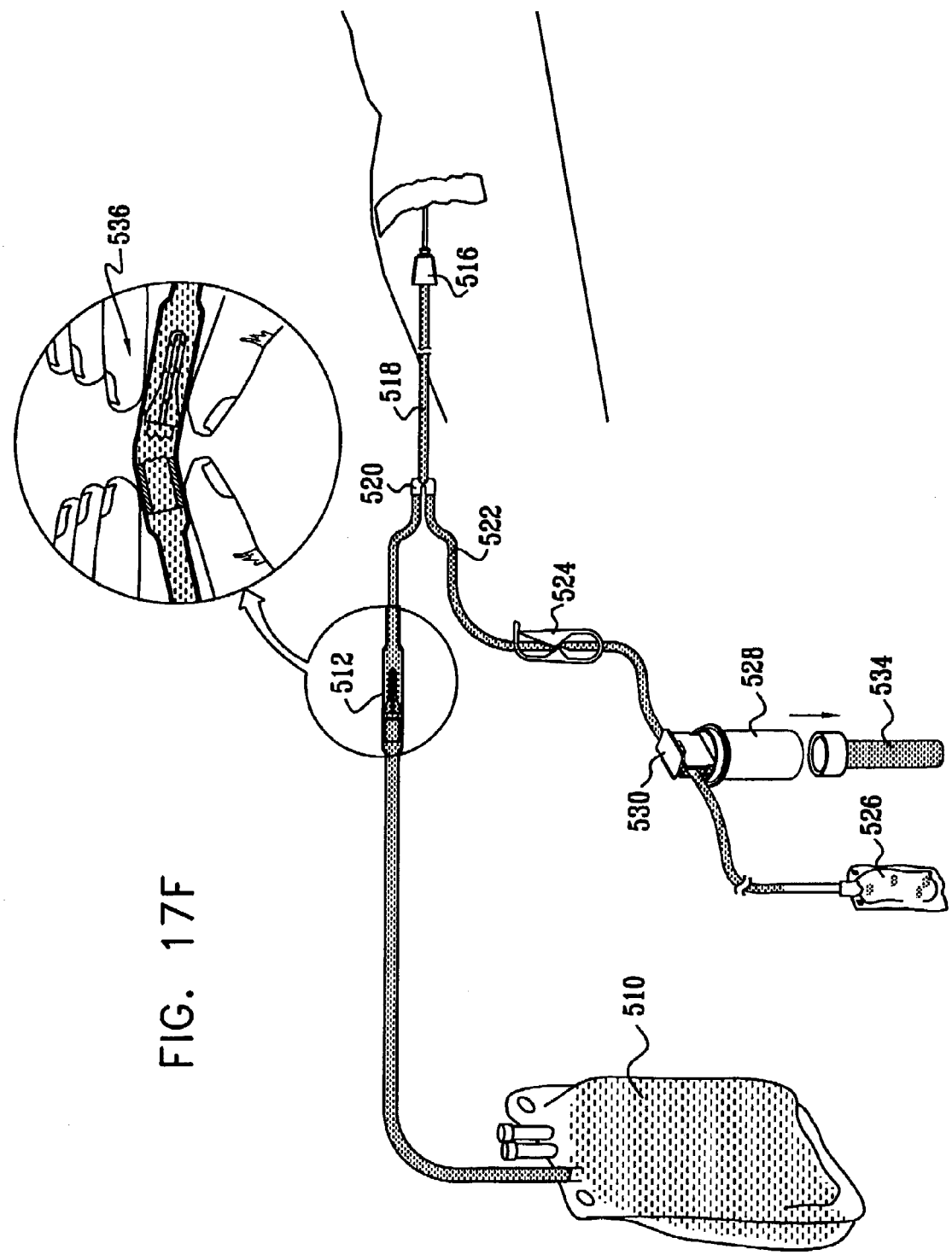

At this stage, as shown in FIG. 17F, sampling tube 534 may be disengaged from assembly 528 and breakaway cannula 512 may be broken as indicated at reference numeral 536 to allow blood flow from needle 516, via Y-connector 520, via broken breakaway cannula 512 and collection conduit 514 to fill collection bag 510.

Figure 18A:
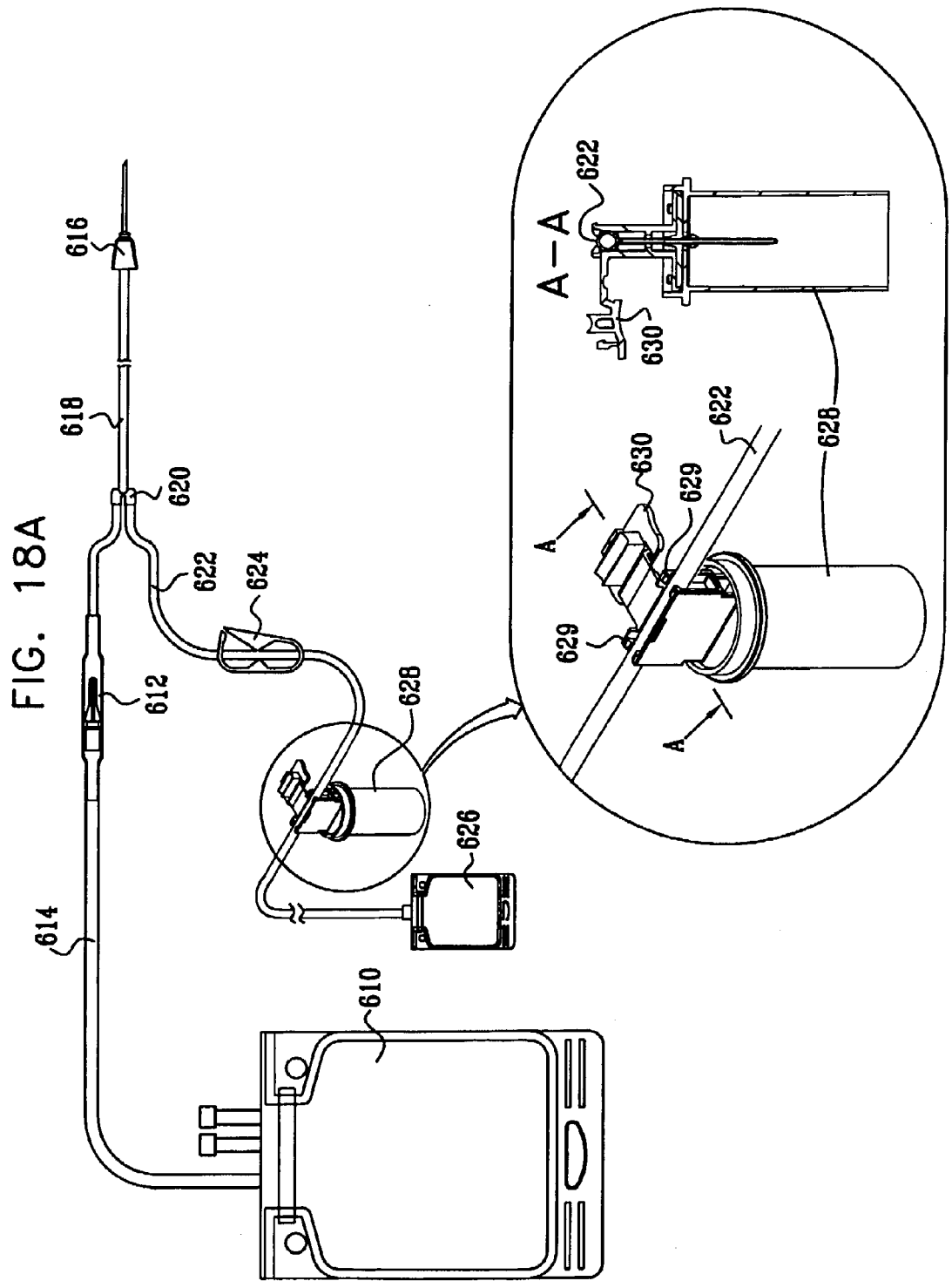

Reference is now made to FIGS. 18A, 18B, 18C, 18D, 18E and 18F, which are simplified illustrations of apparatus and a methodology for blood collection and sampling in accordance with still another preferred embodiment of the present invention. As seen in FIG. 18A, a collection bag 610, such as a conventional collection bag commercially available from Teva Medical Ltd. of Ashdod, Israel, is connected to a conventional breakaway cannula 612 via a collection conduit 614. A collection needle 616 is coupled to breakaway cannula 612 via a supply conduit 618 and via a Y-connector 620.

A sampling conduit 622 is also coupled to Y-connector 620 and extends via a clamp 624 to a sampling bag 626. FIG. 18A also shows pre-attachment of a sampling tube assembly 628 to sampling conduit 622 downstream of clamp 624 and upstream of sampling bag 626. As noted above, the sampling tube assembly 628 is preferably constructed and operative in accordance with teachings contained in applicant's Published PCT Patent Application WO 97/45714, the disclosure of which is hereby incorporated by reference.

It is a particular feature of the present invention that the sampling tube assembly 628 includes the following structure which is not described in the aforesaid Published PCT Patent Application WO 97/45714. namely the provision of a plurality of retaining protrusions 629, which serve to retain the sampling tube assembly 628 in engagement with the sampling conduit 622, even before closure of a clamping element 630 thereof.

Clamp 624, which is entirely conventional, when opened allows blood to flow from collection needle 616 via Y-connector 620 and sampling conduit 622 to sampling bag 626 and to sampling tube assembly 628. When clamp 624 is closed, all fluid communication between the sampling bag 626 and the sampling tube assembly 628 on the one hand and the collection needle 616 on the other hand is prevented.

Breakaway cannula 612 is operative, when intact, to block fluid communication between Y-connector 620 and collection bag 610 and is operative, when broken, to allow blood from collection needle 616 to flow through collection conduit 614 to collection bag 610.

Figure 18B:
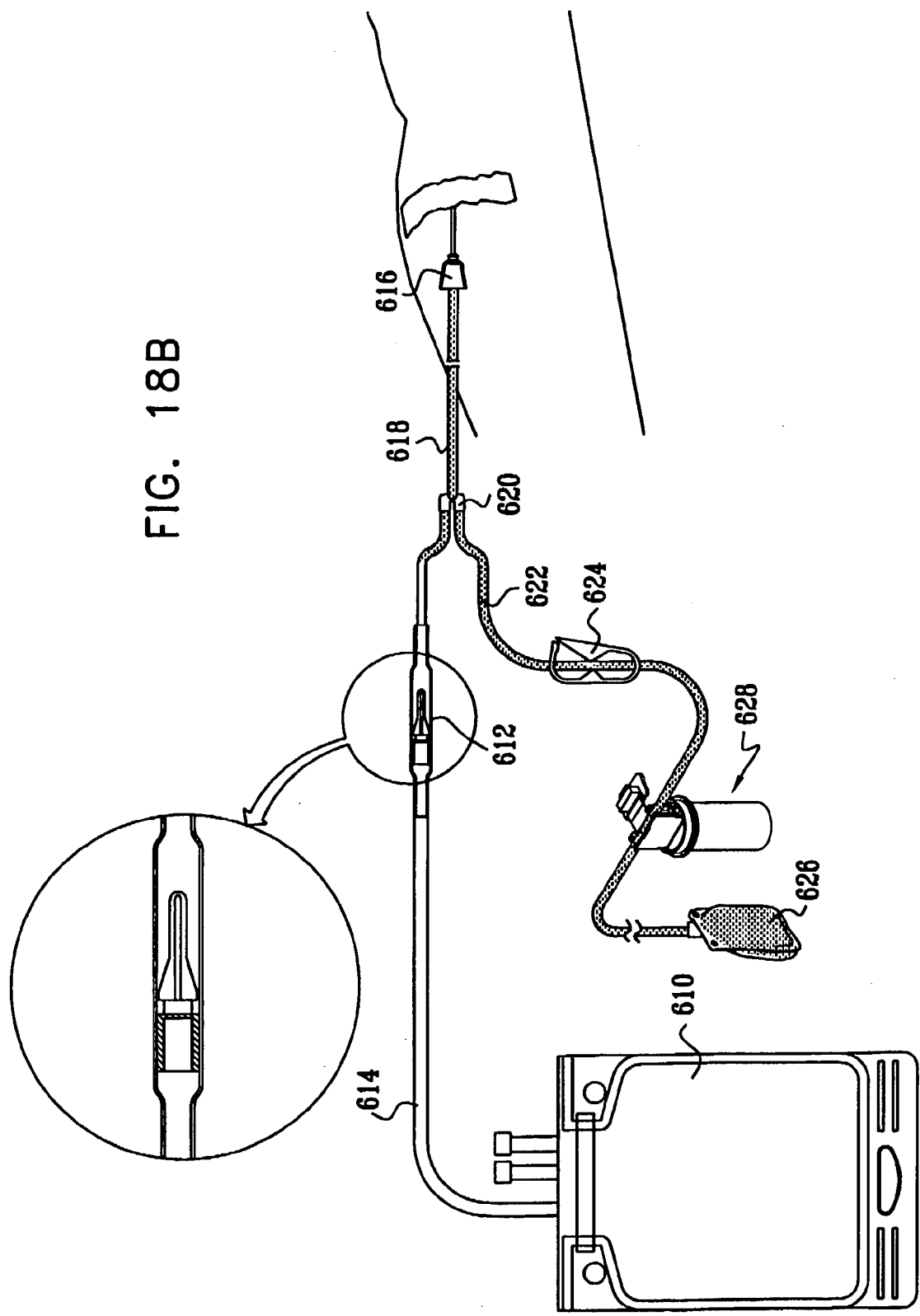

As seen in FIG. 18B, when the needle 616 is initially inserted into a donor's vein, while the breakaway cannula 612 is still intact and clamp 624 is open, the donor's blood fills the sampling bag 626.

As seen in FIG. 18C, when the sampling bag 626 is filled, the clamp 624 is closed, thus blocking further fluid communication between the sampling bag 626 and the sampling tube assembly 628 on the one hand and the remainder of the apparatus shown in FIG. 18C on the other hand.

Figure 18D:
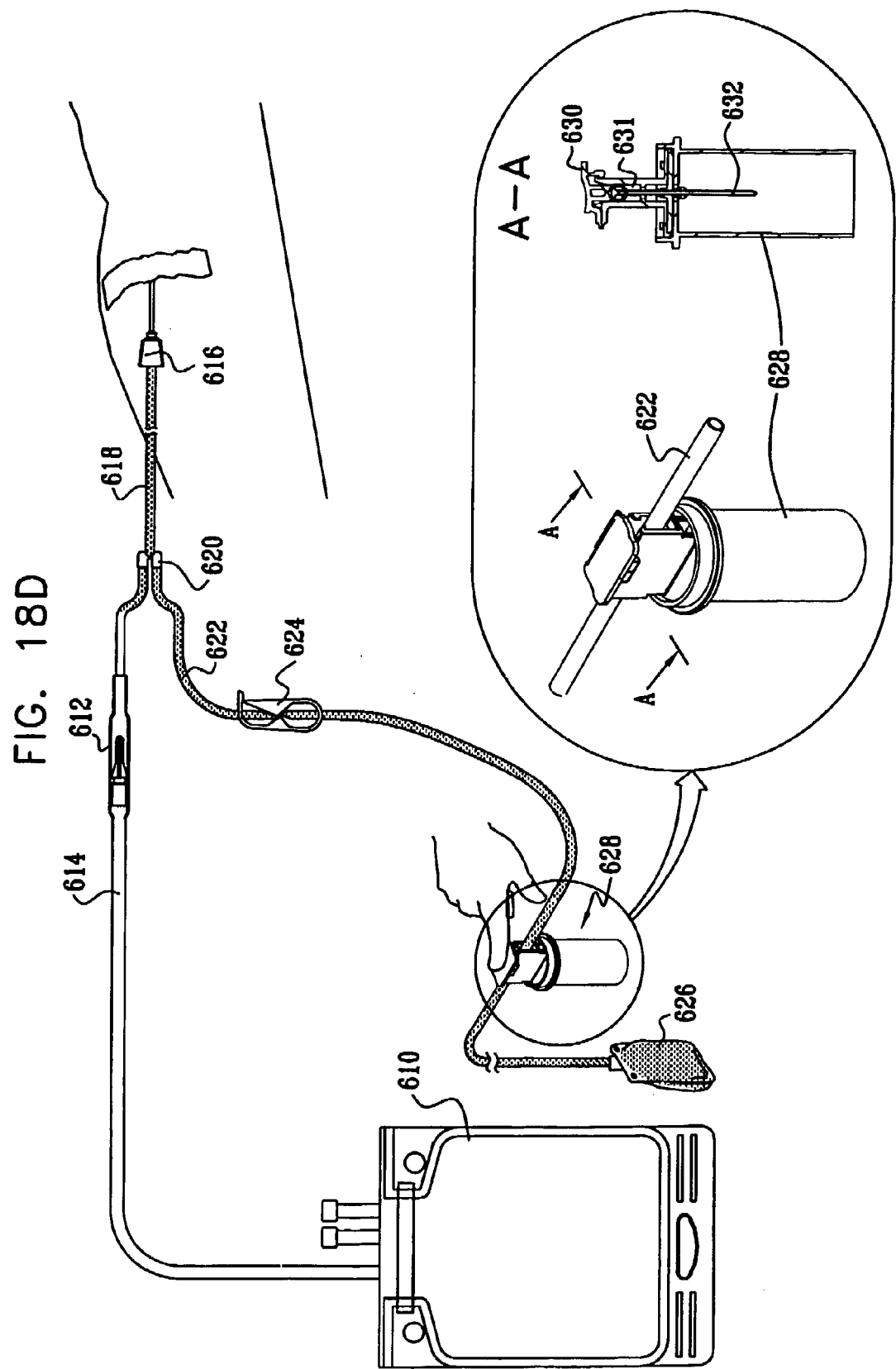

FIG. 18D shows operative engagement of the sampling tube assembly 628 to sampling conduit 622. As noted above, with reference to FIG. 18A, the sampling tube assembly 628 is pre-attached to sampling conduit 622.

In this connection, an additional feature of the sampling tube assembly 628, which is not described in the aforesaid Published PCT Patent Application WO 97/45714, is noted. A resilient material, such as a piece of foam rubber 631, is preferably provided around a sharp end of a needle 632 forming part of sampling tube assembly 628 in order to prevent inadvertent and premature puncturing of sampling conduit 622 by needle 632. The provision of foam rubber 631 has another advantage, namely, providing a seal against leakage from sampling conduit 622, once it has been punctured by needle 632.

As seen in FIG. 18D, closure of clamping element 630, causes piercing of the sampling conduit 622 by needle 632 in sampling tube assembly 628, thereby providing fluid communication with blood from sampling bag 626 and from conduit 622 downstream of clamp 624 and the interior of the needle 632.

Figure 18E:
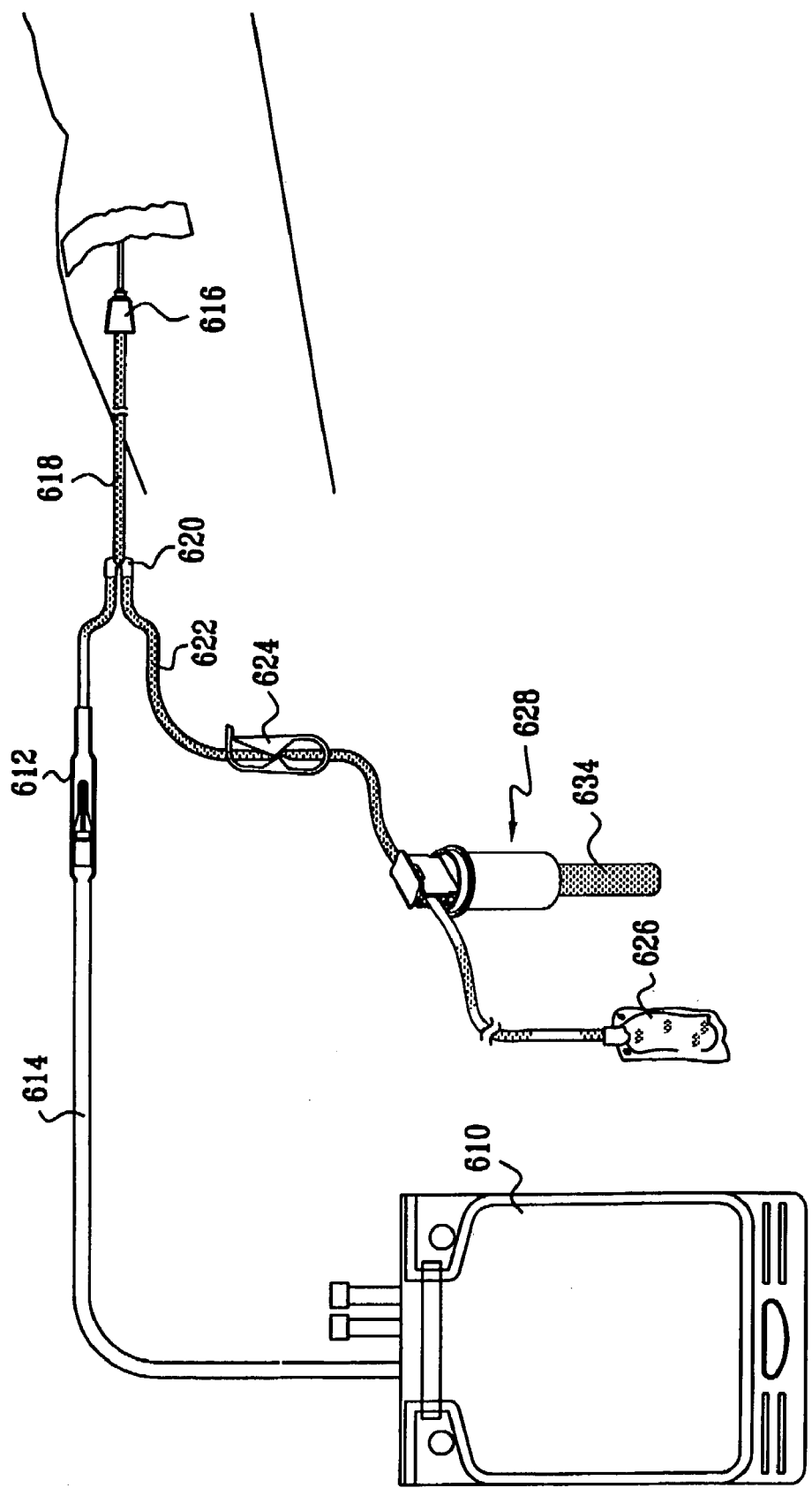

FIG. 18E shows operative engagement of a vacuum sampling tube 634 with sampling tube assembly 628. As a result of this engagement, needle 632 (FIG. 18D) communicates with the interior of the tube 634 and allows blood from sampling bag 626 and from conduit 622 downstream of clamp 624 to fill the tube 634. This at least partially empties sampling bag 626.

Figure 18F:
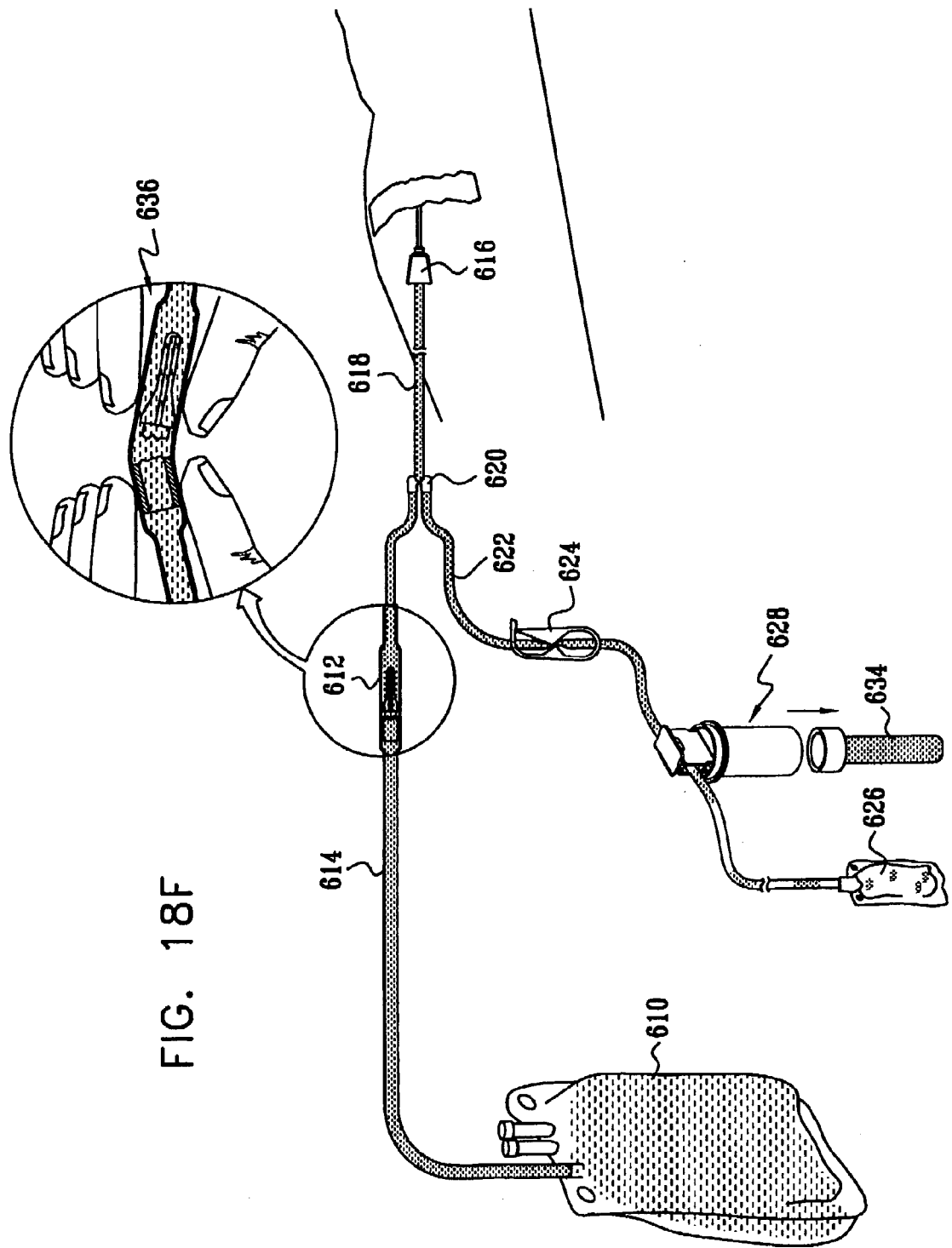

At this stage, as shown in FIG. 18F, sampling tube 634 may be disengaged from assembly 628 and breakaway cannula 612 may be broken as indicated at reference numeral 636 to allow blood flow from needle 616, via Y-connector 620, via broken breakaway cannula 612 and collection conduit 614 to fill collection bag 610.

Figure 19A:
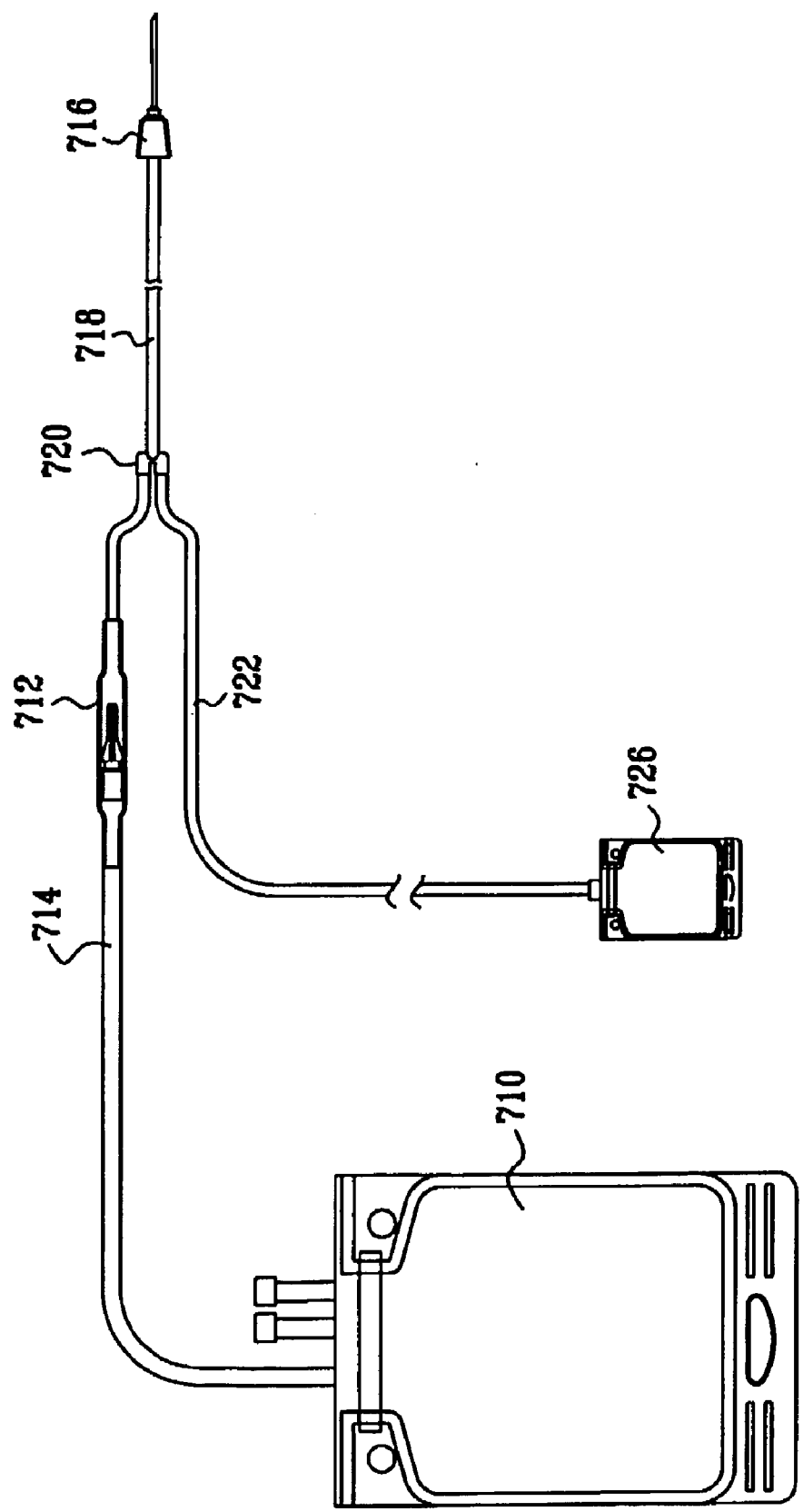
FIGS. 19A, 19B, 19C, 19D, 19E and 19F are simplified illustrations of apparatus and a methodology for blood collection and sampling in accordance with still another preferred embodiment of the present invention.

Reference is now made to FIGS. 19A, 19B, 19C, 19D, 19E and 19F, which are simplified illustrations of apparatus and a methodology for blood collection and sampling in accordance with yet another preferred embodiment of the present invention. As seen in FIG. 19A, a collection bag 710, such as a conventional collection bag commercially available from Teva Medical Ltd. of Ashdod, Israel, is connected to a conventional breakaway cannula 712 via a collection conduit 714. A collection needle 716 is coupled to breakaway cannula 712 via a supply conduit 718 and via a Y-connector 720.

A sampling conduit 722 is also coupled to Y-connector 720 and extends to a sampling bag 726.

Breakaway cannula 712 is operative, when intact, to block fluid communication between Y-connector 720 and collection bag 710 and is operative, when broken, to allow blood from collection needle 716 to flow through collection conduit 714 to collection bag 710.

Figure 19B:
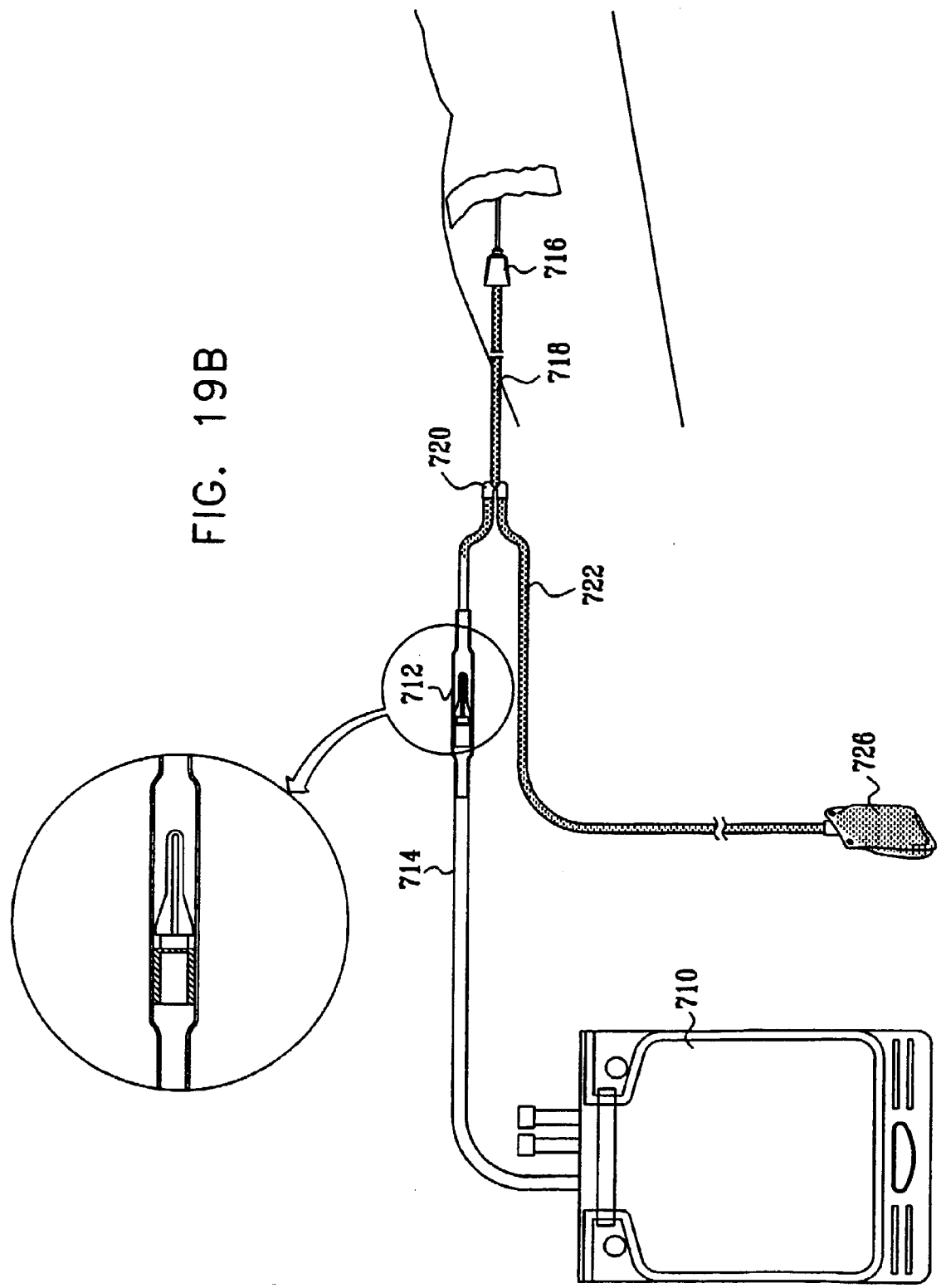

As seen in FIG. 19B, when the needle 716 is initially inserted into a donor's vein, while the breakaway cannula 712 is still intact, the donor's blood fills the sampling bag 726.

Figure 19C:
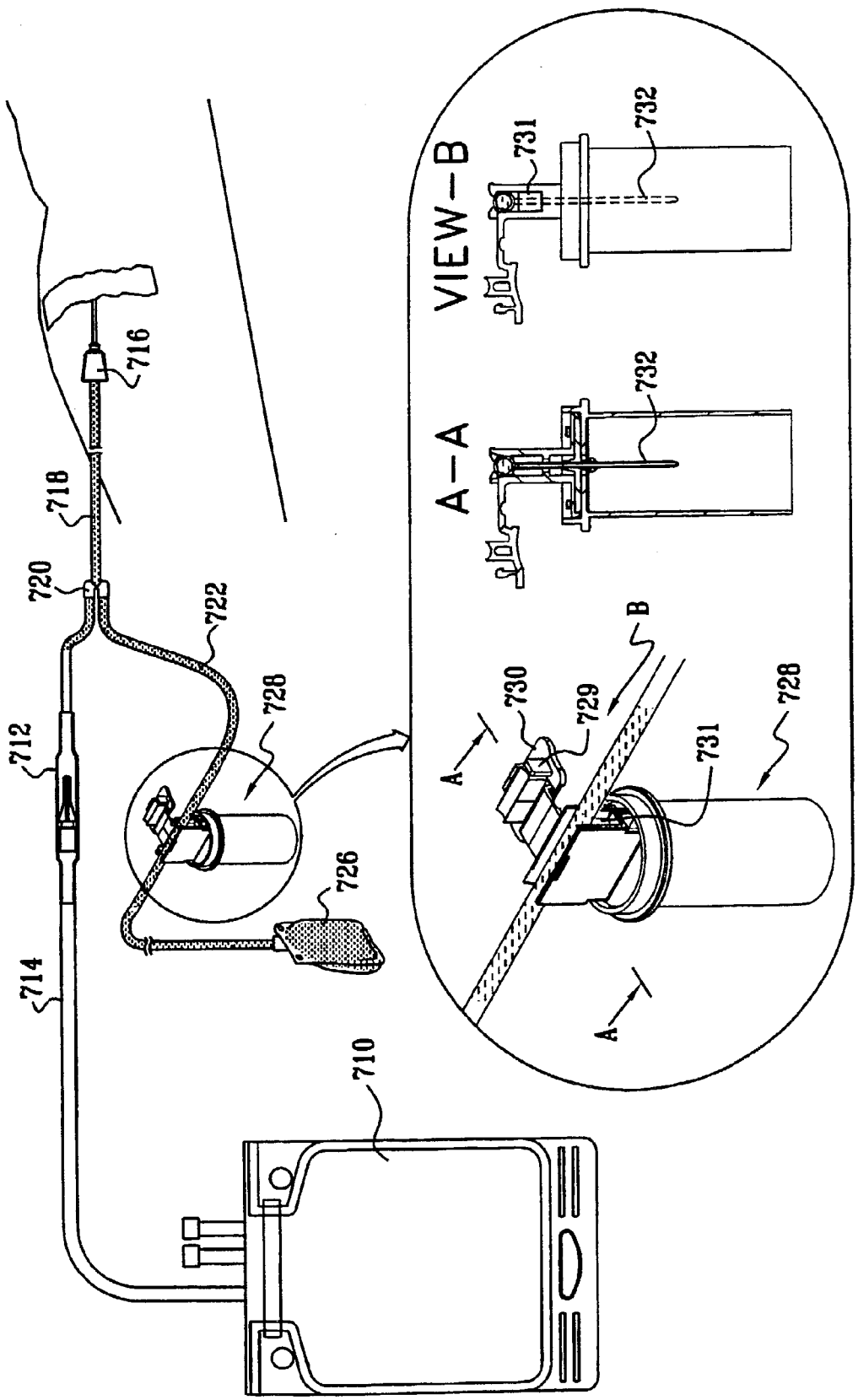

Reference is now made to FIG. 19C, which shows attachment of a sampling tube assembly 728 to sampling conduit 722 upstream of sampling bag 726. As noted above, the sampling tube assembly 728 is preferably constructed and operative in accordance with teachings contained in applicant's Published PCT Patent Application WO 97/45714, the disclosure of which is hereby incorporated by reference.

It is a particular feature of the present invention that the sampling tube assembly 728 includes the following structure which is not described in the aforesaid Published PCT Patent Application WO 97/45714, namely the provision of a clamping protrusion 729 on a clamping element 730 of sampling tube assembly 728 which cooperates with a clamping protrusion 731. The provision of clamping protrusions 729 and 731 obviates the need for a separate clamp, such as clamp 624 in the embodiment of FIGS. 18A–18F. The attachment of the sampling tube assembly 728 to the sampling conduit 722 may take place at any suitable time, prior to or following insertion of needle 716 into the donor's vein.

Figure 19D:
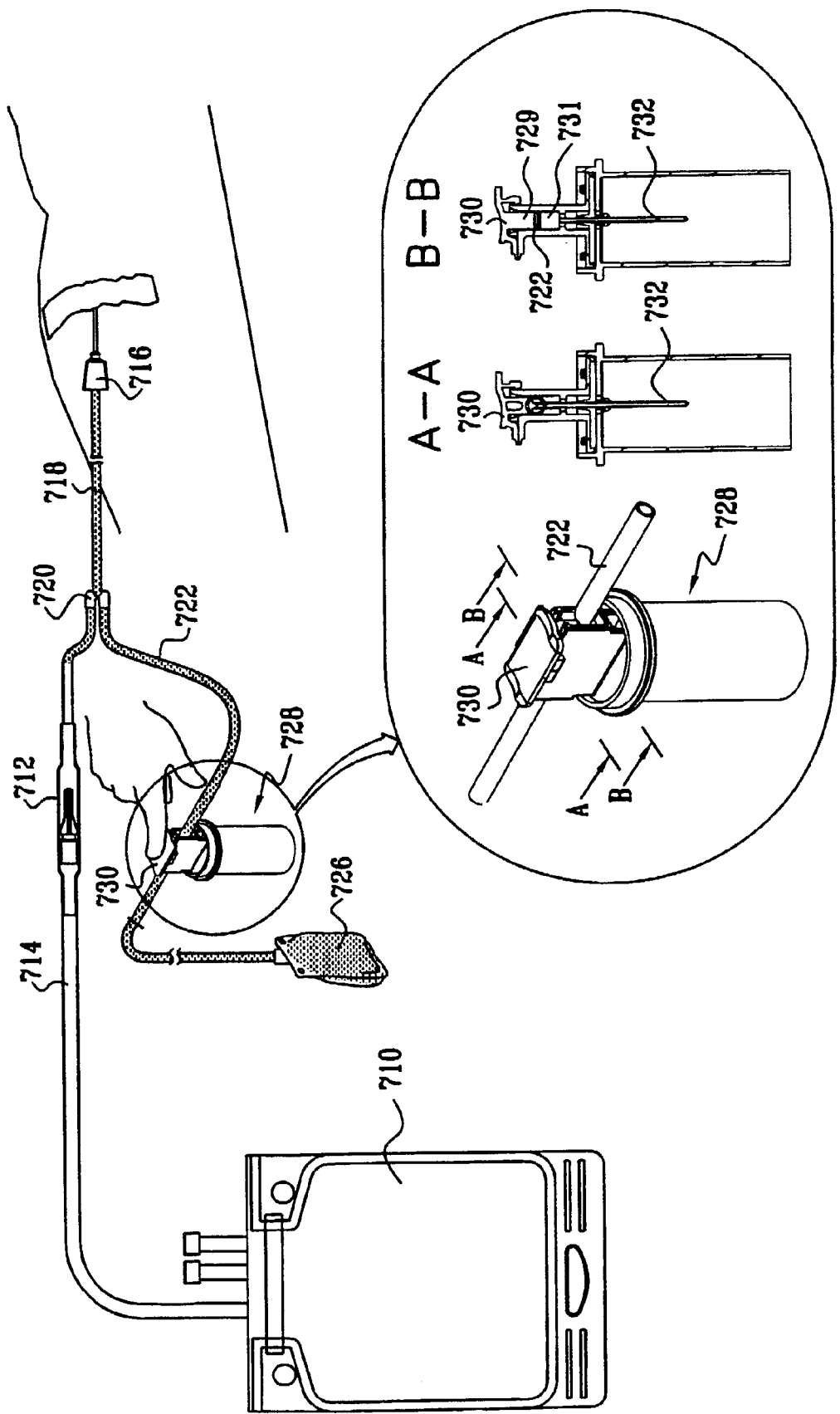

As seen in FIG. 19D, after the sampling bag 726 is filled, the clamping element 730 is closed, producing engagement between protrusions 729 and 731 for blocking further fluid communication between the sampling bag 726 and the sampling tube assembly 728 on the one hand and the remainder of the apparatus shown in FIG. 19D on the other hand. This engagement is shown particularly in section B—B of FIG. 19D.

FIG. 19D also shows operative engagement of the sampling tube assembly 728 to sampling conduit 722 downstream of protrusions 729 and 731 and upstream of sampling bag 726. Such engagement, by virtue of closing the clamping element 730, causes piercing of the sampling conduit 722 by a needle 732 in sampling tube assembly 728, thereby providing fluid communication with blood from sampling bag 726 and from conduit 722 downstream of protrusions 729 and 731. This piercing is shown particularly in section A—A of FIG. 19D.

Figure 19E:
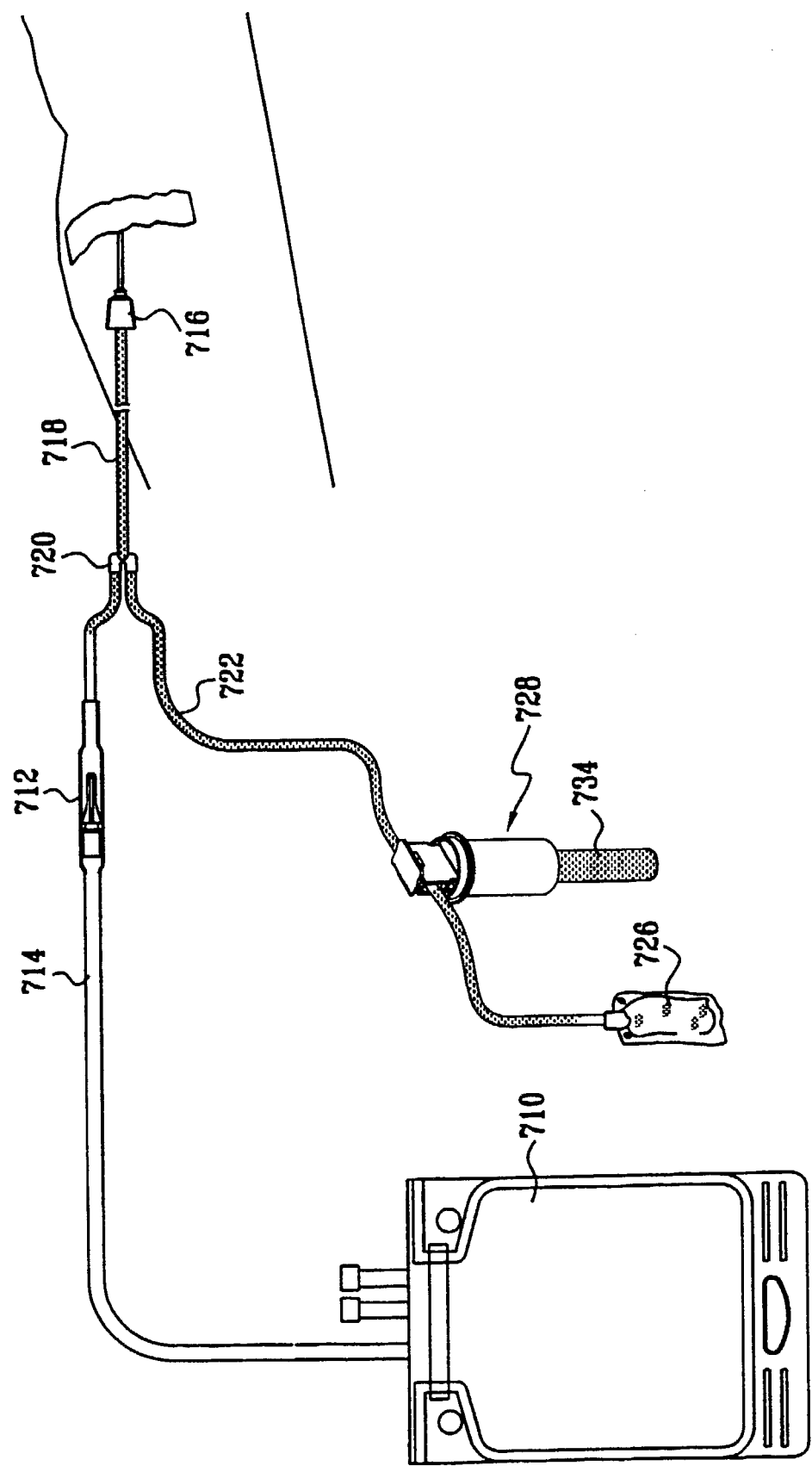

FIG. 19E shows operative engagement of a vacuum sampling tube 734 with sampling tube assembly 728. As a result of this engagement, needle 732 (FIG. 19D) communicates with the interior of the tube 734 and allows blood from sampling bag 726 and from conduit 722 downstream of protrusions 729 and 731 to fill the tube 734. This at least partially empties sampling bag 726.

Figure 19F:
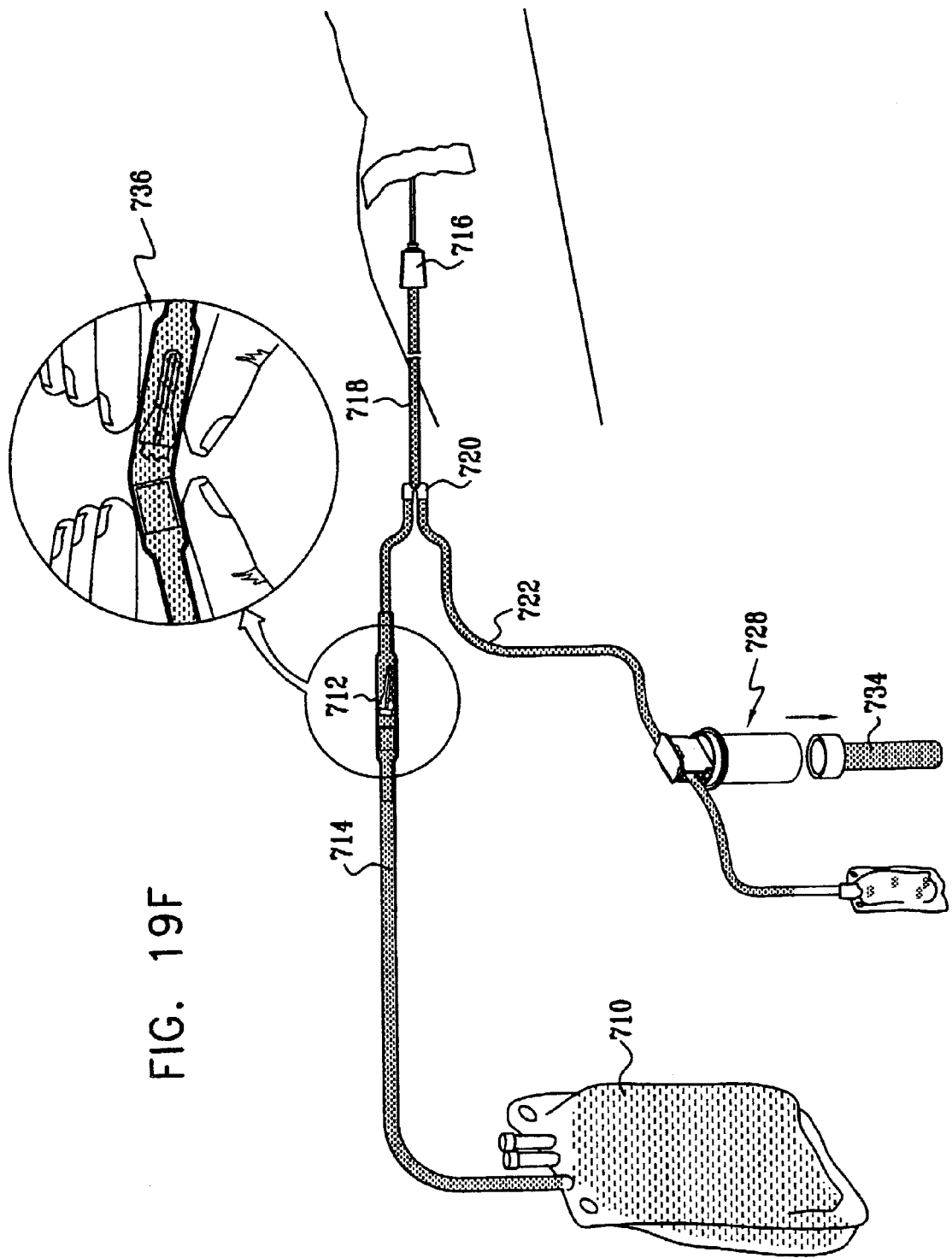

At this stage, as shown in FIG. 19F, sampling tube 734 may be disengaged from assembly 728 and breakaway cannula 712 may be broken as indicated at reference numeral 736 to allow blood flow from needle 716, via Y-connector 720, via broken breakaway cannula 712 and collection conduit 714 to fill collection bag 710.

Figure 20A:
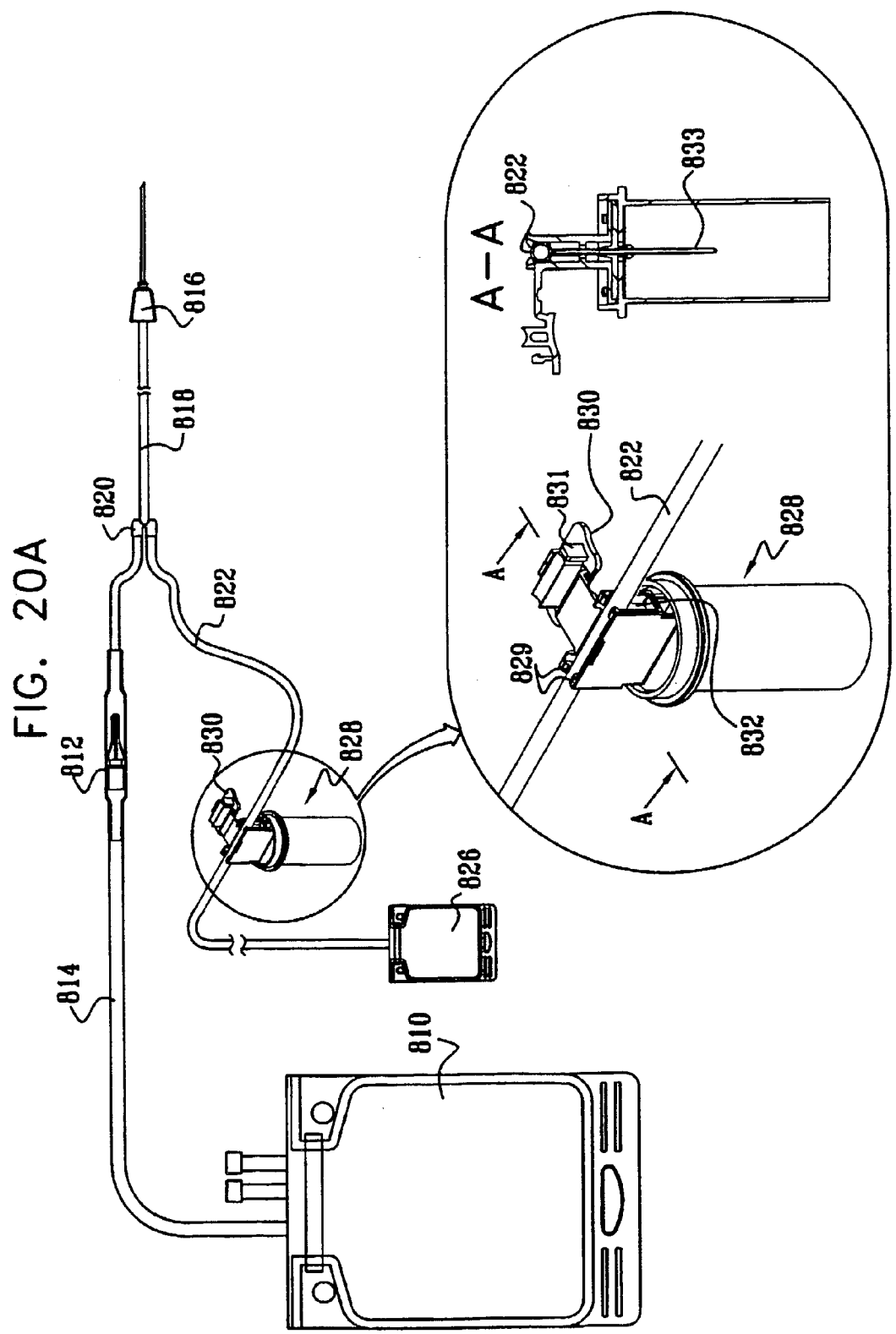

Reference is now made to FIGS. 20A, 20B, 20C, 20D and 20E, which are simplified illustrations of apparatus and a methodology for blood collection and sampling in accordance with still another preferred embodiment of the present invention. As seen in FIG. 20A, a collection bag 810, such as a conventional collection bag commercially available from Teva Medical Ltd. of Ashdod, Israel, is connected to a conventional breakaway cannula 812 via a collection conduit 814. A collection needle 816 is coupled to breakaway cannula 812 via a supply conduit 818 and via a Y-connector 820.

A sampling conduit 822 is also coupled to Y-connector 820 and extends to a sampling bag 826. FIG. 20A also shows pre-attachment of a sampling tube assembly 828 to sampling conduit 822 upstream of sampling bag 826. As noted above, the sampling tube assembly is preferably constructed and operative in accordance with teachings contained in applicant's Published PCT Patent Application WO 97/45714, the disclosure of which is hereby incorporated by reference.

It is a particular feature of the present invention that the sampling tube assembly 828 includes the following structure which is not described in the aforesaid Published PCT Patent Application WO 97/45714, namely:

a. the provision of a plurality of retaining protrusions 829, which serve to retain the sampling tube assembly 828 in engagement with the sampling conduit 822, even before closure of a clamping element 830 thereof; and b. the provision of a clamping protrusion 831 on clamping element 830 of sampling tube assembly 828 which cooperates with a clamping protrusion 832. The provision of clamping protrusions 831 and 832 obviates the need for a separate clamp, such as clamp 624 in the embodiment of FIGS. 18A–18F.

Breakaway cannula 812 is operative, when intact, to block fluid communication between Y-connector 820 and collection bag 810 and is operative, when broken, to allow blood from collection needle 816 to flow through collection conduit 814 to collection bag 810.

Figure 20B:
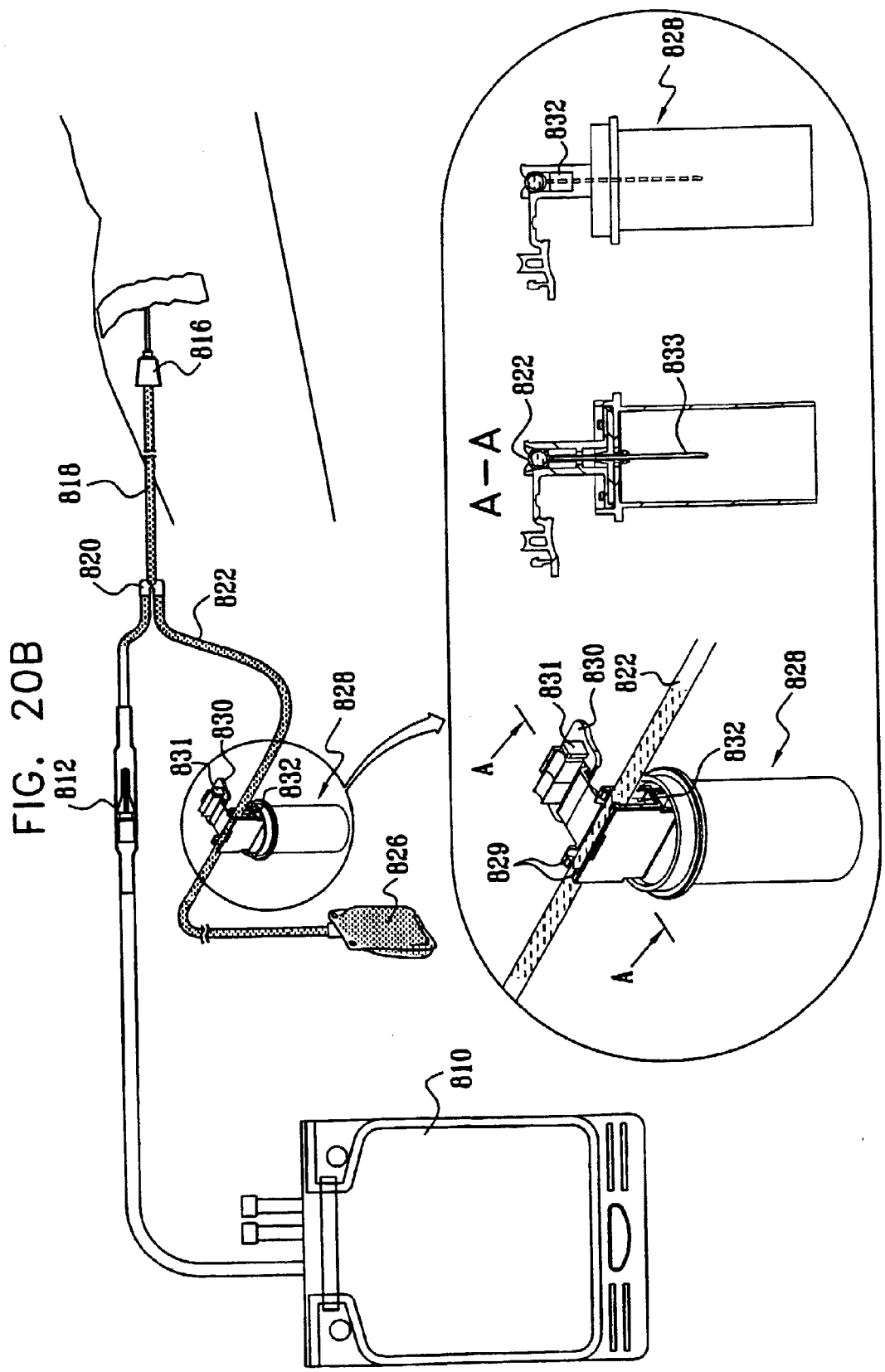

As seen in FIG. 20B, when the needle 816 is initially inserted into a donor's vein, while the breakaway cannula 812 is still intact and clamping element 830 has not yet been closed, the donor's blood fills the sampling bag 826.

As seen in FIG. 20C, after the sampling bag 826 is filled, the clamping element 830 is closed, thus blocking further fluid communication between the sampling bag 826 and the sampling tube assembly 828 on the one hand and the remainder of the apparatus shown in FIG. 20C on the other hand. This blocking, produced by mutual engagement of protrusions 831 and 832, is shown particularly in section B—B of FIG. 20C.

FIG. 20C also shows operative engagement of the sampling tube assembly 828 with sampling conduit 822 downstream of protrusions 831 and 832 and upstream of sampling bag 826. Such engagement, by virtue of closing the clamping element 830, causes piercing of the sampling conduit 822 by a needle 833 in sampling tube assembly 828, thereby providing fluid communication with blood from sampling bag 826 and from conduit 822 downstream of protrusions 831 and 832 and the interior of the needle 833. This piercing is shown particularly in section A—A of FIG. 20C.

In this connection, an additional feature of the sampling tube assembly 828, which is not described in the aforesaid Published PCT Patent Application WO 97/45714, is noted. A resilient material, such as a piece of foam rubber 834, is preferably provided around a sharp end of needle 833 forming part of sampling tube assembly 828 in order to prevent inadvertent and premature puncturing of sampling conduit 822 by needle 833. The provision of foam rubber 834 has another advantage, namely, providing a seal against leakage from sampling conduit 822, once it has been punctured by needle 833.

Figure 20D:
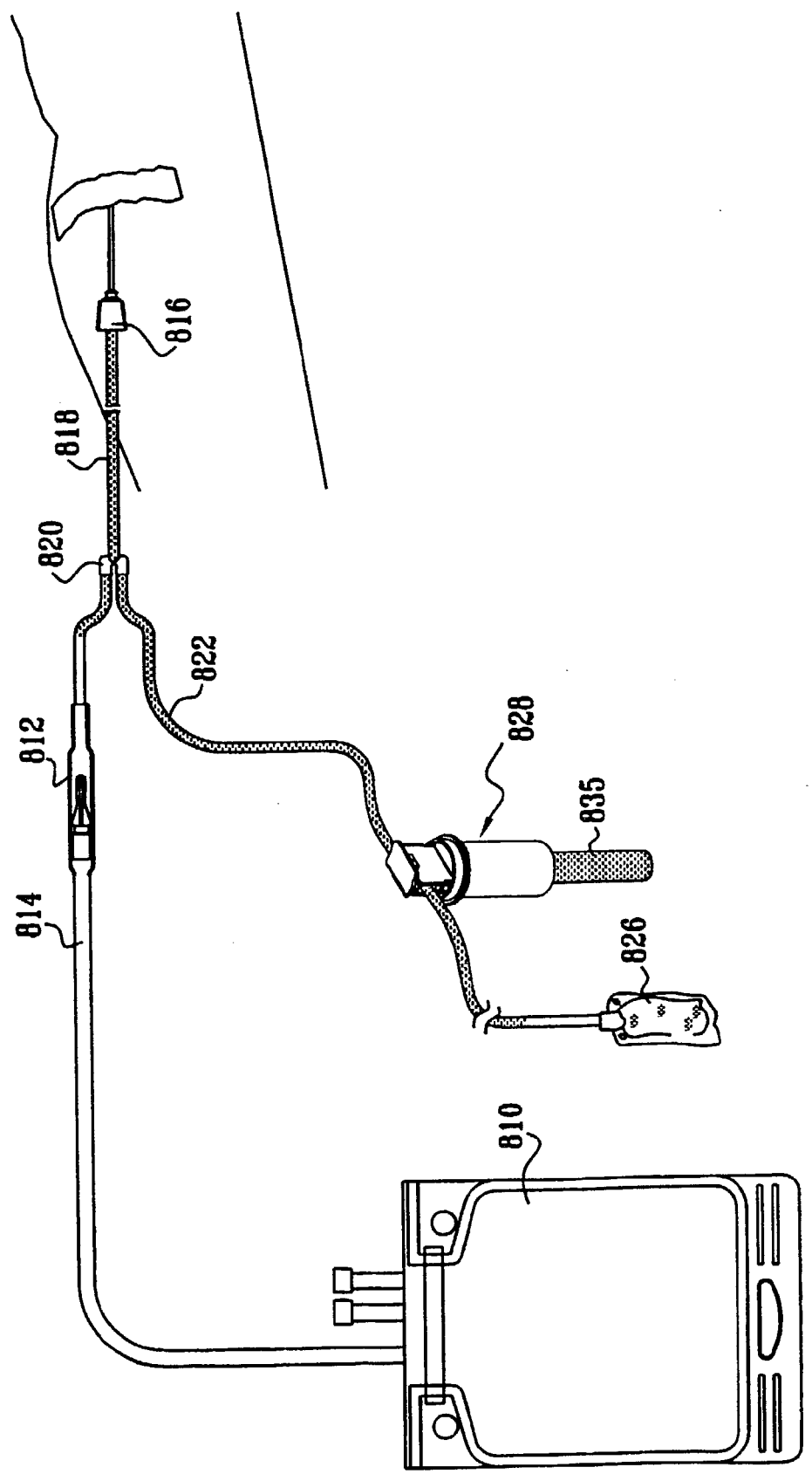

FIG. 20D shows operative engagement of a vacuum sampling tube 835 with sampling tube assembly 828. As a result of this engagement, needle 833 (FIG. 20C) communicates with the interior of the tube 835 and allows blood from sampling bag 826 and from conduit 822 downstream of protrusions 831 and 832 to fill the tube 835. This at least partially empties sampling bag 826.

Figure 20E:
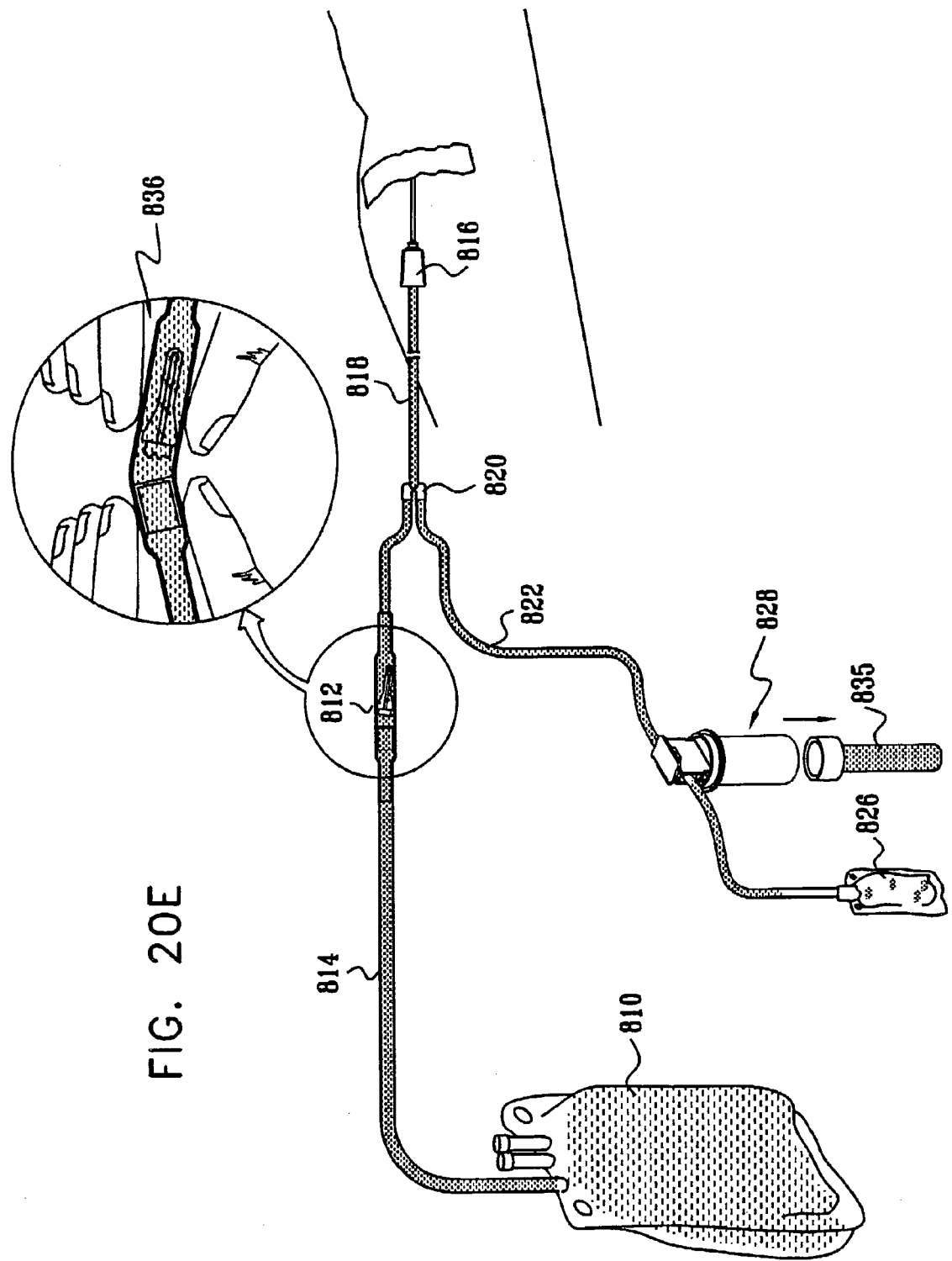

At this stage, as shown in FIG. 20E, sampling tube 835 may be disengaged from assembly 828 and breakaway cannula 812 may be broken as indicated at reference numeral 836 to allow blood flow from needle 816, via Y-connector 820, via broken breakaway cannula 812 and collection conduit 814 to fill collection bag 810.

Figure 21A:
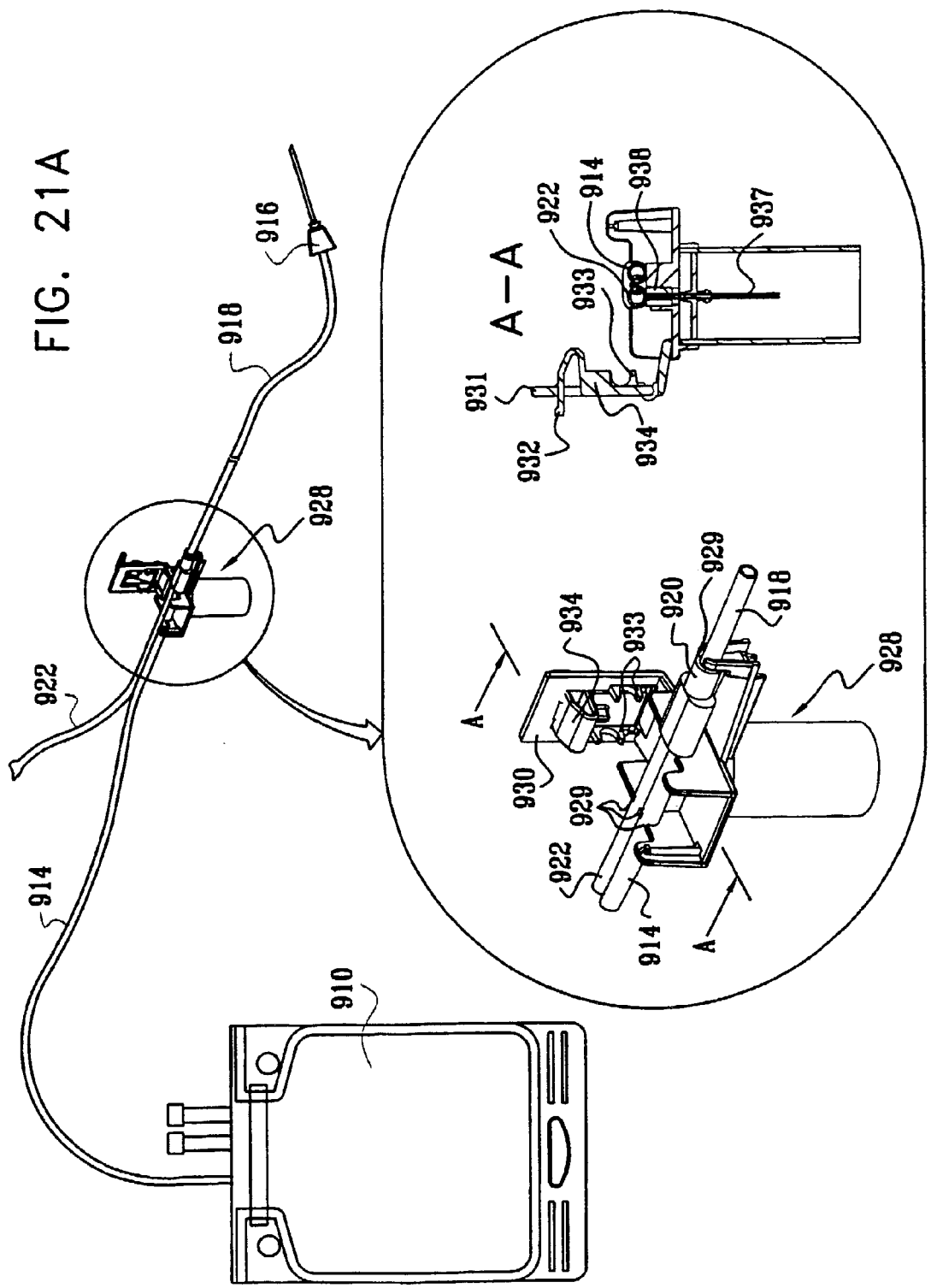

Reference is now made to FIGS. 21A, 21B, 21C, 21D, 21E and 21F, which are simplified illustrations of apparatus and a methodology for blood collection and sampling in accordance with still another preferred embodiment of the present invention. As seen in FIG. 21A, a collection bag 910, such as a conventional collection bag commercially available from Teva Medical Ltd. of Ashdod, Israel, is connected to a collection conduit 914. A collection needle 916 is coupled via a supply conduit 918 to a Y-connector 920, along with collection conduit 914. A sampling conduit 922 is also coupled to Y-connector 920.

FIG. 21A also shows pre-attachment of a sampling tube assembly 928 to sampling conduit 922. As noted above, the sampling tube assembly is preferably constructed and operative in accordance with teachings contained in applicant's Published PCT Patent Application WO 97/45714, the disclosure of which is hereby incorporated by reference.

It is a particular feature of the present invention that the sampling tube assembly 928 includes the following structure which is not described in the aforesaid Published PCT Patent Application WO 97/45714, namely:

a. the provision of a plurality of retaining protrusions 929, which serve to retain the sampling tube assembly 928 in engagement with the collection conduit 914 and with the sampling conduit 922, even before closure of a clamping assembly 930 of sampling tube assembly 928;

b. the provision of clamping assembly 930 which operatively engages both the sampling conduit 922 and the collection conduit 914;

c. the provision in clamping assembly 930 to have first and second separately hinged clamping elements, respectively designated 931 and 932. Clamping element 931 includes engagement protrusions 933 which, when closed, engage sampling conduit 922 and produce piercing thereof as described hereinbelow. Clamping element 932 includes a protrusion 934 which, when closed, produces blocking of the collection conduit 914. The provision of protrusion 934 obviates the need for a breakaway cannula in series with collection conduit 914, as in the embodiment of FIGS. 18A–18F.

Thus it may be appreciated that protrusion 934 is operative, when clamping element 932 is closed, to block fluid communication between Y-connector 920 and collection bag 910 and is operative, when clamping element 932 is open, to allow blood from collection needle 916 to flow through collection conduit 914 to collection bag 910.

As seen in FIG. 21B, prior to insertion of needle 916 into a donor's vein, both clamping elements 931 and 932 of clamping assembly 930 are closed and locked in a closed position. As shown particularly in FIG. 21B, locking of clamping element 931 in a closed position, may be provided by locking protrusions 935. As seen particularly in section A—A of FIG. 21B, locking of clamping element 932 in a closed position onto clamping element 931, may be provided by a locking protrusion 936 formed on clamping element 932.

It is noted that closure and locking of clamping element 932 automatically produces closure and locking of clamping element 931. Preferably, prior to use, clamping elements 931 and 932 are provided in locked together mutual engagement.

Operative engagement of engagement protrusions 933 of the sampling tube assembly 928 with sampling conduit 922 causes piercing of the sampling conduit 922 by a needle 937 in sampling tube assembly 928. This piercing is shown particularly in section A—A of FIG. 21B.

In this connection, an additional feature of the sampling tube assembly 928, which is not described in the aforesaid Published PCT Patent Application WO 97/45714, is noted. A resilient material, such as a piece of foam rubber 938, is preferably provided around a sharp end of needle 937 forming part of sampling tube assembly 928 in order to prevent inadvertent and premature puncturing of sampling conduit 922 by needle 937. The provision of foam rubber 938 has another advantage, namely, providing a seal against leakage from sampling conduit 922, once it has been punctured by needle 937.

Thus, prior to insertion of needle 916 into a donor's vein, sampling conduit 922 is pierced and collection conduit 914 is blocked, as shown particularly in section A—A of FIG. 21B.

Figure 21C:
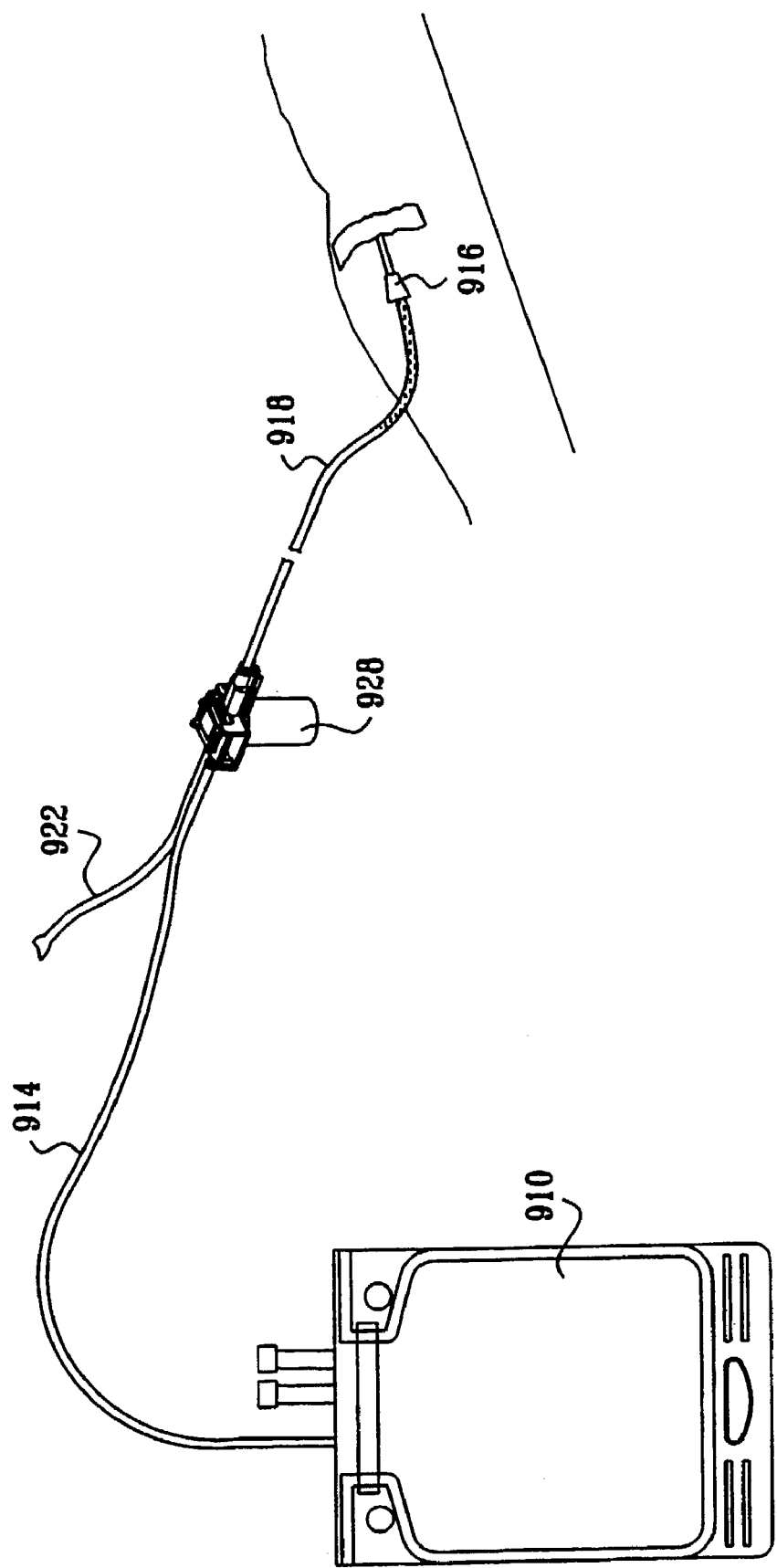

With the sampling tube assembly 928 in the operative orientation described hereinabove with respect to FIG. 21B, the needle 916 is inserted into the donor's vein and the donor's blood partly fills the supply conduit 918, as shown in FIG. 21C.

As seen in FIG. 21D, after insertion of the needle 916 into the donor's vein when the sampling tube assembly 928 is in the operative orientation described hereinabove with reference to FIG. 21B, a vacuum sampling tube 939 is brought into operative engagement with sampling tube assembly 928. As a result of this engagement, needle 937 (FIG. 21B) communicates with the interior of the tube 939 and allows blood from supply conduit 918 to fill the tube 939.

Figure 21F:
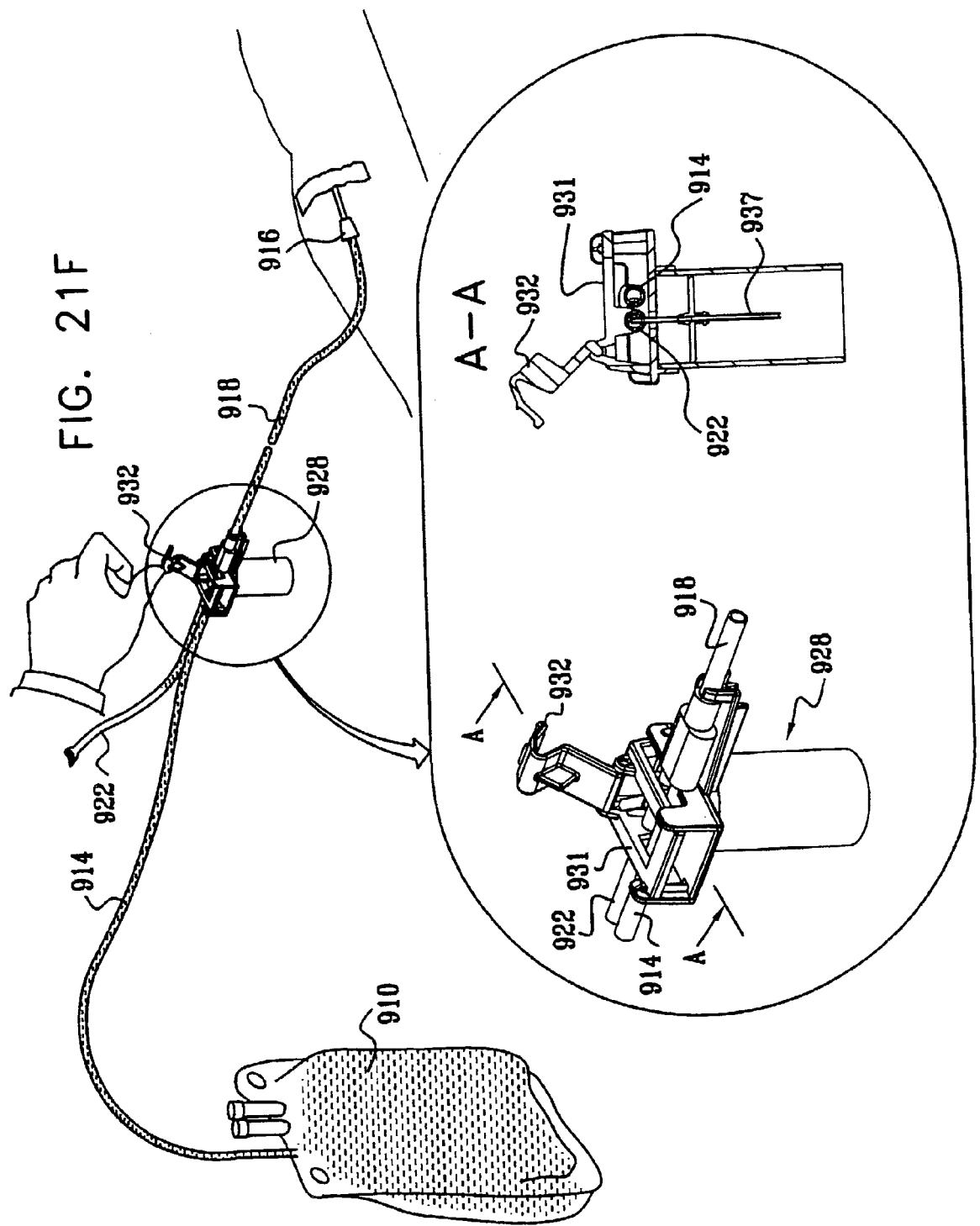

At this stage, as shown in FIG. 21E, sampling tube 939 may be disengaged from assembly 928. Thereafter, as shown in FIG. 21F, clamping element 932 may be unlocked from clamping element 931 and opened, thus enabling blood to flow from needle 916 via supply conduit 918 and collection conduit 914 to the collection bag 910. The clamping element 931 preferably remains in operative engagement with sampling conduit 922 such that needle 937 remains in operative engagement therewith, thus preventing leakage of blood therefrom.

Figure 22B:
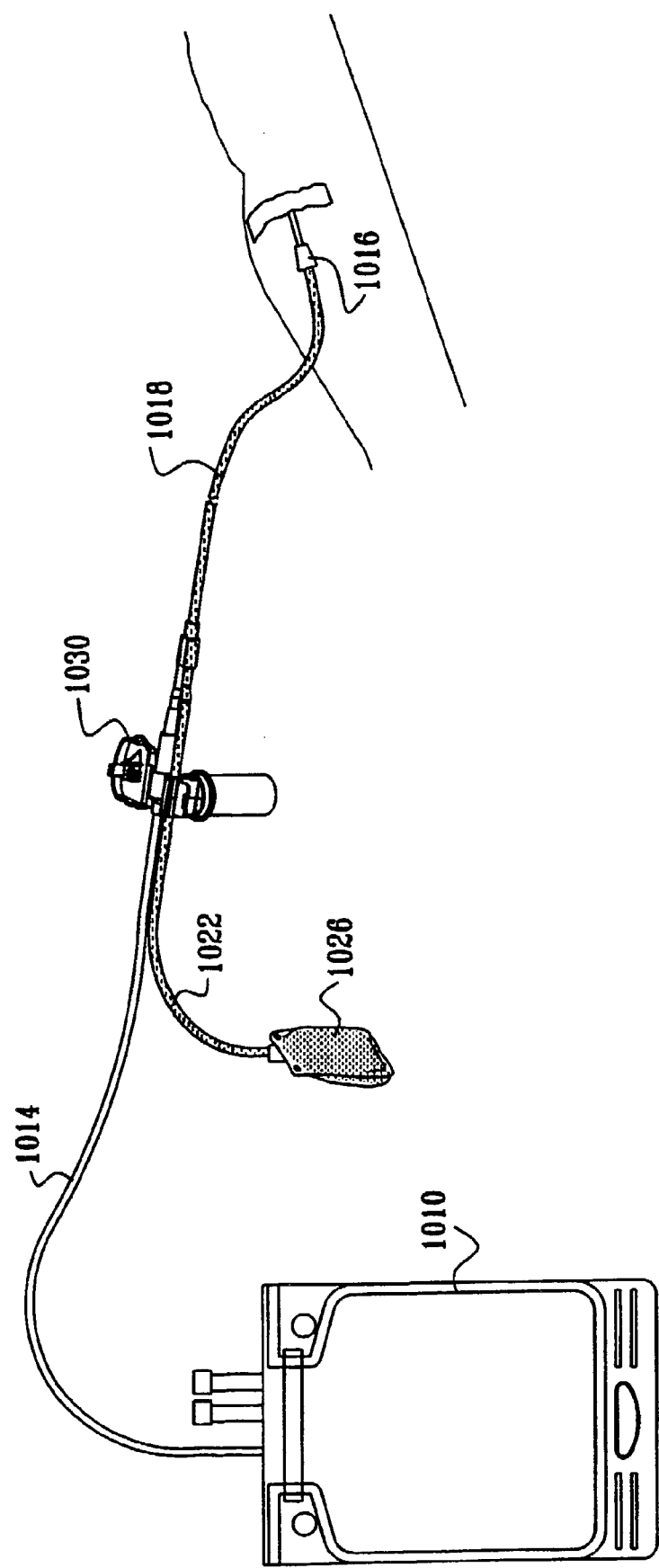

Reference is now made to FIGS. 22A, 22B, 22C, 22D and 22E, which are simplified illustrations of apparatus and a methodology for blood collection and sampling in accordance with still another preferred embodiment of the present invention. As seen in FIG. 22A, a collection bag 1010, such as a conventional collection bag commercially available from Teva Medical Ltd. of Ashdod, Israel, is connected to a collection conduit 1014. A collection needle 1016 is coupled via a supply conduit 1018 to a Y-connector 1020. A sampling conduit 1022 is also coupled to Y-connector 1020. Collection conduit 1014 is connected via a breakaway cannula 1024 with Y-connector 1020. A sampling bag 1026 is also connected to sampling conduit 1022.

FIG. 22A also shows pre-attachment of a sampling tube assembly 1028 to sampling conduit 1022 and to breakaway cannula 1024. As noted above, the sampling tube assembly 1028 is preferably constructed and operative in accordance with teachings contained in applicant's Published PCT Patent Application WO 97/45714, the disclosure of which is hereby incorporated by reference.

It is a particular feature of the present invention that the sampling tube assembly 1028 includes the following structure which is not described in the aforesaid Published PCT Patent Application WO 97/45714. namely:

a. the provision of a plurality of retaining protrusions 1029, which serve to retain the sampling tube assembly 1028 in engagement with the sampling conduit 1022, even before closure of a clamping assembly 1030 of sampling tube assembly 1028;

b. the provision of a receiving bore or recess 1031 in sampling tube assembly 1028 for receiving and retaining therewithin breakaway cannula 1024. The breakaway cannula 1024 may be retained within receiving bore or recess 1031 by the use of adhesive or otherwise;

c. the provision of clamping assembly 1030 which operatively engages both the sampling conduit 1022 and the breakaway cannula 1024;

d. the provision in clamping assembly 1030 to have first and second and third functionalities as follows:

1. breaking of the breakaway cannula 1024 to enable blood flow therethrough from the supply conduit 1018 to the collection conduit 1014, by engagement of a protruding breaking tooth 1032 formed on clamping assembly 1030 with a portion 1033 of the breakaway cannula 1024 which extends typically upstream of the bore or recess 1031 in the sampling tube assembly 1028;

2. blocking of the sampling conduit 1022 upstream of a piercing needle 1034 of the sampling tube assembly 1028, by a protrusion 1035 in cooperation with a protrusion 1036 formed in the sampling tube assembly 1028; and 3. pressing of the sampling conduit 1022 by means of engagement protrusions 1037 which engage sampling conduit 1022 and produce piercing thereof as described hereinbelow.

As seen in FIG. 22B, needle 1016 is inserted into a donor's vein prior to closing clamping assembly 1030. The donor's blood fills the sampling bag 1026, as well as the sampling conduit 1022 and the supply conduit 1018.

As shown in FIG. 22C, when the sampling bag 1026 is filled, the clamping assembly 1030 is closed and locked in a closed position. As shown particularly in FIG. 22A and also in FIG. 22C, locking of clamping assembly 1030 in a closed position, may be provided by a locking tooth 1038 which engages a cooperating socket 1039.

As noted hereinabove, closing and locking of clamping assembly 1030 simultaneously provides the following, three functionalities:

1. breaking of the breakaway cannula 1024 to enable blood flow therethrough from the supply conduit 1018 to the collection conduit 1014, by engagement of the protruding breaking tooth 1002 formed on clamping assembly 1030 with portion 1033 of the breakaway cannula 1024 which extends typically upstream of the bore or recess 1031 in the sampling tube assembly 1028. This breaking allows blood to flow from the needle 1016, via the supply conduit 1018, the Y-connection 1020, the broken breakaway cannula 1024 and collection conduit 1014 to the collection bag 1010.

2. blocking of the sampling conduit 1022 upstream of piercing needle 1034 of the sampling tube assembly 1028, by the protrusion 1035 in cooperation with the protrusion 1036 formed in the sampling tube assembly 1028. This blocking isolates the sampling bag 1026 and the sampling tube assembly 1028 on the one hand from the remainder of the apparatus of FIG. 22C on the other hand.

3. pressing of the sampling conduit 1022 by means of engagement protrusions 1037 which engage sampling conduit 1022 and produce piercing thereof as described hereinbelow. This piercing is produced by needle 1034 which is located in sampling tube assembly 1028. This piercing is shown particularly in section B—B of FIG. 22C.

In this connection, an additional feature of the sampling tube assembly 1028, which is not described in the aforesaid Published PCT Patent Application WO 97/45714, is noted. A resilient material, such as a piece of foam rubber 1040, is preferably provided around a sharp end of needle 1034 forming part of sampling tube assembly 1028 in order to prevent inadvertent and premature puncturing of sampling conduit 1022 by needle 1034. The provision of foam rubber 1040 has another advantage, namely, providing a seal against leakage from sampling conduit 1022, once it has been punctured by needle 1034.

Thus, following insertion of needle 1016 into a donor's vein and filling of the sampling bag 1026, sampling conduit 1022 is pierced and collection conduit 1014 is unblocked by breakage of the breakaway cannula 1024, as shown particularly in section A—A of FIG. 22C.

Figure 22D:
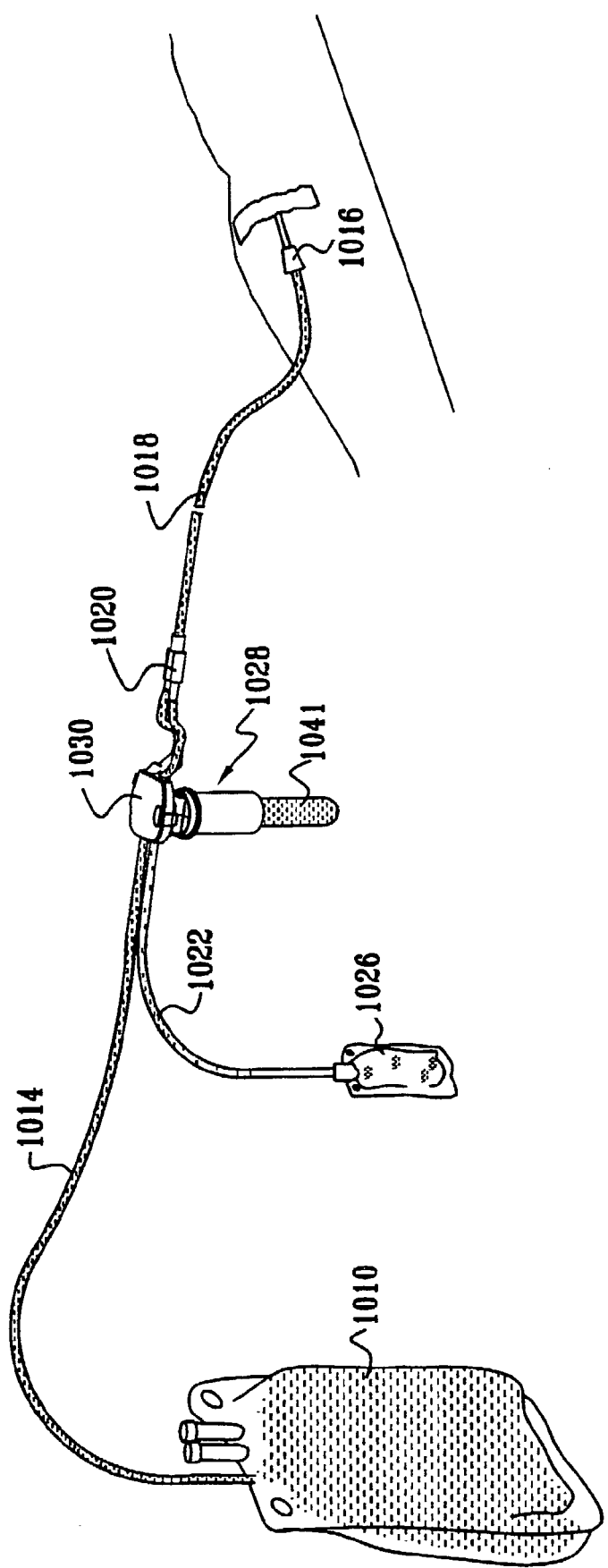

As seen in FIG. 22D, after carrying out of the three functionalities described hereinabove, a vacuum sampling tube 1041 is brought into operative engagement with sampling tube assembly 1028. As a result of this engagement, needle 1034 (FIG. 22C) communicates with the interior of the tube 1041 and allows blood from sampling bag 1026 to fill the tube 1041.

At this stage, as shown in FIG. 22E, sampling tube 1041 may be disengaged from assembly 1028.

Figure 23B:
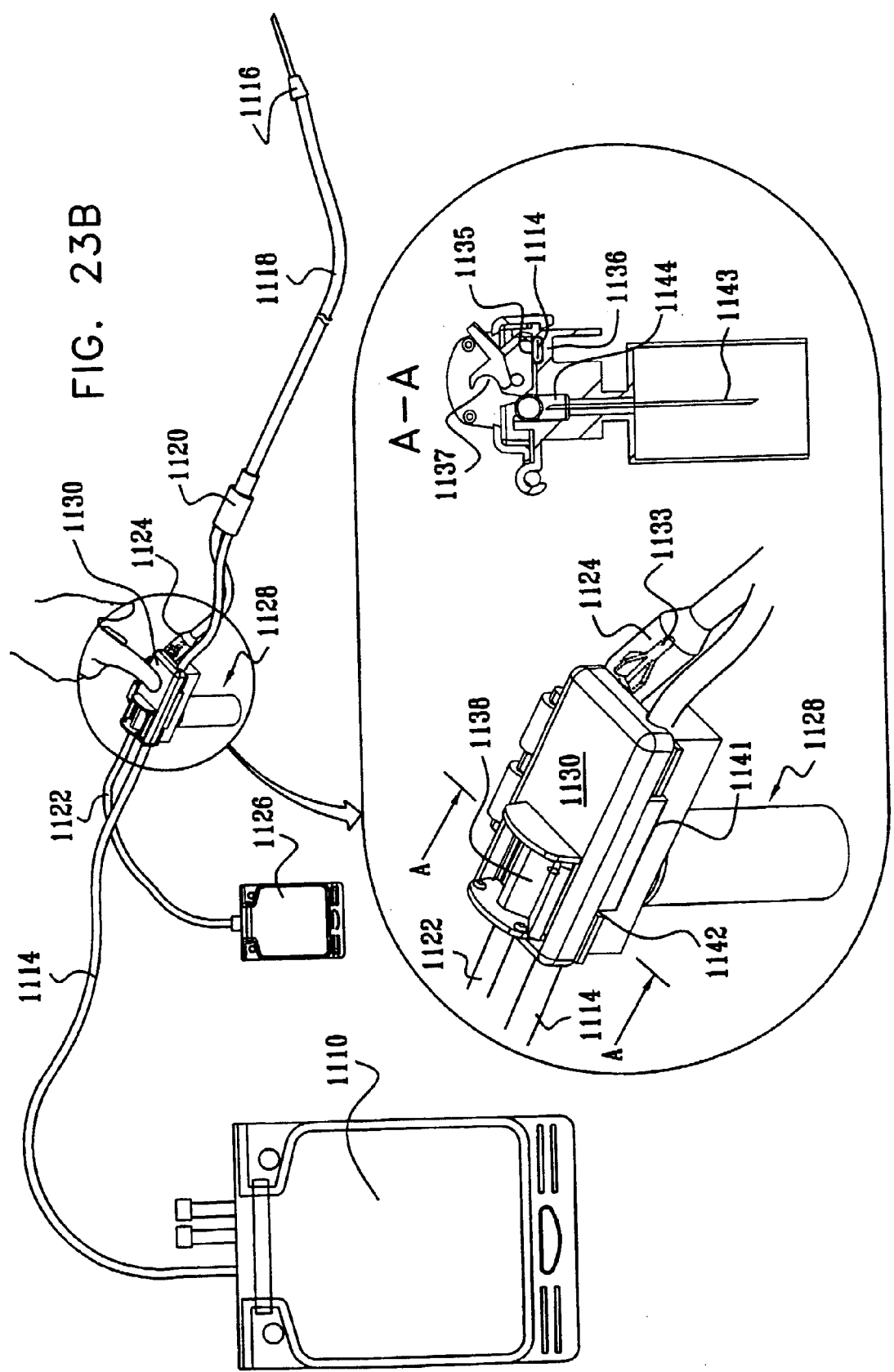

Reference is now made to FIGS. 23A, 23B, 23C, 23D, 23E and 23F, which are simplified illustrations of apparatus and a methodology for blood collection and sampling in accordance with still another preferred embodiment of the present invention. As seen in FIG. 23A, a collection bag 1110, such as a conventional collection bag commercially available from Teva Medical Ltd. of Ashdod, Israel, is connected to a collection conduit 1114. A collection needle 1116 is coupled via a supply conduit 1118 to a Y-connector 1120. A sampling conduit 1122 is coupled via a breakaway cannula 1124 to Y-connector 1120. Collection conduit 1114 is also connected with Y-connector 1120. A sampling bag 1126 is also connected to sampling conduit 1122.

FIG. 23A also shows pre-attachment of a sampling tube assembly 1128 to collection conduit 1114 and to breakaway cannula 1124. As noted above, the sampling tube assembly 1128 is preferably constructed and operative in accordance with teachings contained in applicant's Published PCT Patent Application WO 97/45714, the disclosure of which is hereby incorporated by reference.

Figure 23D:
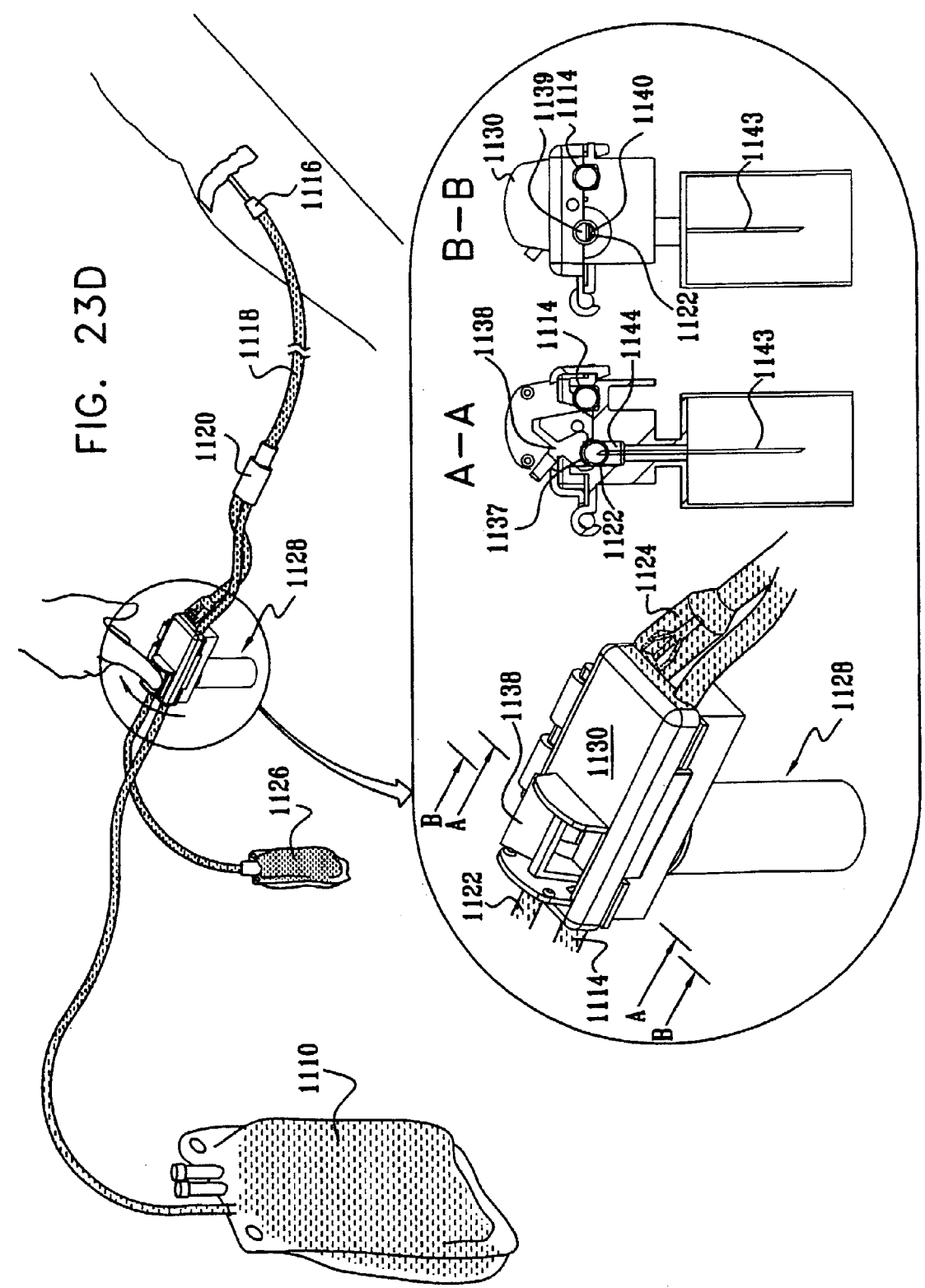

It is a particular feature of the present invention that the sampling tube assembly 1128 includes the following structure which is not described in the aforesaid Published PCT Patent Application WO 97/45714, namely:

a. the provision of a plurality of retaining protrusions 1129, which serve to retain the sampling tube assembly 1128 in engagement with the collection conduit 1114, even before closure of a clamping assembly 1130 of sampling tube assembly 1128;

b. the provision of a receiving bore or recess 1131 in sampling tube assembly 1128 for receiving and retaining therewithin breakaway cannula 1124. The breakaway cannula 1124 may be retained within receiving bore or recess 1131 by the use of adhesive or otherwise:

c. the provision of clamping assembly 1130 which operatively engages both the collection conduit 1114 and the breakaway cannula 1124;

d. the provision in clamping assembly 1130 to have first and second and third functionalities as follows:

1. breaking of the breakaway cannula 1124 to enable blood flow therethrough from the supply conduit 1118 to the sampling conduit 1122 and thence to sampling bag 1126, by engagement of an edge 1132 formed on clamping assembly 1130 with a portion 1133 of the breakaway cannula 1124 which extends typically upstream of the bore or recess 1131 in the sampling tube assembly 1128;

2. piercing of the sampling conduit 1122 by means of engagement protrusions 1137 which engage sampling conduit 1122 and produce piercing thereof as described hereinbelow, by employing a clamping element 1138 which is hinged to the remainder of clamping assembly 1130 and which is formed on the underside thereof with engagement protrusions 1139 and 1140 (as shown in FIG. 23D). The clamping element 1138 is moved, as described hereinbelow, from a first locking position as shown in FIG. 23A to a second locking position shown in FIG. 23D; and 3. blocking of the collection conduit 1114, by a protrusion 1135 in cooperation with a protrusion 1136 formed in the sampling tube assembly 1128, as shown in FIG. 23B. As shown in FIG. 23A, the protrusion 1135 is located on the lower portion of the clamping element 1138.

As seen in FIG. 23B, prior to insertion of needle 1116 into a donor's vein, the clamping assembly 1130 is closed and locked in a closed position. As shown particularly in FIG. 23A and also in FIG. 23C, locking of clamping assembly 1130 in a closed position, may be provided by a locking tooth 1141 which engages a cooperating socket 1142.

As noted hereinabove, closing and locking of clamping assembly 1130 simultaneously provides the following two functionalities:

1. breaking of the breakaway cannula 1124 to enable blood flow therethrough from the supply conduit 1118 to the sampling conduit 1122, by engagement of protruding breaking edge 1132 formed on clamping assembly 1130 with portion 1133 of the breakaway cannula 1124 which extends upstream of the bore or recess 1131 in the sampling tube assembly 1128. This breaking allows blood to flow from the needle 1116, via the supply conduit 1118, the Y-connection 1120, the broken breakaway cannula 1124 and sampling conduit 1122 to the sample bag 1126.

2. blocking of the collection conduit 1114, by protrusion 1135 in cooperation with a protrusion 1136 formed in the sampling tube assembly 1128. This blocking isolates the collection bag 1110 from the remainder of the apparatus of FIG. 23C.

As seen in FIG. 23C, following closing and locking of the clamping assembly 1130 and generally simultaneous operation of the two functionalities described hereinabove, the needle 1116 is inserted into a vein of a donor, thus filling the sampling bag 1126.

Referring now to FIG. 23D, it is seen that following filling of the sampling bag 1126, the clamping element 1138 is moved from the first locking position (FIG. 23A) to the second locking position, with respect to the remainder of clamping assembly 1130, causing engagement of protrusions 1139 and 1140 with the sampling conduit 1122 and causing piercing and blocking thereof. Closing and locking clamping element 1138 also simultaneously causes unblocking of collection conduit 1114 by virtue of repositioning of protrusions 1135 and 1136.

The piercing is produced by a needle 1143 in sampling tube assembly 1128. This piercing is shown particularly in section A—A of FIG. 23C.

In this connection, an additional feature of the sampling tube assembly 1128, which is not described in the aforesaid Published PCT Patent Application WO 97/45714, is noted. A resilient material, such as a piece of foam rubber 1144, is preferably provided around a sharp end of needle 1143 forming part of sampling tube assembly 1128 in order to prevent inadvertent and premature puncturing of sampling conduit 1122 by needle 1143. The provision of foam rubber 1144 has another advantage, namely, providing a seal against leakage from sampling conduit 1122, once it has been punctured by needle 1143.

Blocking of sampling conduit 1122 isolates the sample bag 1126 and the sampling tube assembly 1128 from the remainder of the system shown in FIG. 23D. The unblocking of collection conduit 1114 and the blocking of sampling conduit 1122 by moving the clamping element 1138 from the first locking position (FIG. 23A) to the second locking position, is shown particularly at section B—B in FIG. 23D.

Figure 23E:
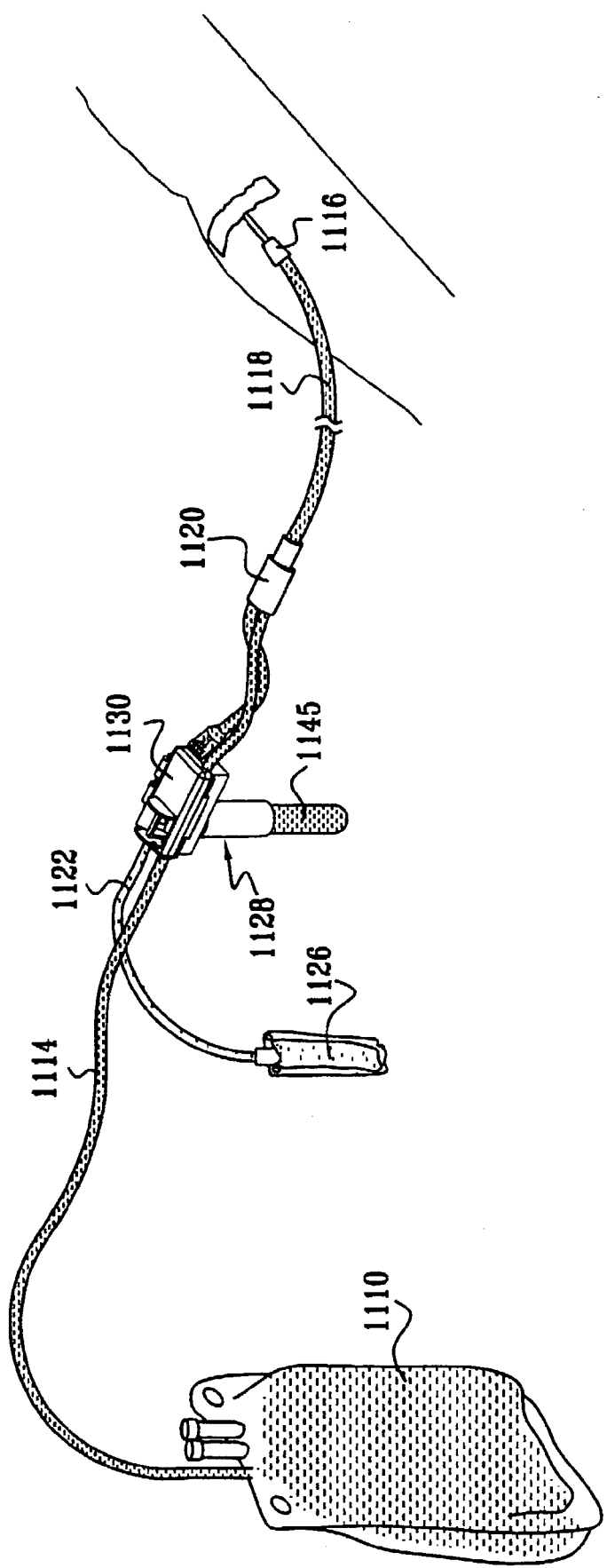

As seen in FIG. 23E, after carrying out of the three functionalities described hereinabove, a vacuum sampling tube 1145 is brought into operative engagement with sampling tube assembly 1128. As a result of this engagement, needle 1143 (FIG. 23B) communicates with the interior of the tube 1145 and allows blood from sampling bag 1126 to fill the tube 1145.

Figure 23F:
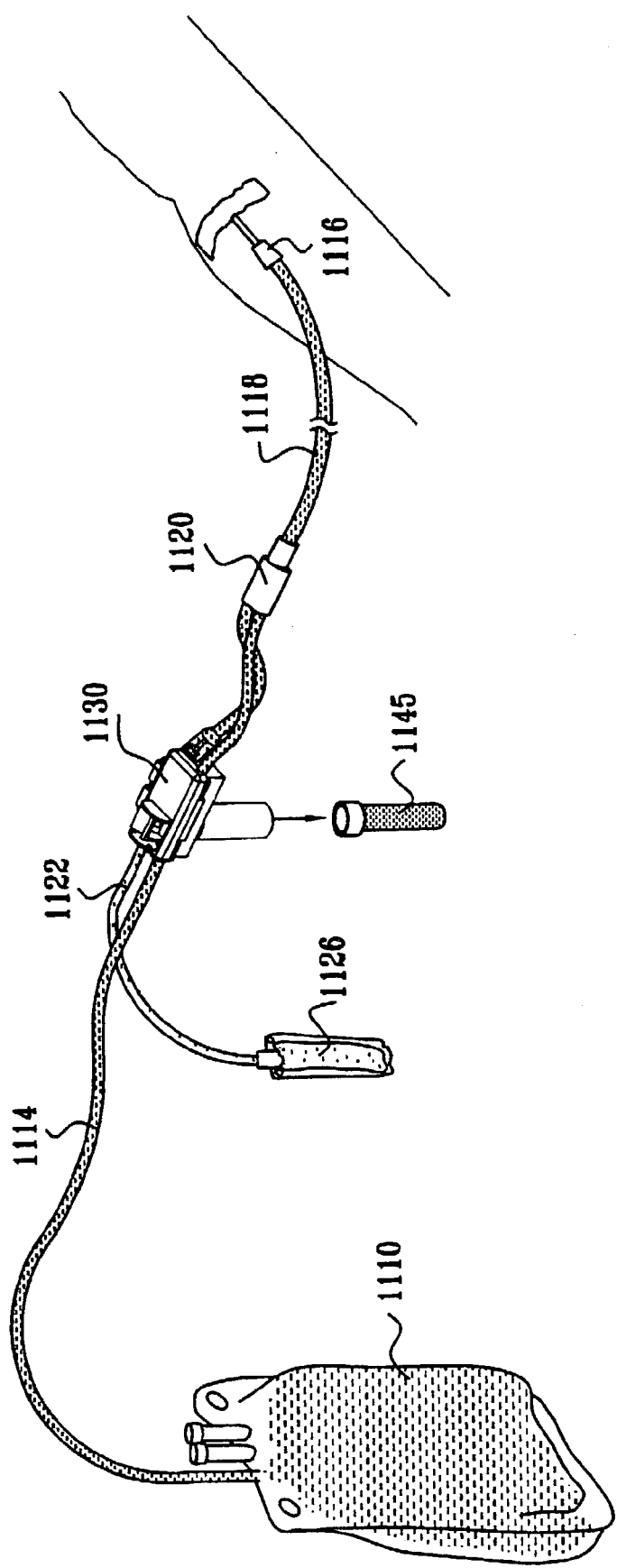

At this stage, as shown in FIG. 23F, sampling tube 1145 may be disengaged from assembly 1128.

It will be appreciated by persons skilled in the art that the present invention is not limited by what has been particularly shown and described hereinabove. Rather the scope of the present invention includes both combinations and subcombinations of the various features described hereinabove as well as variations and improvements therein as would occur to a person skilled in the art upon reading the foregoing description and which are not in the prior art.

What is claimed is:

1. A donor blood donation and sampling system comprising:
   a donor needle adapted for drawing blood from a body;
   a blood collection bag coupled to a blood collection conduit which is coupled to said donor needle;
   a blood sampling conduit also coupled to said donor needle;
   a sampling tube assembly including:
      a housing element; and
      a clamping assembly disposed within said housing element and arranged for selectable fluid engagement with said blood sampling conduit and for selectable clamping engagement with at least said blood collection conduit, thereby selectably stopping blood flow in at least said blood collection conduit; and
   a blood supply conduit coupled to said donor needle, said blood collection conduit and said blood sampling conduit each being coupled to said blood supply conduit.

2. A donor blood donation and sampling system according to claim 1 and also comprising a breakaway cannula located on said blood collection conduit.

3. A donor blood donation and sampling system according to claim 2 and wherein said sampling tube assembly also comprises:
   a needle having first and second sharpened points at its opposite ends;
   a vacuum sampling tube receiving socket for removably receiving a vacuum sampling tube in fluid engagement with said needle at said second sharpened point, thereby providing fluid communication between blood in said blood sampling conduit and the interior of said vacuum sampling tube; and
   resilient material disposed about said first sharpened point for preventing inadvertent piercing of said blood sampling conduit by said needle prior to clamping engagement therebetween,
   wherein said clamping assembly is arranged for selectable clamping engagement of said blood sampling conduit in fluid engagement with said needle, said clamping engagement causing piercing of said blood sampling conduit by said first sharpened point of said needle and wherein said resilient material comprises a sealing material operative in association with said blood sampling conduit and said needle for preventing leakage of blood from said blood sampling conduit after piercing thereof by said needle.

4. A donor blood donation and sampling system according to claim 3 and wherein said resilient material comprises a foam material.

5. A donor blood donation and sampling system according to claim 3 and wherein said sampling tube assembly is operative upon selectable clamping engagement with said blood sampling conduit and a blood collection conduit to simultaneously pierce said blood sampling conduit and block said blood collection conduit.

6. A donor blood donation and sampling system according to claim 3 and wherein said clamping assembly is also operative upon selectable clamping engagement with said blood sampling conduit to break said breakaway cannula, thereby permitting blood flow therethrough.

7. A donor blood donation and sampling system according to claim 3 and wherein said clamping assembly is operative to have the following functionalities:
   a. breaking of said breakaway cannula to enable blood flow therethrough from said blood supply conduit to said blood collection conduit;
   b. blocking of said blood sampling conduit upstream of said needle of said sampling tube assembly; and
   c. piercing of said blood sampling conduit.

8. A donor blood donation and sampling system according to claim 1 wherein blood sampling conduit includes a breakaway cannula, and wherein said sampling tube assembly comprises a clamping assembly which operatively engages both the sampling conduit and the collection conduit, said clamping assembly having first and second separately hinged clamping elements, said first clamping element including engagement protrusions which, when closed, engage said sampling conduit and produce piercing thereof, said second clamping element including a protrusion which, when said clamping element is closed, produces blocking of said collection conduit.

9. A donor blood donation and sampling system according to claim 8 wherein closure and locking of said first clamping element automatically produces closure and locking of said second clamping element and wherein said second clamping element may be unlocked from said first clamping element and opened, thus enabling blood to flow from said needle via said collection conduit to said collection bag.

10. A donor blood donation and sampling system according to claim 8 and wherein said clamping assembly is operative to have the following functionalities:
    a. breaking of said breakaway cannula to enable blood flow therethrough from said supply conduit to said sampling conduit; and
    b. blocking of said collection conduit.

11. A donor blood donation and sampling system according to claim 1 and wherein said sampling tube assembly is arranged to receive pre-donation blood directly from said donor needle via said blood sampling conduit.

12. A donor blood donation and sampling system according to claim 1 and also comprising an expansion container connected to at least one of said blood sampling conduit and said supply conduit leading to said blood sampling conduit and said blood collection conduit, said expansion container being operative to enable an initial blood flow from said needle at least toward said expansion container, thereby enabling an operator to readily sense successful communication of said donor needle with blood in the vein of a donor.

13. A donor blood donation and sampling system according to claim 1 and wherein said clamping assembly is operative upon selectable clamping engagement with said blood sampling conduit to simultaneously block and pierce said blood sampling conduit.

14. A donor blood donation and sampling system according to claim 1 and wherein said sampling tube assembly comprises:
    a needle having first and second sharpened points at its opposite ends;
    a clamping assembly for selectable clamping engagement with a blood sampling conduit in fluid engagement with said needle, said clamping engagement causing piercing of said blood sampling conduit by said first sharpened point of said needle;
    a vacuum sampling tube receiving socket for removably receiving a vacuum sampling tube in fluid engagement with said needle at said second sharpened point, thereby providing fluid communication between blood in said blood sampling conduit and the interior of said vacuum sampling tube; and a retaining assembly for retaining said sampling tube assembly in engagement with at least said blood sampling conduit prior to clamping engagement therewith.

15. A sampling tube assembly for use in a donor blood sampling system and being arranged for selectable fluid engagement with a blood sampling conduit, said sampling tube assembly comprising:

a needle having first and second sharpened points at its opposite ends;

a clamping assembly for selectable clamping engagement with a blood sampling conduit in fluid engagement with said needle, said clamping engagement causing piercing of said blood sampling conduit by said first sharpened point of said needle;

a vacuum sampling tube receiving socket for removably receiving a vacuum sampling tube in fluid engagement with said needle at said second sharpened point, thereby providing fluid communication between blood in said blood sampling conduit and the interior of said vacuum sampling tube, said clamping assembly being operative upon selectable clamping engagement of said blood sampling conduit to simultaneously block at least one of said blood sampling conduit and a blood collection conduit engaged thereby and thus to selectably stop blood flow through at least one of said blood sampling conduit and said blood collection conduit.

16. A donor blood donation and sampling method comprising:

drawing blood from a body;

providing a blood collection bag which is coupled to a blood collection conduit which is, in turn, coupled to a donor needle;

coupling a blood sampling conduit to said donor needle; and arranging a sampling tube assembly in selectable fluid engagement with said blood sampling conduit, using a clamping assembly disposed within a housing element, for selectable clamping engagement with at least said blood collection conduit thus selectably stopping blood flow in at least said blood collection conduit and thereby providing blood to said sampling tube assembly prior to providing blood to said blood collection bag.

17. A donor blood donation and sampling method according to claim 16 and also comprising a breakaway cannula located on said blood collection conduit.

18. A donor blood donation and sampling method according to claim 17 and wherein said clamping assembly is also operative upon selectable clamping engagement with said blood sampling conduit to break said breakaway cannula, thereby permitting blood flow therethrough to said blood collection bag.

19. A donor blood donation and sampling method according to claim 16 and wherein blood is supplied initially to said blood sampling conduit and thereafter to said blood collection conduit without an intermediate stage wherein blood is supplied to neither said blood sampling conduit nor said blood collection conduit.

20. A donor blood donation and sampling method according to claim 16 and wherein said sampling tube assembly comprises:

a needle having first and second sharpened points at its opposite ends;

a clamping assembly for selectable clamping engagement with a blood sampling conduit in fluid engagement with said needle, said clamping engagement causing piercing of said blood sampling conduit by said first sharpened point of said needle;

a vacuum sampling tube receiving socket for removably receiving a vacuum sampling tube in fluid engagement with said needle at said second sharpened point, thereby providing fluid communication between blood in said blood sampling conduit and the interior of said vacuum sampling tube, said clamping assembly being operative upon selectable clamping engagement of a blood sampling conduit to simultaneously block at least one of said blood sampling conduit and a blood collection conduit engaged thereby, and wherein said sampling tube assembly is operative upon selectable clamping engagement with said blood sampling conduit to simultaneously block and pierce said blood sampling conduit, and wherein said sampling tube assembly is operative upon selectable clamping engagement with said blood sampling conduit and a blood collection conduit to simultaneously pierce said blood sampling conduit and block said blood collection conduit.

21. A donor blood sampling method for selectable fluid engagement with a blood sampling conduit, comprising:

providing a needle having first and second sharpened points at its opposite ends;

employing a clamping assembly for selectable clamping engagement with said blood sampling conduit in fluid engagement with said needle, said clamping engagement causing piercing of said blood sampling conduit by said first sharpened point of said needle;

operating a vacuum sampling tube receiving socket for removably receiving a vacuum sampling tube in fluid engagement with said needle at said second sharpened point, thereby providing fluid communication between blood in said blood sampling conduit and the interior of said vacuum sampling tube; and operating said clamping assembly to selectably engage said blood sampling conduit to simultaneously block at least one of said blood sampling conduit and a blood collection conduit engaged thereby and thus to selectably stop blood flow through at least one of said blood sampling conduit and said blood collection conduit.

22. A donor blood sampling method according to claim 21 and wherein said clamping assembly is operative upon selectable clamping engagement with said blood sampling conduit and a blood collection conduit to simultaneously pierce said blood sampling conduit and block said blood collection conduit.

* * * * *